United States Patent
Cao et al.

(10) Patent No.: US 11,059,897 B2
(45) Date of Patent: Jul. 13, 2021

(54) ANTI-IFNAR1 ANTIBODIES FOR TREATING AUTOIMMUNE DISEASES

(71) Applicant: I-Mab Biopharma US Limited, Gaithersburg, MD (US)

(72) Inventors: Wei Cao, Shanghai (CN); Weili Xu, Shanghai (CN)

(73) Assignee: I-Mab Biopharma US Limited, Gaithersburg, MD (US)

( * ) Notice: Subject to any disclaimer, the term of this patent is extended or adjusted under 35 U.S.C. 154(b) by 0 days.

(21) Appl. No.: 16/963,128

(22) PCT Filed: Sep. 18, 2019

(86) PCT No.: PCT/CN2019/106412
§ 371 (c)(1),
(2) Date: Jul. 17, 2020

(87) PCT Pub. No.: WO2020/057541
PCT Pub. Date: Mar. 26, 2020

(65) Prior Publication Data
US 2020/0399381 A1 Dec. 24, 2020

(30) Foreign Application Priority Data
Sep. 18, 2018 (WO) ................ PCT/CN2018/106157

(51) Int. Cl.
*C07K 16/28* (2006.01)
*A61K 39/00* (2006.01)
*G01N 33/53* (2006.01)

(52) U.S. Cl.
CPC ...... *C07K 16/2866* (2013.01); *C07K 2317/24* (2013.01); *C07K 2317/565* (2013.01)

(58) Field of Classification Search
None
See application file for complete search history.

(56) References Cited

U.S. PATENT DOCUMENTS

2008/0102072 A1  5/2008 Chuntharapai

FOREIGN PATENT DOCUMENTS

WO  WO 2006/002177  1/2006
WO  WO 2018/023976  12/2016

OTHER PUBLICATIONS

International Search Report and Written Opinion for PCT/CN2019/106412 dated Dec. 18, 2019, 12 pages.
Kawano, et al., "Blocking IFNAR1 inhibits multiple myeloma-driven Treg expansion and immunosuppression", The Journal of Clinical Investigation, vol. 128, No. 6, 2018, pp. 2487-2499.
Lu, et al. "Structure-function study of the extracellular domain of the human IFN-α receptor (hIFNAR1) using blocking monoclonal antibodies: the role of domains 1 and 2", The Journal of Immunology, vol. 160, 1998, pp. 1782-1788.
Runkel, et al. "Lupus clinical development: will belimumab's approval catalyse a new paradigm for SLE drug development", Expert Opinion on Biological Therapy, vol. 14, 2014, pp. 491-501.

*Primary Examiner* — Gary B Nickol
*Assistant Examiner* — Jegatheesan Seharaseyon
(74) *Attorney, Agent, or Firm* — Sheppard Mullin Richter & Hampton LLP

(57) ABSTRACT

Provided are antibodies or fragments thereof having binding specificity to the human interferon alpha and beta receptor subunit 1 (IFNAR1) protein. In various examples, the antibodies or fragments thereof include a VH and VL CDRs as provided, or variants thereof. Methods of using the antibodies or fragments thereof for treating autoimmune diseases and disorders are also provided.

15 Claims, 18 Drawing Sheets
Specification includes a Sequence Listing.

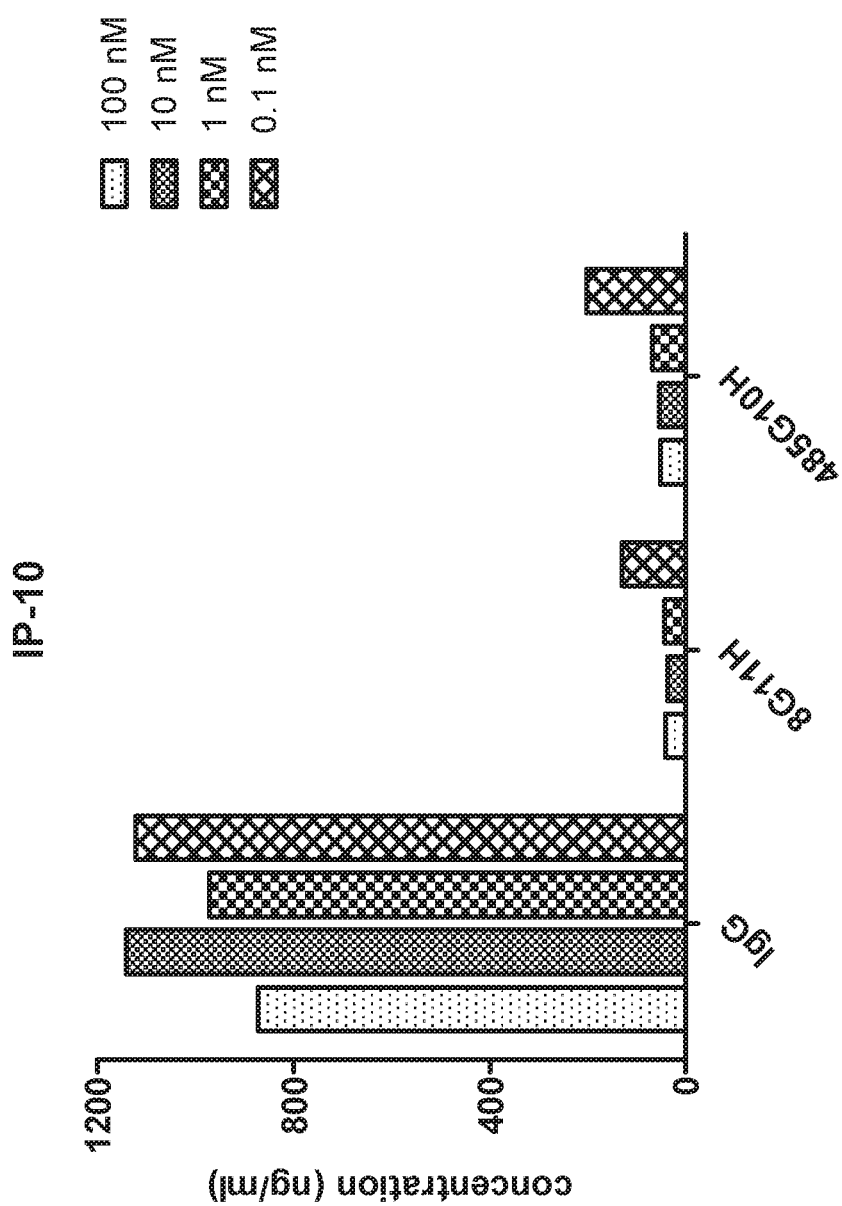

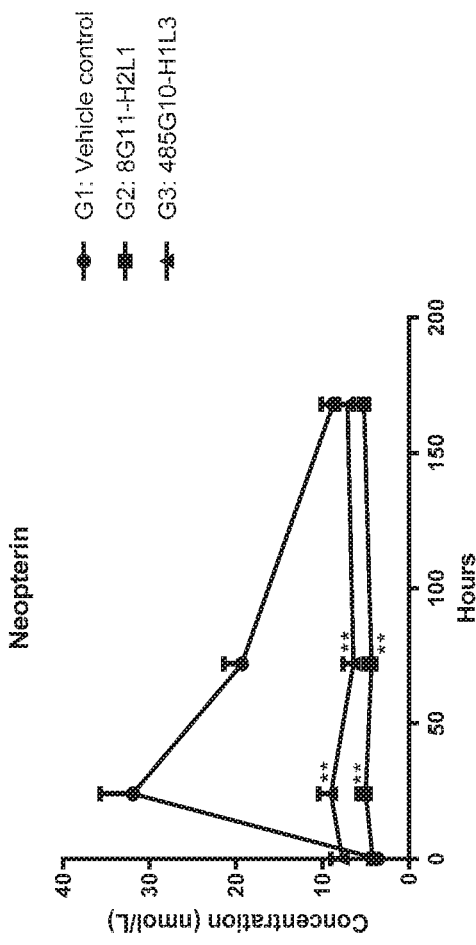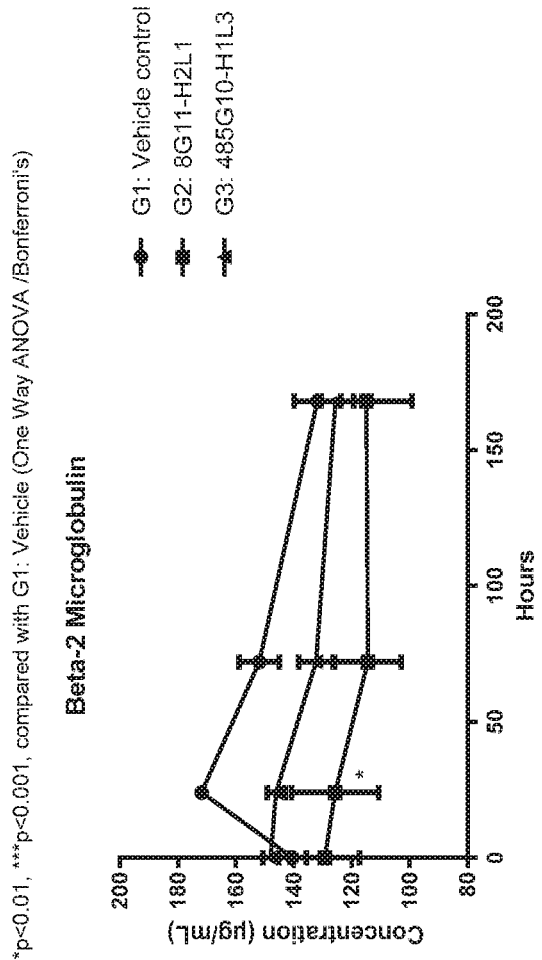
FIG. 11B

SEQUENCE LISTING

<160> NUMBER OF SEQ ID NOS: 206

<210> SEQ ID NO 1
<211> LENGTH: 118
<212> TYPE: PRT
<213> ORGANISM: Artificial Sequence
<220> FEATURE:
<223> OTHER INFORMATION: Synthetic

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Thr Glu Gln Gly Leu Glu Trp Ile
        35                  40                  45

Gly Arg Ile Asp Pro Asp Asp Gly Glu Thr Lys Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Gly Ser Leu Thr Ser Glu Asp Ala Ala Val Tyr Tyr Cys
                85                  90                  95

Ala Arg Gly Gly Asn Tyr Tyr Val Met Asp Asn Trp Gly Gln Gly Thr
            100                 105                 110

Ser Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Synthetic

<400> SEQUENCE: 2

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Ser Gly Gln Ser Pro Lys Ala Leu Ile
        35                  40                  45

Tyr Thr Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Leu Gln Ser
65                  70                  75                  80

Glu Asp Leu Ala Asp Tyr Leu Cys Gln Gln Tyr Phe Ser Tyr Pro His
                85                  90                  95

Thr Phe Gly Gly Gly Thr Lys Leu Glu Ile Lys
            100                 105

<210> SEQ ID NO 3
<211> LENGTH: 119
<212> TYPE: PRT
<213> ORGANISM: Artificial Sequence
<220> FEATURE:
<223> OTHER INFORMATION: Synthetic

<400> SEQUENCE: 3

Glu Val Gln Leu Gln Gln Ser Gly Ala Glu Leu Val Lys Pro Gly Ala
1               5                   10                  15

```
Ser Val Lys Leu Ser Cys Thr Ala Ser Gly Phe Asn Ile Lys Asp Ser
            20                  25                  30

Tyr Met His Trp Val Lys Glu Arg Thr Glu Gln Gly Leu Glu Trp Ile
        35                  40                  45

Gly Arg Ile Asp Pro Glu Asp Gly Glu Thr Asn Tyr Ala Pro Lys Phe
 50                  55                  60

Gln Gly Lys Ala Thr Leu Thr Ala Asp Thr Ser Ser Asn Thr Ala Tyr
65                  70                  75                  80

Leu Gln Leu Ser Gly Leu Thr Ser Glu Asp Thr Ala Val Tyr Tyr Cys
                85                  90                  95

Ala Arg Arg Val Ser Ser Leu Tyr Ala Met Asp Tyr Trp Gly Gln Gly
            100                 105                 110

Thr Ser Val Thr Val Ser Ser
            115
```

<210> SEQ ID NO 4
<211> LENGTH: 107
<212> TYPE: PRT
<213> ORGANISM: Artificial Sequence
<220> FEATURE:
<223> OTHER INFORMATION: Synthetic

<400> SEQUENCE: 4

```
Asp Ile Val Met Thr Gln Ser Gln Lys Ser Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Leu Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Trp
                85                  90                  95

Thr Phe Gly Gly Gly Thr Lys Leu Glu Ile Lys
            100                 105
```

<210> SEQ ID NO 5
<211> LENGTH: 118
<212> TYPE: PRT
<213> ORGANISM: Artificial Sequence
<220> FEATURE:
<223> OTHER INFORMATION: Synthetic

<400> SEQUENCE: 5

```
Glu Val Arg Leu Gln Gln Ser Gly Ala Glu Leu Val Gln Pro Gly Ala
1               5                   10                  15

Ser Val Lys Leu Ser Cys Thr Gly Phe Gly Phe Asn Ile Lys Asp Tyr
            20                  25                  30

Tyr Met His Trp Val Lys Gln Arg Thr Glu Gln Gly Leu Glu Trp Ile
        35                  40                  45

Gly Arg Ile Asp Pro Glu Asp Ala Glu Thr Lys Tyr Ala Pro Lys Phe
 50                  55                  60

Gln Gly Gln Ala Thr Ile Thr Ala Asp Thr Ser Ser Asn Thr Ala Tyr
65                  70                  75                  80

Val Gln Val Ser Ser Leu Ser Ser Glu Asp Thr Ala Val Tyr Tyr Cys
```

85                  90                  95

Ala Arg Gly Gly Asn Phe Tyr Val Met Asp Tyr Trp Gln Gly Thr
            100                 105                 110

Ser Val Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: Synthetic

<400> SEQUENCE: 6

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Val Trp Tyr Gln Gln Lys Pro Gly Gln Ser Pro Lys Val Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Ile Ile Ser Asn Val Gln Ser
65                  70                  75                  80

Glu Asp Leu Ala Glu Tyr Phe Cys Gln Gln Lys Asn Ser Tyr Pro Tyr
                85                  90                  95

Thr Phe Gly Gly Gly Thr Lys Leu Glu Ile Lys
            100                 105

<210> SEQ ID NO 7
<211> LENGTH: 118
<212> TYPE: PRT
<213> ORGANISM: Artificial Sequence
<220> FEATURE:
<223> OTHER INFORMATION: Synthetic

<400> SEQUENCE: 7

Glu Val Gln Leu Gln Gln Ser Gly Ala Glu Leu Val Lys Pro Gly Ala
1               5                   10                  15

Ser Val Lys Leu Ser Cys Thr Gly Phe Gly Phe Asn Ile Lys Asp Tyr
            20                  25                  30

Tyr Met His Trp Val Lys Gln Arg Ala Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Val Ser Ser Leu Thr Ser Glu Asp Thr Ala Val Tyr Tyr Cys
                85                  90                  95

Ala Arg Gly Gly Asn Phe Tyr Val Met Asp Tyr Trp Gln Gly Thr
            100                 105                 110

Ser Val Thr Val Ser Ser
        115

<210> SEQ ID NO 8
<211> LENGTH: 107
<212> TYPE: PRT
<213> ORGANISM: Artificial Sequence
<220> FEATURE:

<223> OTHER INFORMATION: Synthetic

<400> SEQUENCE: 8

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Val Trp Tyr Gln Gln Lys Pro Gly Gln Ser Pro Lys Val Leu Ile
            35                  40                  45

Tyr Ser Ala Ser Tyr Arg Val Ser Gly Val Pro Asp Arg Phe Thr Gly
    50                  55                  60

Ser Gly Ser Gly Thr Asp Phe Thr Leu Ile Ile Ser Asn Val Gln Ser
65                  70                  75                  80

Glu Asp Leu Ala Glu Tyr Phe Cys Gln Gln Lys Asn Asn Tyr Pro Tyr
                85                  90                  95

Thr Phe Gly Gly Gly Thr Lys Leu Glu Ile Lys
            100                 105
```

<210> SEQ ID NO 9
<211> LENGTH: 118
<212> TYPE: PRT
<213> ORGANISM: Artificial Sequence
<220> FEATURE:
<223> OTHER INFORMATION: Synthetic

<400> SEQUENCE: 9

```
Ala Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
                20                  25                  30

Tyr Met His Trp Val Lys Gln Arg Thr Glu Gln Gly Leu Glu Trp Ile
            35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Gly Asn Tyr Tyr Ala Met Asp Tyr Trp Gly Gln Gly Thr
            100                 105                 110

Ser Val Thr Val Ser Ser
        115
```

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
```

```
                   50                  55                  60
Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln His Asn Ser Tyr Thr Tyr
                     85                  90                  95

Lys Phe Gly Gly Gly Thr Lys Val Glu Ile Lys
                100                 105
```

<210> SEQ ID NO 11
<211> LENGTH: 118
<212> TYPE: PRT
<213> ORGANISM: Artificial Sequence
<220> FEATURE:
<223> OTHER INFORMATION: Synthetic

<400> SEQUENCE: 11

```
Glu Val Gln Leu Leu Gln Ser Trp Ala Asp Leu Val Lys Pro Gly Ala
  1               5                  10                  15

Ser Val Lys Leu Ser Cys Thr Ala Ser Gly Phe Asn Ile Lys Asp Tyr
                 20                  25                  30

Tyr Ile His Trp Val Lys Gln Arg Thr Glu Gln Gly Leu Glu Trp Ile
             35                  40                  45

Gly Arg Ile Asp Pro Glu Asp Gly Glu Thr Lys Tyr Ala Pro Lys Phe
 50                  55                  60

Gln Asp Lys Ala Ala Ile Thr Ala Asp Thr Ser Ser Asn Thr Ala Tyr
 65                  70                  75                  80

Leu Gln Leu Ser Ser Leu Thr Ser Glu Gly Thr Ala Val Tyr Tyr Cys
                 85                  90                  95

Ala Arg Tyr Asp Gly Tyr Tyr Gly Phe Asp Tyr Trp Gly Gln Gly Thr
                100                 105                 110

Thr Leu Thr Val Ser Ser
            115
```

<210> SEQ ID NO 12
<211> LENGTH: 107
<212> TYPE: PRT
<213> ORGANISM: Artificial Sequence
<220> FEATURE:
<223> OTHER INFORMATION: Synthetic

<400> SEQUENCE: 12

```
Asp Ile Val Met Thr Gln Ser Gln Lys Phe Met Ser Thr Ser Val Gly
  1               5                  10                  15

Asp Arg Val Ser Val Thr Cys Lys Ala Ser Gln Asn Val Gly Thr Asn
                 20                  25                  30

Val Ala Trp Tyr Gln Gln Lys Pro Gly Gln Ser Pro Lys Pro Leu Ile
             35                  40                  45

Tyr Ser Thr Ser Tyr Arg Tyr Ser Gly Val Pro Asp Arg Phe Thr Gly
 50                  55                  60

Ser Gly Ser Gly Thr Asp Phe Thr Leu Thr Ile Thr Asn Val Gln Ser
 65                  70                  75                  80

Glu Asp Leu Ala Glu Tyr Phe Cys His Gln Tyr Asn Asn Tyr Pro Tyr
                 85                  90                  95

Thr Phe Gly Gly Gly Thr Lys Leu Glu Ile Lys
                100                 105
```

<210> SEQ ID NO 13
<211> LENGTH: 118

<212> TYPE: PRT
<213> ORGANISM: Artificial Sequence
<220> FEATURE:
<223> OTHER INFORMATION: Synthetic

<400> SEQUENCE: 13

Glu Val Gln Leu Gln Gln Ser Gly Ala Lys Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met Cys Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Ser
65                  70                  75                  80

Leu Gln Leu Ser Ser Leu Thr Ser Glu Asp Thr Ala Val Tyr Tyr Cys
                85                  90                  95

Ala Arg Gly Gly Asn Tyr Tyr Ala Met Asp Tyr Trp Gly Gln Gly Thr
            100                 105                 110

Ser Val Thr Val Ser Ser
        115

<210> SEQ ID NO 14
<211> LENGTH: 107
<212> TYPE: PRT
<213> ORGANISM: Artificial Sequence
<220> FEATURE:
<223> OTHER INFORMATION: Synthetic

<400> SEQUENCE: 14

Asp Thr Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Thr Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln His Asn Ser Tyr Ser Tyr
                85                  90                  95

Thr Phe Gly Gly Gly Thr Lys Leu Glu Ile Lys
            100                 105

<210> SEQ ID NO 15
<211> LENGTH: 117
<212> TYPE: PRT
<213> ORGANISM: Artificial Sequence
<220> FEATURE:
<223> OTHER INFORMATION: Synthetic

<400> SEQUENCE: 15

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Thr Glu Gln Gly Leu Glu Trp Ile

```
                35                  40                  45
Gly Arg Ile Asp Pro Glu Asp Gly Glu Thr Lys Tyr Ala Pro Lys Phe
         50                  55                  60
Gln Gly Lys Ala Thr Ile Thr Ala Asp Thr Ser Ser Asn Thr Ala Tyr
 65                  70                  75                  80
Leu Gln Leu Ser Ser Leu Thr Ser Glu Asp Thr Ala Val Tyr Tyr Cys
                 85                  90                  95
Ala Arg Leu Gly Asn Trp Val Phe Asp Tyr Trp Gly Gln Gly Thr Thr
            100                 105                 110
Leu Thr Val Ser Ser
        115

<210> SEQ ID NO 16
<211> LENGTH: 105
<212> TYPE: PRT
<213> ORGANISM: Artificial Sequence
<220> FEATURE:
<223> OTHER INFORMATION: Synthetic

<400> SEQUENCE: 16

Asp Thr Val Met Thr Gln Ser Gln Lys Phe Met Ser Thr Ser Val Gly
 1               5                  10                  15
Asp Arg Val Ser Val Thr Cys Lys Ala Ser Gln Asn Val Gly Thr Asn
             20                  25                  30
Val Asp Trp Tyr Gln Gln Lys Ser Gly Gln Ser Pro Lys Ala Leu Ile
         35                  40                  45
Tyr Ser Ala Ser Tyr Arg Tyr Ser Gly Val Pro Asp Arg Phe Thr Gly
     50                  55                  60
Ser Gly Ser Gly Thr Asp Phe Thr Leu Thr Ile Ser Asn Val Gln Ser
 65                  70                  75                  80
Glu Asp Leu Ala Glu Tyr Phe Cys Gln Gln Tyr Asn Thr Tyr Thr Phe
                 85                  90                  95
Gly Gly Gly Thr Lys Leu Glu Ile Lys
            100                 105

<210> SEQ ID NO 17
<211> LENGTH: 118
<212> TYPE: PRT
<213> ORGANISM: Artificial Sequence
<220> FEATURE:
<223> OTHER INFORMATION: Synthetic

<400> SEQUENCE: 17

Glu Val Gln Leu Gln Gln Phe Gly Ala Glu Leu Val Lys Pro Gly Ala
 1               5                  10                  15
Ser Val Lys Leu Ser Cys Thr Ala Ser Gly Phe Asn Ile Lys Asp Tyr
             20                  25                  30
Tyr Met His Trp Val Lys Gln Arg Thr Glu Gln Gly Leu Glu Trp Ile
         35                  40                  45
Gly Arg Ile Asp Pro Glu Asp Gly Glu Thr Lys Tyr Ala Pro Lys Phe
         50                  55                  60
Gln Val Lys Ala Thr Ile Thr Ala Asp Thr Ser Ser Asn Thr Ala Tyr
 65                  70                  75                  80
Leu His Phe Ser Ser Leu Thr Ser Glu Asp Thr Ala Val Tyr Tyr Cys
                 85                  90                  95
Val Arg Gly Gly Asn Phe Tyr Tyr Phe Asp Tyr Trp Gly Gln Gly Thr
            100                 105                 110
```

```
Thr Leu Thr Val Ser Ser
        115

<210> SEQ ID NO 18
<211> LENGTH: 107
<212> TYPE: PRT
<213> ORGANISM: Artificial Sequence
<220> FEATURE:
<223> OTHER INFORMATION: Synthetic

<400> SEQUENCE: 18

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Cys Ile Asn Tyr Pro Tyr
                85                  90                  95

Thr Phe Gly Gly Gly Thr Lys Leu Glu Ile Lys
            100                 105

<210> SEQ ID NO 19
<211> LENGTH: 118
<212> TYPE: PRT
<213> ORGANISM: Artificial Sequence
<220> FEATURE:
<223> OTHER INFORMATION: Synthetic

<400> SEQUENCE: 19

Glu Val His Leu Gln Gln Ser Gly Ala Glu Leu Val Lys Pro Gly Thr
1               5                   10                  15

Ser Leu Lys Leu Ser Cys Thr Ala Ser Gly Phe Asn Ile Lys Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Thr Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Tyr Asn Gly Tyr Ser Gly Phe Asp Tyr Trp Gly Gln Gly Thr
            100                 105                 110

Thr Leu Thr Val Ser Ser
        115

<210> SEQ ID NO 20
<211> LENGTH: 107
<212> TYPE: PRT
<213> ORGANISM: Artificial Sequence
<220> FEATURE:
<223> OTHER INFORMATION: Synthetic

<400> SEQUENCE: 20

Asp Ile Val Met Thr Gln Ser Gln Lys Phe Met Ser Thr Ser Glu Gly
```

```
            1               5                  10                 15
Asp Arg Val Ser Val Thr Cys Lys Ala Ser Gln Asn Val Gly Thr Asn
                20                  25                 30

Val Val Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Arg Tyr Pro Phe
                85                  90                  95

Thr Phe Gly Ala Gly Thr Lys Leu Glu Leu Lys
                100                 105
```

```
<210> SEQ ID NO 21
<211> LENGTH: 118
<212> TYPE: PRT
<213> ORGANISM: Artificial Sequence
<220> FEATURE:
<223> OTHER INFORMATION: Synthetic

<400> SEQUENCE: 21

Glu Val Gln Leu Leu Gln Ser Trp Ala Asp Leu Val Lys Pro Gly Ala
1               5                   10                  15

Ser Val Lys Leu Ser Cys Thr Ala Ser Gly Phe Asn Ile Lys Asp Tyr
                20                  25                  30

Tyr Ile His Trp Val Lys Gln Arg Thr Glu Gln Gly Leu Glu Trp Ile
            35                  40                  45

Gly Arg Ile Asp Pro Glu Asp Gly Glu Thr Lys Tyr Ala Pro Lys Phe
        50                  55                  60

Gln Asp Lys Ala Ala Ile Thr Ala Asp Thr Ser Ser Asn Thr Ala Tyr
65                  70                  75                  80

Leu Gln Leu Ser Ser Leu Thr Ser Glu Gly Thr Ala Val Tyr Tyr Cys
                85                  90                  95

Ala Arg Tyr Asp Gly Tyr Tyr Gly Phe Asp Tyr Trp Gly Gln Gly Thr
                100                 105                 110

Thr Leu Thr Val Ser Ser
        115
```

```
<210> SEQ ID NO 22
<211> LENGTH: 107
<212> TYPE: PRT
<213> ORGANISM: Artificial Sequence
<220> FEATURE:
<223> OTHER INFORMATION: Synthetic

<400> SEQUENCE: 22

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Pro Leu Ile
            35                  40                  45

Tyr Ser Thr Ser Tyr Arg Tyr Ser Gly Val Pro Asp Arg Phe Thr Gly
        50                  55                  60

Ser Gly Ser Gly Thr Asp Phe Thr Leu Thr Ile Thr Asn Val Gln Ser
65                  70                  75                  80
```

Glu Asp Leu Ala Glu Tyr Phe Cys His Gln Tyr Asn Asn Tyr Pro Tyr
                85                  90                  95

Thr Phe Gly Gly Gly Thr Lys Leu Glu Ile Lys
            100                 105

<210> SEQ ID NO 23
<211> LENGTH: 118
<212> TYPE: PRT
<213> ORGANISM: Artificial Sequence
<220> FEATURE:
<223> OTHER INFORMATION: Synthetic

<400> SEQUENCE: 23

Glu Val Gln Leu Gln Gln Ser Gly Ala Glu Val Val Lys Pro Gly Ala
1               5                   10                  15

Ser Val Lys Leu Ser Cys Thr Ala Ser Gly Phe Asn Ile Lys Asp Tyr
                20                  25                  30

Tyr Met His Trp Val Lys Gln Arg Thr Glu Gln Gly Leu Glu Cys Ile
            35                  40                  45

Gly Arg Ile Asp Pro Glu Asp Gly Glu Thr Lys Tyr Val Pro Lys Phe
    50                  55                  60

Gln Gly Lys Ala Thr Ile Thr Ala Glu Thr Ser Ser Asn Thr Ala Tyr
65                  70                  75                  80

Leu Gln Leu Ser Ser Leu Thr Ala Glu Asp Thr Ala Val Tyr Tyr Cys
                85                  90                  95

Ser Arg Gly Gly Ser Tyr Tyr Val Met Asp Tyr Trp Gly Gln Gly Thr
            100                 105                 110

Ser Val Thr Val Ser Ser
            115

<210> SEQ ID NO 24
<211> LENGTH: 107
<212> TYPE: PRT
<213> ORGANISM: Artificial Sequence
<220> FEATURE:
<223> OTHER INFORMATION: Synthetic

<400> SEQUENCE: 24

Asp Val Val Met Thr Gln Ser Arg Lys Phe Met Ser Thr Ser Val Gly
1               5                   10                  15

Asp Arg Val Ser Val Thr Cys Lys Ala Ser Gln Asn Val Gly Thr Ser
                20                  25                  30

Val Ala Trp Tyr Gln Gln Lys Leu Gly Gln Ser Pro Lys Ala Leu Ile
            35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Asp Asn Ser Tyr Pro His
                85                  90                  95

Thr Phe Gly Gly Gly Thr Lys Leu Glu Ile Lys
            100                 105

<210> SEQ ID NO 25
<211> LENGTH: 116
<212> TYPE: PRT
<213> ORGANISM: Artificial Sequence
<220> FEATURE:
<223> OTHER INFORMATION: Synthetic

<400> SEQUENCE: 25

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Ser Leu His Trp Ser Leu Asp Ser Trp Gly Gln Gly Thr Thr Leu
            100                 105                 110

Thr Val Ser Ser
        115

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Pro Gly Gln Ser Pro Lys Pro Leu Ile
        35                  40                  45

Tyr Ser Thr Ala Asn Arg Asp Thr Gly Val Pro Asp Arg Phe Thr Gly
50                  55                  60

Ser Gly Ser Gly Thr Asp Phe Thr Leu Thr Ile Ser Asn Met Gln Ser
65                  70                  75                  80

Glu Asp Leu Ala His Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 27
<211> LENGTH: 118
<212> TYPE: PRT
<213> ORGANISM: Artificial Sequence
<220> FEATURE:
<223> OTHER INFORMATION: Synthetic

<400> SEQUENCE: 27

Asp Val Gln Leu Gln Gln Ser Gly Ala Glu Leu Val Lys Pro Gly Ala
1               5                   10                  15

Ser Val Asn Leu Ser Cys Thr Gly Ser Gly Phe Asn Ile Lys Asp Tyr
            20                  25                  30

Tyr Ile His Trp Val Lys Gln Arg Thr Glu Gln Gly Leu Glu Trp Ile
        35                  40                  45

Gly Arg Val Asp Pro Glu Asp Gly Glu Thr Lys Tyr Val Pro Lys Phe
50                  55                  60

```
Leu Asp Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Thr Arg Gly Gly Asn Tyr Tyr Ala Met Asp Tyr Trp Gly Gln Gly Thr
            100                 105                 110

Ser Val Thr Val Ser Ser
            115
```

<210> SEQ ID NO 28
<211> LENGTH: 107
<212> TYPE: PRT
<213> ORGANISM: Artificial Sequence
<220> FEATURE:
<223> OTHER INFORMATION: Synthetic

<400> SEQUENCE: 28

```
Asp Ile Val Met Thr Gln Ser Gln Lys Phe Met Ser Thr Ser Val Gly
  1               5                  10                  15

Asp Arg Val Ser Val Thr Cys Lys Ala Ser Gln Asn Val Gly Thr Asn
             20                  25                  30

Val Ala Trp Tyr Gln Gln Lys Ser Gly Gln Ser Pro Lys Ala Leu Ile
         35                  40                  45

Phe Leu Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Cys Asn Asn Tyr Arg Leu
                 85                  90                  95

Thr Phe Gly Ser Gly Thr Lys Leu Glu Ile Lys
            100                 105
```

<210> SEQ ID NO 29
<211> LENGTH: 118
<212> TYPE: PRT
<213> ORGANISM: Artificial Sequence
<220> FEATURE:
<223> OTHER INFORMATION: Synthetic

<400> SEQUENCE: 29

```
Glu Val Gln Leu Leu Gln Ser Trp Ala Asp Leu Val Lys Pro Gly Ala
  1               5                  10                  15

Ser Val Lys Leu Ser Cys Thr Ala Ser Gly Phe Asn Ile Lys Asp Tyr
             20                  25                  30

Tyr Ile His Trp Val Lys Gln Arg Thr Glu Gln Gly Leu Glu Trp Ile
         35                  40                  45

Gly Arg Ile Asp Pro Glu Asp Gly Glu Thr Lys Tyr Ala Pro Lys Phe
 50                  55                  60

Gln Asp Lys Ala Ala Ile Thr Ala Asp Thr Ser Ser Asn Thr Ala Tyr
 65                  70                  75                  80

Leu Gln Leu Ser Ser Leu Thr Ser Glu Gly Thr Ala Val Tyr Tyr Cys
                 85                  90                  95

Ala Arg Tyr Asp Gly Tyr Gly Phe Asp Tyr Trp Gly Gln Gly Thr
            100                 105                 110

Thr Leu Thr Val Ser Ser
            115
```

<210> SEQ ID NO 30

<211> LENGTH: 107
<212> TYPE: PRT
<213> ORGANISM: Artificial Sequence
<220> FEATURE:
<223> OTHER INFORMATION: Synthetic

<400> SEQUENCE: 30

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Thr Ser Tyr Arg Tyr Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys His Gln Tyr Asn Asn Tyr Pro Tyr
                85                  90                  95

Thr Phe Gly Gly Gly Thr Lys Leu Glu Ile Lys
            100                 105

<210> SEQ ID NO 31
<211> LENGTH: 119
<212> TYPE: PRT
<213> ORGANISM: Artificial Sequence
<220> FEATURE:
<223> OTHER INFORMATION: Synthetic

<400> SEQUENCE: 31

Glu Ala Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Arg Asp Ser
            20                  25                  30

Tyr Ile His Trp Val Asn Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Trp Leu Ala Asp Tyr Ser Ala Met Asp Asn Trp Gly Gln Gly
            100                 105                 110

Thr Ser Val Thr Val Ser Ser
        115

<210> SEQ ID NO 32
<211> LENGTH: 107
<212> TYPE: PRT
<213> ORGANISM: Artificial Sequence
<220> FEATURE:
<223> OTHER INFORMATION: Synthetic

<400> SEQUENCE: 32

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
 50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Asn Thr Leu Tyr
                85                  90                  95

Thr Phe Gly Gly Gly Thr Lys Leu Glu Met Lys
            100                 105

<210> SEQ ID NO 33
<211> LENGTH: 119
<212> TYPE: PRT
<213> ORGANISM: Artificial Sequence
<220> FEATURE:
<223> OTHER INFORMATION: Synthetic

<400> SEQUENCE: 33

Glu Val Gln Leu Gln Gln Ser Gly Ala Glu Leu Val Lys Pro Gly Ala
1               5                   10                  15

Ser Val Lys Leu Ser Cys Thr Ser Ser Gly Phe Asn Ile Lys Asp Ser
            20                  25                  30

Tyr Met His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Ala Arg Arg Gly Ser Ser Leu Tyr Ala Val Asp Tyr Trp Gly Gln Gly
            100                 105                 110

Thr Ser Val Thr Val Ser Ser
        115

<210> SEQ ID NO 34
<211> LENGTH: 107
<212> TYPE: PRT
<213> ORGANISM: Artificial Sequence
<220> FEATURE:
<223> OTHER INFORMATION: Synthetic

<400> SEQUENCE: 34

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Ser
            20                  25                  30

Val Ala Trp Tyr Gln Gln Lys Pro Gly Gln Ser Pro Lys Ala Val Ile
        35                  40                  45

Tyr Leu Ala Ser Tyr Arg His Arg Gly Val Pro Ala Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Phe Asn Ile Tyr Pro Trp
                85                  90                  95

Thr Phe Gly Gly Gly Thr Lys Leu Glu Ile Lys
            100                 105

<210> SEQ ID NO 35
<211> LENGTH: 118
<212> TYPE: PRT
<213> ORGANISM: Artificial Sequence
<220> FEATURE:
<223> OTHER INFORMATION: Synthetic

<400> SEQUENCE: 35

Glu Val Gln Leu Leu Gln Ser Gly Ala Glu Leu Val Lys Pro Gly Ala
1               5                   10                  15

Ser Val Arg Leu Ser Cys Thr Ala Ser Gly Phe Asn Ile Lys Asp Tyr
            20                  25                  30

Tyr Leu His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Gly Gly Asn Tyr Asp Val Met Asp Tyr Trp Gly Gln Gly Thr
            100                 105                 110

Ser Val Thr Val Ser Ser
        115

<210> SEQ ID NO 36
<211> LENGTH: 107
<212> TYPE: PRT
<213> ORGANISM: Artificial Sequence
<220> FEATURE:
<223> OTHER INFORMATION: Synthetic

<400> SEQUENCE: 36

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Tyr
            20                  25                  30

Val Val Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Gly Asn Val Gln Ser
65                  70                  75                  80

Glu Asp Leu Ala Glu Tyr Phe Cys Gln Gln Lys Asn Thr Tyr Pro Phe
                85                  90                  95

Thr Phe Gly Gly Gly Thr Lys Leu Glu Ile Glu
            100                 105

<210> SEQ ID NO 37
<211> LENGTH: 119
<212> TYPE: PRT
<213> ORGANISM: Artificial Sequence
<220> FEATURE:
<223> OTHER INFORMATION: Synthetic

<400> SEQUENCE: 37

Glu Val Gln Leu Gln Gln Ser Gly Ala Glu Leu Val Lys Pro Gly Ala
1               5                   10                  15

Ser Val Lys Leu Ser Cys Thr Ser Ser Gly Phe Asn Ile Lys Asp Ser
            20                  25                  30

Tyr Met His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Ala Arg Arg Gly Ser Ser Leu Tyr Ala Val Asp Tyr Trp Gly Gln Gly
            100                 105                 110

Thr Ser Val Thr Val Ser Ser
            115

<210> SEQ ID NO 38
<211> LENGTH: 107
<212> TYPE: PRT
<213> ORGANISM: Artificial Sequence
<220> FEATURE:
<223> OTHER INFORMATION: Synthetic

<400> SEQUENCE: 38

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Ser
            20                  25                  30

Val Ala Trp Tyr Gln Gln Lys Pro Gly Gln Ser Pro Lys Ala Val Ile
        35                  40                  45

Tyr Leu Ala Ser Tyr Arg His Arg Gly Val Pro Ala Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Phe Asn Ile Tyr Pro Trp
                85                  90                  95

Thr Phe Gly Gly Gly Thr Lys Leu Glu Ile Lys
            100                 105

<210> SEQ ID NO 39
<211> LENGTH: 118
<212> TYPE: PRT
<213> ORGANISM: Artificial Sequence
<220> FEATURE:
<223> OTHER INFORMATION: Synthetic

<400> SEQUENCE: 39

Glu Val Gln Leu Gln Gln Ser Gly Ala Asp Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Val Lys Thr Thr Ile Thr Ala Asp Thr Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Val Arg Gly Gly Asn Phe Tyr Tyr Phe Asp Tyr Trp Gly Gln Gly Ser
            100                 105                 110

Thr Leu Thr Val Ser Ser
        115

<210> SEQ ID NO 40
<211> LENGTH: 107
<212> TYPE: PRT
<213> ORGANISM: Artificial Sequence
<220> FEATURE:
<223> OTHER INFORMATION: Synthetic

<400> SEQUENCE: 40

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Cys Ile Asn Tyr Pro Tyr
                85                  90                  95

Thr Phe Gly Gly Gly Thr Lys Leu Glu Ile Lys
            100                 105

<210> SEQ ID NO 41
<211> LENGTH: 118
<212> TYPE: PRT
<213> ORGANISM: Artificial Sequence
<220> FEATURE:
<223> OTHER INFORMATION: Synthetic

<400> SEQUENCE: 41

Glu Val Gln Leu Gln Gln Ser Gly Ala Glu Leu Val Lys Ser Gly Ala
1               5                   10                  15

Ser Val Arg Leu Ser Cys Thr Ala Ser Gly Phe Asn Ile Lys Asp Tyr
            20                  25                  30

Tyr Met His Trp Val Lys Gln Arg Thr Glu Lys Gly Leu Glu Trp Ile
        35                  40                  45

Gly Arg Ile Asp Pro Glu Asp Gly Glu Thr Lys Tyr Val Pro Lys Phe
    50                  55                  60

Gln Gly Lys Ala Thr Ile Thr Ala Asp Thr Ser Ser Asn Thr Val Tyr
65                  70                  75                  80

Leu Gln Leu Asn Ser Leu Thr Ser Glu Asp Thr Ala Val Tyr Tyr Cys
                85                  90                  95

Val Arg Gly Gly Asn Tyr Tyr Val Met Asp Tyr Trp Gly Gln Gly Thr
            100                 105                 110

Ser Val Thr Val Ser Ser
        115

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Tyr
            20                  25                  30

Val Ala Trp Tyr Gln Gln Lys Pro Gly Gln Ser Pro Lys Val Val Ile
        35                  40                  45

Tyr Ser Ala Ser Tyr Arg Tyr Asn Gly Val Pro Asp Arg Phe Thr Gly
50                  55                  60

Ser Gly Ser Gly Thr Asp Phe Thr Leu Thr Ile Ser Asn Val Gln Pro
65                  70                  75                  80

Glu Asp Leu Ala Glu Tyr Phe Cys Gln Gln Tyr Asn Asn Tyr Pro Leu
                85                  90                  95

Thr Phe Gly Ser Gly Thr Lys Leu Glu Ile Lys
            100                 105

<210> SEQ ID NO 43
<211> LENGTH: 118
<212> TYPE: PRT
<213> ORGANISM: Artificial Sequence
<220> FEATURE:
<223> OTHER INFORMATION: Synthetic

<400> SEQUENCE: 43

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Thr Glu Gln Gly Leu Glu Leu Ile
        35                  40                  45

Gly Arg Ile Asp Pro Glu Asp Gly Glu Thr Lys Tyr Ala Pro Lys Phe
50                  55                  60

Gln Val Lys Ala Thr Ile Thr Ala Asp Ala Ser Ser Asn Thr Ala Tyr
65                  70                  75                  80

Leu Gln Phe Ser Ser Leu Thr Ser Glu Asp Ala Ala Val Tyr Tyr Cys
                85                  90                  95

Val Arg Gly Gly Asn Phe Tyr Tyr Phe Asp Tyr Trp Gly Gln Gly Thr
            100                 105                 110

Thr Leu Thr Val Ser Ser
        115

<210> SEQ ID NO 44
<211> LENGTH: 107
<212> TYPE: PRT
<213> ORGANISM: Artificial Sequence
<220> FEATURE:
<223> OTHER INFORMATION: Synthetic

<400> SEQUENCE: 44

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Val
        35                  40                  45

Tyr Ser Ala Ser Tyr Arg Tyr Ser Gly Val Pro Asp Arg Phe Thr Gly
50                  55                  60

Ser Gly Ser Gly Thr Asp Phe Thr Leu Thr Ile Ser Asp Val Gln Ser
65                  70                  75                  80

Glu Asp Leu Ala Glu Tyr Phe Cys Gln Gln Cys Ile Asn Tyr Pro Tyr
                85                  90                  95

Thr Phe Gly Gly Gly Thr Lys Leu Glu Ile Lys
            100                 105

<210> SEQ ID NO 45
<211> LENGTH: 118
<212> TYPE: PRT
<213> ORGANISM: Artificial Sequence
<220> FEATURE:
<223> OTHER INFORMATION: Synthetic

<400> SEQUENCE: 45

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ser Arg Gly Gly Asn Phe Tyr Tyr Phe Asp Tyr Trp Gly Gln Gly Thr
            100                 105                 110

Ser Leu Thr Val Ser Ser
        115

<210> SEQ ID NO 46
<211> LENGTH: 107
<212> TYPE: PRT
<213> ORGANISM: Artificial Sequence
<220> FEATURE:
<223> OTHER INFORMATION: Synthetic

<400> SEQUENCE: 46

Asp Ile Val Met Thr Gln Ser Gln Lys Phe Met Ser Thr Leu Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Cys Asn Ser Tyr Ser Tyr
                85                  90                  95

Thr Phe Gly Gly Gly Thr Lys Leu Glu Ile Lys
            100                 105

<210> SEQ ID NO 47
<211> LENGTH: 118
<212> TYPE: PRT

<213> ORGANISM: Artificial Sequence
<220> FEATURE:
<223> OTHER INFORMATION: Synthetic

<400> SEQUENCE: 47

Glu Val Gln Leu Gln Gln Ser Gly Ala Glu Val Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Thr Glu Gln Gly Leu Glu Cys Ile
        35                  40                  45

Gly Arg Ile Asp Pro Glu Asp Gly Glu Thr Lys Tyr Val Pro Lys Phe
50                  55                  60

Gln Gly Lys Ala Thr Ile Thr Ala Glu Thr Ser Ser Asn Thr Ala Tyr
65                  70                  75                  80

Leu Gln Leu Ser Ser Leu Thr Ala Glu Asp Thr Ala Val Tyr Tyr Cys
                85                  90                  95

Ser Arg Gly Gly Ser Tyr Val Met Asp Tyr Trp Gly Gln Gly Thr
            100                 105                 110

Ser Val Thr Val Ser Ser
        115

<210> SEQ ID NO 48
<211> LENGTH: 107
<212> TYPE: PRT
<213> ORGANISM: Artificial Sequence
<220> FEATURE:
<223> OTHER INFORMATION: Synthetic

<400> SEQUENCE: 48

Asp Val Val Met Thr Gln Ser Arg Lys Phe Met Ser Thr Ser Val Gly
1               5                   10                  15

Asp Arg Val Ser Val Thr Cys Lys Ala Ser Gln Asn Val Gly Thr Ser
            20                  25                  30

Val Ala Trp Tyr Gln Gln Lys Leu Gly Gln Ser Pro Lys Ala Leu Ile
        35                  40                  45

Tyr Ser Ala Ser Tyr Arg Tyr Ser Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Asp Asn Ser Tyr Pro His
                85                  90                  95

Thr Phe Gly Gly Gly Thr Lys Leu Glu Ile Lys
            100                 105

<210> SEQ ID NO 49
<211> LENGTH: 118
<212> TYPE: PRT
<213> ORGANISM: Artificial Sequence
<220> FEATURE:
<223> OTHER INFORMATION: Synthetic

<400> SEQUENCE: 49

Glu Val Gln Leu Gln Gln Ser Gly Ala Glu Leu Val Lys Pro Gly Ala
1               5                   10                  15

Ser Val Lys Val Ser Cys Thr Gly Ser Gly Phe Asn Ile Lys Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
            50                  55                  60

Gln Gly Lys Ala Thr Ile Thr Ser Asp Thr Ser Ser Asn Thr Ala Tyr
 65                  70                  75                  80

Leu Gln Leu Ser Ser Leu Thr Ser Gly Asp Thr Ala Val Tyr Phe Cys
                85                  90                  95

Ala Arg Tyr Asp Gly Tyr Tyr Cys Phe Asp Tyr Trp Gly Gln Gly Thr
                100                 105                 110

Thr Leu Thr Val Ser Ser
            115

<210> SEQ ID NO 50
<211> LENGTH: 107
<212> TYPE: PRT
<213> ORGANISM: Artificial Sequence
<220> FEATURE:
<223> OTHER INFORMATION: Synthetic

<400> SEQUENCE: 50

Asp Ile Val Met Thr Gln Ser Gln Lys Phe Met Ser Thr Ser Val Gly
 1               5                  10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Pro Leu Ile
            35                  40                  45

Tyr Ser Thr Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Ala Asp Leu Ala Ala Tyr Phe Cys Gln Gln Tyr Asn Asn Tyr Pro Tyr
                85                  90                  95

Thr Phe Gly Gly Gly Thr Arg Leu Glu Ile Lys
                100                 105

<210> SEQ ID NO 51
<211> LENGTH: 117
<212> TYPE: PRT
<213> ORGANISM: Artificial Sequence
<220> FEATURE:
<223> OTHER INFORMATION: Synthetic

<400> SEQUENCE: 51

Glu Val Gln Leu Gln Gln Ser Gly Ala Asp Leu Val Lys Pro Gly Ala
 1               5                  10                  15

Ser Val Lys Leu Ser Cys Thr Thr Ser Gly Phe Asn Ile Lys Asp Tyr
                20                  25                  30

Tyr Met His Trp Val Asn Gln Arg Thr Glu Gln Gly Leu Glu Trp Ile
            35                  40                  45

Gly Arg Ile Asp Pro Glu Asp Gly Glu Thr Lys Tyr Ala Pro Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                85                  90                  95

Ala Arg Asp Trp Gly His Ser Phe Asp Tyr Trp Gly Gln Gly Thr Thr
                100                 105                 110

Leu Thr Val Ser Ser

```
<210> SEQ ID NO 52
<211> LENGTH: 105
<212> TYPE: PRT
<213> ORGANISM: Artificial Sequence
<220> FEATURE:
<223> OTHER INFORMATION: Synthetic

<400> SEQUENCE: 52

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Thr
            20                  25                  30

Val Ala Trp Tyr Gln Gln Lys Pro Gly Gln Ser Pro Lys Thr Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Thr Phe
                85                  90                  95

Gly Gly Gly Thr Lys Leu Glu Met Lys
            100                 105

<210> SEQ ID NO 53
<211> LENGTH: 119
<212> TYPE: PRT
<213> ORGANISM: Artificial Sequence
<220> FEATURE:
<223> OTHER INFORMATION: Synthetic

<400> SEQUENCE: 53

Glu Val Gln Leu Gln Gln Ser Gly Ala Glu Phe Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Thr Gln Lys Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Asp Lys Ala Thr Ile Thr Ala Asp Ser Ser Asn Thr Ala Tyr
65                  70                  75                  80

Leu Gln Leu Ser Ser Leu Thr Ser Val Asp Thr Ala Val Tyr Phe Cys
                85                  90                  95

Ser Arg Glu Gly Ser Phe Thr Gly Trp Phe Pro Tyr Trp Gly Gln Gly
            100                 105                 110

Thr Leu Val Ser Val Ser Ala
        115

<210> SEQ ID NO 54
<211> LENGTH: 107
<212> TYPE: PRT
<213> ORGANISM: Artificial Sequence
<220> FEATURE:
<223> OTHER INFORMATION: Synthetic

<400> SEQUENCE: 54

Asp Ile Val Met Thr Gln Ser Gln Lys Phe Met Ser Thr Ser Val Gly
1               5                   10                  15
```

Asp Arg Val Ser Val Thr Cys Lys Ala Arg Gln Ser Val Gly Thr Tyr
            20                  25                  30

Val Ala Trp Tyr Gln Gln Lys Pro Gly Gln Ser Pro Lys Ala Leu Ile
        35                  40                  45

Tyr Ser Thr Ser Tyr Arg Tyr Asn Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr His Ser Tyr Pro Tyr
                85                  90                  95

Thr Phe Gly Gly Gly Thr Lys Leu Glu Ile Lys
            100                 105

<210> SEQ ID NO 55
<211> LENGTH: 118
<212> TYPE: PRT
<213> ORGANISM: Artificial Sequence
<220> FEATURE:
<223> OTHER INFORMATION: Synthetic

<400> SEQUENCE: 55

Glu Val Gln Leu Gln Gln Ser Gly Ala Glu Leu Val Lys Pro Gly Ala
1               5                   10                  15

Ser Val Lys Val Ser Cys Thr Ser Gly Phe Asn Ile Lys Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Arg Ala Thr Ile Thr Ser Asp Thr Ser Ser Asn Thr Ala Tyr
65                  70                  75                  80

Leu Gln Leu Ser Ser Leu Thr Ser Gly Asp Thr Ala Val Tyr Tyr Cys
                85                  90                  95

Ala Arg Tyr Asp Gly Tyr Tyr Cys Phe Asp Tyr Trp Gly Gln Gly Thr
            100                 105                 110

Thr Leu Thr Val Ser Ser
        115

<210> SEQ ID NO 56
<211> LENGTH: 107
<212> TYPE: PRT
<213> ORGANISM: Artificial Sequence
<220> FEATURE:
<223> OTHER INFORMATION: Synthetic

<400> SEQUENCE: 56

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Thr Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Ala Asp Leu Ala Ala Tyr Phe Cys Gln Gln Tyr Asn Asn Tyr Pro Tyr

Thr Phe Gly Gly Gly Thr Arg Leu Glu Ile Lys
            100                 105

<210> SEQ ID NO 57
<211> LENGTH: 117
<212> TYPE: PRT
<213> ORGANISM: Artificial Sequence
<220> FEATURE:
<223> OTHER INFORMATION: Synthetic

<400> SEQUENCE: 57

Glu Val Gln Leu Gln Glu Ser Gly Pro Gly Leu Ala Lys Pro Ser Gln
1               5                   10                  15

Thr Leu Ser Leu Thr Cys Ser Val Thr Gly Tyr Ser Ile Thr Ser Asp
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ser Ile Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Asn Glu Asp Thr Ala Thr Tyr Tyr Cys Ala
                85                  90                  95

Arg Ser Gly Gly Met Tyr Tyr Phe Asp Tyr Trp Gly Gln Gly Thr Thr
            100                 105                 110

Leu Thr Val Ser Ser
        115

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Glu Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ile Pro Pro
                85                  90                  95

Thr Phe Gly Ser Gly Thr Lys Leu Glu Ile Lys
            100                 105

<210> SEQ ID NO 59
<211> LENGTH: 117
<212> TYPE: PRT
<213> ORGANISM: Artificial Sequence
<220> FEATURE:
<223> OTHER INFORMATION: Synthetic

<400> SEQUENCE: 59

Glu Val Gln Leu Gln Glu Ser Gly Pro Gly Leu Ala Lys Pro Ser Gln
1               5                   10                  15

Thr Leu Ser Leu Thr Cys Ser Val Thr Gly Tyr Ser Ile Thr Ser Asp
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ser Ile Tyr Tyr Asn Pro Ser Leu Lys
    50                  55                  60

Ser Arg Ile Ser Ile Thr Arg Ala Thr Ser Lys Asn Gln Tyr Tyr Leu
65                  70                  75                  80

Gln Leu Asn Ser Val Thr Asn Glu Asp Thr Ala Thr Tyr Tyr Cys Ala
                85                  90                  95

Arg Ser Gly Gly Met Tyr Tyr Phe Asp Tyr Trp Gly Gln Gly Thr Thr
            100                 105                 110

Leu Thr Val Ser Ser
        115

<210> SEQ ID NO 60
<211> LENGTH: 107
<212> TYPE: PRT
<213> ORGANISM: Artificial Sequence
<220> FEATURE:
<223> OTHER INFORMATION: Synthetic

<400> SEQUENCE: 60

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Glu Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ile Pro Pro
                85                  90                  95

Thr Phe Gly Ser Gly Thr Lys Leu Glu Ile Lys
            100                 105

<210> SEQ ID NO 61
<211> LENGTH: 117
<212> TYPE: PRT
<213> ORGANISM: Artificial Sequence
<220> FEATURE:
<223> OTHER INFORMATION: Synthetic

<400> SEQUENCE: 61

Glu Val Gln Leu Gln Glu Ser Gly Pro Gly Leu Ala Lys Pro Ser Gln
1               5                   10                  15

Thr Leu Ser Leu Thr Cys Ser Val Thr Gly Tyr Ser Ile Thr Ser Asp
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Thr Ile Tyr Tyr Asn Pro Ser Leu Lys
    50                  55                  60

Ser Arg Ile Ser Ile Thr Arg Asp Thr Ser Lys Asn Gln Tyr Tyr Leu

```
                  65                  70                  75                  80
Gln Leu Asn Ser Val Thr Asn Glu Asp Thr Ala Thr Tyr Tyr Cys Ala
                    85                  90                  95

Arg Ser Gly Gly Met Tyr Tyr Phe Asp Tyr Trp Gly Gln Gly Thr Thr
                100                 105                 110

Leu Thr Val Ser Ser
            115

<210> SEQ ID NO 62
<211> LENGTH: 107
<212> TYPE: PRT
<213> ORGANISM: Artificial Sequence
<220> FEATURE:
<223> OTHER INFORMATION: Synthetic

<400> SEQUENCE: 62

Asp Ile Gln Met Thr Gln Ser Pro Ala Ser Leu Ser Ala Ser Val Gly
1               5                  10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Glu Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ile Pro Pro
                85                  90                  95

Thr Phe Gly Ser Gly Thr Lys Leu Glu Ile Lys
                100                 105

<210> SEQ ID NO 63
<211> LENGTH: 117
<212> TYPE: PRT
<213> ORGANISM: Artificial Sequence
<220> FEATURE:
<223> OTHER INFORMATION: Synthetic

<400> SEQUENCE: 63

Glu Val Gln Leu Gln Glu Ser Gly Pro Gly Leu Ala Lys Pro Ser Gln
1               5                  10                  15

Thr Leu Ser Leu Thr Cys Ser Val Thr Gly Tyr Ser Ile Thr Ser Asp
                20                  25                  30

Tyr Trp Asn Trp Ile Arg Lys Phe Pro Gly Asn Lys Leu Glu Tyr Met
            35                  40                  45

Gly Tyr Ile Ser Tyr Ser Gly Asn Thr Asp Tyr Asn Pro Ser Leu Lys
    50                  55                  60

Ser Arg Phe Ser Ile Thr Arg Asp Thr Ser Lys Asn Gln Phe Tyr Leu
65                  70                  75                  80

Gln Leu Asn Ser Val Thr Thr Glu Asp Thr Ala Thr Tyr Tyr Cys Ala
                85                  90                  95

Arg Ser Glu Gly Met Tyr Phe Phe Asp Tyr Trp Gly Gln Gly Thr Thr
                100                 105                 110

Leu Thr Val Ser Ser
            115

<210> SEQ ID NO 64
<211> LENGTH: 107
```

```
<212> TYPE: PRT
<213> ORGANISM: Artificial Sequence
<220> FEATURE:
<223> OTHER INFORMATION: Synthetic

<400> SEQUENCE: 64

Asp Ile Gln Met Thr Gln Ser Pro Ala Ser Leu Ser Ala Ser Val Gly
1               5                   10                  15

Glu Thr Val Ser Ile Thr Cys Arg Ala Ser Gly Asn Ile His Asn Tyr
            20                  25                  30

Leu Ala Trp Tyr His Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Pro
                85                  90                  95

Thr Phe Gly Ser Gly Thr Lys Leu Glu Ile Lys
            100                 105

<210> SEQ ID NO 65
<211> LENGTH: 118
<212> TYPE: PRT
<213> ORGANISM: Artificial Sequence
<220> FEATURE:
<223> OTHER INFORMATION: Synthetic

<400> SEQUENCE: 65

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Phe Gly Gly Leu Thr Ala Met Asp Tyr Trp Gly Gln Gly Thr
            100                 105                 110

Ser Val Thr Val Ser Ser
        115

<210> SEQ ID NO 66
<211> LENGTH: 107
<212> TYPE: PRT
<213> ORGANISM: Artificial Sequence
<220> FEATURE:
<223> OTHER INFORMATION: Synthetic

<400> SEQUENCE: 66

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
```

```
                35                  40                  45
Tyr Ala Thr Ser Tyr Arg Tyr Ser Gly Val Pro Asp Arg Phe Thr Gly
        50                  55                  60
Ser Gly Ser Gly Thr Asp Phe Thr Leu Thr Ile Ser Asn Val Gln Ser
65                  70                  75                  80
Glu Asp Leu Ala Glu Tyr Phe Cys Gln Gln Tyr Asn Asn Tyr Pro Tyr
                85                  90                  95
Thr Phe Gly Gly Gly Thr Lys Leu Glu Ile Lys
            100                 105
```

<210> SEQ ID NO 67
<211> LENGTH: 118
<212> TYPE: PRT
<213> ORGANISM: Artificial Sequence
<220> FEATURE:
<223> OTHER INFORMATION: Synthetic

<400> SEQUENCE: 67

```
Ala Val Gln Leu Gln Gln Ser Gly Thr Glu Leu Val Lys Pro Gly Ala
1               5                   10                  15
Ser Val Lys Leu Ser Cys Ser Ala Ser Gly Phe Asn Ile Lys Asp Tyr
            20                  25                  30
Tyr Val His Trp Val Lys Gln Lys Thr Glu Gln Gly Leu Glu Trp Ile
        35                  40                  45
Gly Arg Ile Asp Pro Glu Asp Gly Glu Thr Lys Tyr Ala Pro Lys Phe
    50                  55                  60
Gln Gly Lys Ala Thr Val Thr Ala Asp Thr Ser Ser Asn Thr Ala Tyr
65                  70                  75                  80
Met Gln Leu Ser Ser Leu Thr Ser Glu Asp Thr Ala Val Tyr Tyr Cys
                85                  90                  95
Thr Arg Phe Gly Gly Leu Asp Ala Met Asp Tyr Trp Gly Gln Gly Thr
            100                 105                 110
Ser Val Thr Val Ser Ser
        115
```

<210> SEQ ID NO 68
<211> LENGTH: 107
<212> TYPE: PRT
<213> ORGANISM: Artificial Sequence
<220> FEATURE:
<223> OTHER INFORMATION: Synthetic

<400> SEQUENCE: 68

```
Asp Ile Val Met Thr Gln Ser Gln Lys Phe Met Ser Thr Ser Val Gly
1               5                   10                  15
Asp Arg Val Ser Val Thr Cys Lys Ala Ser Gln Asn Val Gly Thr Asn
            20                  25                  30
Val Ala Trp Tyr Gln Gln Lys Pro Gly Gln Ser Pro Lys Pro Leu Ile
        35                  40                  45
Tyr Ser Thr Ser Tyr Arg Tyr Asn Gly Val Pro Asp Arg Phe Thr Gly
    50                  55                  60
Ser Gly Ser Gly Thr Glu Phe Thr Leu Thr Ile Ser Asn Val Gln Ser
65                  70                  75                  80
Glu Asp Leu Ala Glu Tyr Phe Cys Gln Gln Phe Asn Arg Tyr Pro Tyr
                85                  90                  95
Thr Phe Gly Gly Gly Thr Lys Leu Glu Ile Lys
            100                 105
```

```
<210> SEQ ID NO 69
<211> LENGTH: 120
<212> TYPE: PRT
<213> ORGANISM: Artificial Sequence
<220> FEATURE:
<223> OTHER INFORMATION: Synthetic

<400> SEQUENCE: 69

Gln Val Gln Leu Gln Gln Ser Gly Ala Glu Leu Val Lys Pro Gly Ser
1               5                   10                  15

Ser Val Lys Ile Ser Cys Lys Ala Ser Gly Phe Thr Phe Thr Ser His
            20                  25                  30

Phe Ile His Trp Ile Lys Gln Pro Gly Asn Gly Leu Lys Trp Ile
        35                  40                  45

Gly Trp Ile Tyr Pro Gly Asp Asp Thr Glu Tyr Asn His Lys Phe
    50                  55                  60

Asn Gly Lys Ala Thr Leu Thr Ala Asp Lys Ser Ser Thr Ala Tyr
65                  70                  75                  80

Met His Leu Ser Ser Leu Thr Ser Glu Asp Ser Ala Val Tyr Phe Cys
                85                  90                  95

Ala Arg Arg Val Glu Tyr Tyr Asn Gly Gly Phe Ala Tyr Trp Gly Gln
            100                 105                 110

Gly Thr Leu Val Thr Val Ser Ser
        115                 120

<210> SEQ ID NO 70
<211> LENGTH: 107
<212> TYPE: PRT
<213> ORGANISM: Artificial Sequence
<220> FEATURE:
<223> OTHER INFORMATION: Synthetic

<400> SEQUENCE: 70

Asp Val Gln Met Thr Gln Ser Pro Ser Tyr Leu Ala Ala Pro Gly
1               5                   10                  15

Glu Ser Val Ser Ile Ser Cys Lys Ala Ser Lys Asn Ile Arg Asn Asn
            20                  25                  30

Leu Gly Trp Tyr Gln Glu Arg Pro Gly Lys Thr Pro Asn Leu Leu Ile
        35                  40                  45

His Ser Gly Ser Thr Leu Gln Ser Gly Ala Pro Ser Arg Phe Ser Gly
    50                  55                  60

Gly Gly Ser Gly Thr Asp Phe Thr Leu Thr Ile Arg Ser Leu Glu Ser
65                  70                  75                  80

Glu Asp Ser Ala Val Tyr Tyr Cys Gln Gln Tyr Asp Gln Tyr Pro Leu
                85                  90                  95

Thr Phe Gly Ser Gly Thr Lys Leu Glu Ile Lys
            100                 105

<210> SEQ ID NO 71
<211> LENGTH: 124
<212> TYPE: PRT
<213> ORGANISM: Artificial Sequence
<220> FEATURE:
<223> OTHER INFORMATION: Synthetic

<400> SEQUENCE: 71

Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Asn Thr Tyr
```

```
                20                  25                  30
Gly Met Gly Val Gly Trp Ile Arg Gln Pro Ser Gly Lys Gly Leu Glu
             35                  40                  45

Trp Leu Ala Asn Ile Trp Trp Asp Asp Lys Tyr Tyr Asn Pro Ser
 50                  55                  60

Leu Lys Asn Arg Leu Thr Ile Ser Lys Asp Thr Ser Asn Asn Gln Ala
 65                  70                  75                  80

Phe Leu Lys Ile Thr Asn Val Asp Thr Ala Asp Thr Ala Thr Tyr Phe
                 85                  90                  95

Cys Ala Arg His Pro Leu Pro Gly Tyr Lys Asp Asn Tyr Val Val Asp
            100                 105                 110

Ala Trp Gly Gln Gly Ala Ser Val Thr Val Ser Ser
            115                 120

<210> SEQ ID NO 72
<211> LENGTH: 112
<212> TYPE: PRT
<213> ORGANISM: Artificial Sequence
<220> FEATURE:
<223> OTHER INFORMATION: Synthetic

<400> SEQUENCE: 72

Asp Val Val Leu Thr Gln Thr Pro Gly Ser Leu Ser Val Thr Leu Gly
 1               5                  10                  15

Asp Gln Ala Ser Ile Ser Cys Arg Ser Ser Gln Ser Leu Glu Tyr Ser
             20                  25                  30

Asp Gln Tyr Thr Tyr Leu Glu Trp Tyr Leu Gln Lys Ser Gly Gln Ser
         35                  40                  45

Pro Gln Leu Leu Ile Tyr Gly Val Ser Asn Arg Phe Ser Gly Val Pro
 50                  55                  60

Asp Arg Phe Ile Gly Ser Gly Ser Gly Thr Asp Phe Thr Leu Lys Ile
 65                  70                  75                  80

Ser Arg Val Glu Pro Glu Asp Leu Gly Val Tyr Tyr Cys Phe Gln Ala
                 85                  90                  95

Thr His Asp Pro Tyr Thr Phe Gly Ala Gly Thr Lys Leu Glu Leu Lys
            100                 105                 110

<210> SEQ ID NO 73
<211> LENGTH: 118
<212> TYPE: PRT
<213> ORGANISM: Artificial Sequence
<220> FEATURE:
<223> OTHER INFORMATION: Synthetic

<400> SEQUENCE: 73

Glu Val Gln Leu Gln Gln Ser Gly Ala Glu Leu Val Lys Pro Gly Ala
 1               5                  10                  15

Ser Val Lys Leu Ser Cys Thr Gly Ser Gly Phe Asn Ile Lys Asp Tyr
             20                  25                  30

Tyr Ile His Trp Val Lys Gln Arg Thr Glu Gln Gly Leu Glu Trp Ile
             35                  40                  45

Gly Arg Ile Asp Pro Glu Asp Gly Glu Thr Lys Tyr Ala Pro Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Val Val Tyr Tyr Cys
                 85                  90                  95
```

Gly Arg Tyr His Gly Tyr Trp Ala Leu Asp Tyr Trp Gly Gln Gly Thr
            100                 105                 110

Ser Val Thr Val Ser Ser
        115

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

Asp Ile Val Met Thr Gln Ser Gln Lys Phe Met Ser Thr Ser Val Gly
1               5                   10                  15

Asp Arg Val Ser Val Thr Cys Lys Thr Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Thr Ser Tyr Arg Tyr Ser Gly Val Pro Asp Arg Phe Thr Gly
    50                  55                  60

Ser Gly Ser Gly Thr Asp Phe Thr Leu Ile Ile Ser Asn Val Gln Ser
65                  70                  75                  80

Glu Asp Leu Ala Glu Tyr Phe Cys His Gln Tyr Phe Ser Tyr Pro Tyr
                85                  90                  95

Thr Phe Gly Gly Gly Thr Leu Leu Glu Ile Lys
            100                 105

<210> SEQ ID NO 75
<211> LENGTH: 117
<212> TYPE: PRT
<213> ORGANISM: Artificial Sequence
<220> FEATURE:
<223> OTHER INFORMATION: Synthetic

<400> SEQUENCE: 75

Glu Val Gln Leu Gln Gln Ser Gly Ala Glu Leu Val Lys Pro Gly Ala
1               5                   10                  15

Ser Val Lys Leu Ser Cys Ser Ala Ser Gly Phe Asn Ile Lys Asp Cys
            20                  25                  30

Tyr Ile His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Ala Lys Ala Thr Ile Thr Ala Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Ala Arg His Cys Asn Phe Leu Tyr Phe Asp Tyr Trp Gly Gln Gly Ser
            100                 105                 110

Thr Leu Thr Val Ser
        115

<210> SEQ ID NO 76
<211> LENGTH: 107
<212> TYPE: PRT
<213> ORGANISM: Artificial Sequence
<220> FEATURE:
<223> OTHER INFORMATION: Synthetic

<400> SEQUENCE: 76

Asp Ile Val Met Thr Gln Ser Gln Lys Ser Met Ser Thr Ser Leu Gly
1               5                   10                  15

Asp Arg Val Thr Val Thr Cys Lys Ala Ser Gln Asn Val Gly Thr Ile
            20                  25                  30

Val Ala Trp Tyr Gln Leu Lys Pro Gly Gln Ser Pro Lys Thr Leu Ile
        35                  40                  45

Tyr Ser Ala Ser Tyr Arg Ser Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Val
                85                  90                  95

Ile Phe Gly Ser Gly Thr Lys Leu Glu Ile Arg
            100                 105

<210> SEQ ID NO 77
<211> LENGTH: 5
<212> TYPE: PRT
<213> ORGANISM: Artificial Sequence
<220> FEATURE:
<223> OTHER INFORMATION: Synthetic

<400> SEQUENCE: 77

Asp Tyr Tyr Met His
1               5

<210> SEQ ID NO 78
<211> LENGTH: 17
<212> TYPE: PRT
<213> ORGANISM: Artificial Sequence
<220> FEATURE:
<223> OTHER INFORMATION: Synthetic

<400> SEQUENCE: 78

Arg Ile Asp Pro Glu Asp Gly Glu Thr Lys Tyr Ala Pro Lys Phe Gln
1               5                   10                  15

Gly

<210> SEQ ID NO 79
<211> LENGTH: 17
<212> TYPE: PRT
<213> ORGANISM: Artificial Sequence
<220> FEATURE:
<223> OTHER INFORMATION: Synthetic

<400> SEQUENCE: 79

Arg Ile Asp Pro Glu Asp Ala Glu Thr Lys Tyr Ala Pro Lys Phe Gln
1               5                   10                  15

Gly

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gly Gly Asn Phe Tyr Val Met Asp Tyr
1               5

<210> SEQ ID NO 81
<211> LENGTH: 11
<212> TYPE: PRT
<213> ORGANISM: Artificial Sequence
<220> FEATURE:
<223> OTHER INFORMATION: Synthetic

<400> SEQUENCE: 81

Lys Ala Ser Gln Asn Val Gly Thr Asn Val Val
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Synthetic

<400> SEQUENCE: 82

Ser Ala Ser Tyr Arg Val Ser
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic

<400> SEQUENCE: 83

Gln Gln Lys Asn Asn Tyr Pro Tyr Thr
1               5

<210> SEQ ID NO 84
<211> LENGTH: 118
<212> TYPE: PRT
<213> ORGANISM: Artificial Sequence
<220> FEATURE:
<223> OTHER INFORMATION: Synthetic

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Met
        35                  40                  45

Gly Arg Ile Asp Pro Glu Asp Ala Glu Thr Lys Tyr Ala Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Phe Tyr Val Met Asp Tyr Trp Gly Gln Gly Thr
            100                 105                 110

Leu Val Thr Val Ser Ser
        115

<210> SEQ ID NO 85
<211> LENGTH: 118
<212> TYPE: PRT
<213> ORGANISM: Artificial Sequence
<220> FEATURE:

<223> OTHER INFORMATION: Synthetic

<400> SEQUENCE: 85

Gln Val Gln Leu Val Gln Ser Gly Ala Glu Val Val Lys Pro Gly Ala
1               5                   10                  15

Ser Val Lys Val Ser Cys Lys Gly Ser Gly Phe Asn Ile Lys Asp Tyr
            20                  25                  30

Tyr Met His Trp Val Arg Gln Ala Pro Gly Gln Gly Leu Glu Trp Ile
        35                  40                  45

Gly Arg Ile Asp Pro Glu Asp Ala Glu Thr Lys Tyr Ala Pro Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Phe Tyr Val Met Asp Tyr Trp Gly Gln Gly Thr
            100                 105                 110

Leu Val Thr Val Ser Ser
        115

<210> SEQ ID NO 86
<211> LENGTH: 118
<212> TYPE: PRT
<213> ORGANISM: Artificial Sequence
<220> FEATURE:
<223> OTHER INFORMATION: Synthetic

<400> SEQUENCE: 86

Gln Val Gln Leu Val Gln Ser Gly Ala Glu Val Val Lys Pro Gly Ala
1               5                   10                  15

Ser Val Lys Val Ser Cys Lys Gly Ser Gly Phe Asn Ile Lys Asp Tyr
            20                  25                  30

Tyr Met His Trp Val Lys Gln Ala Pro Gly Gln Gly Leu Glu Trp Ile
        35                  40                  45

Gly Arg Ile Asp Pro Glu Asp Ala Glu Thr Lys Tyr Ala Pro Lys Phe
    50                  55                  60

Gln Gly Arg Val Thr Ile Thr Ala Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Gly Gly Asn Phe Tyr Val Met Asp Tyr Trp Gly Gln Gly Thr
            100                 105                 110

Leu Val Thr Val Ser Ser
        115

<210> SEQ ID NO 87
<211> LENGTH: 118
<212> TYPE: PRT
<213> ORGANISM: Artificial Sequence
<220> FEATURE:
<223> OTHER INFORMATION: Synthetic

<400> SEQUENCE: 87

Gln Val Gln Leu Val Gln Ser Gly Ala Glu Val Val Lys Pro Gly Ala
1               5                   10                  15

Ser Val Lys Leu Ser Cys Lys Gly Ser Gly Phe Asn Ile Lys Asp Tyr
            20                  25                  30

Tyr Met His Trp Val Lys Gln Ala Pro Gly Gln Gly Leu Glu Trp Ile

```
                35                  40                  45
Gly Arg Ile Asp Pro Glu Asp Ala Glu Thr Lys Tyr Ala Pro Lys Phe
 50                  55                  60

Gln Gly Arg Ala Thr Ile Thr Ala Asp Thr Ser Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Gly Gly Asn Phe Tyr Val Met Asp Tyr Trp Gly Gln Gly Thr
            100                 105                 110

Leu Val Thr Val Ser Ser
        115

<210> SEQ ID NO 88
<211> LENGTH: 107
<212> TYPE: PRT
<213> ORGANISM: Artificial Sequence
<220> FEATURE:
<223> OTHER INFORMATION: Synthetic

<400> SEQUENCE: 88

Asp Ile Gln Leu Thr Gln Ser Pro Ser Phe Leu Ser Ala Ser Val Gly
 1               5                  10                  15

Asp Arg Val Thr Ile Thr Cys Lys Ala Ser Gln Asn Val Gly Thr Asn
            20                  25                  30

Val Val Trp Tyr Gln Gln Lys Pro Gly Lys Ala Pro Lys Leu Leu Ile
         35                  40                  45

Tyr Ser Ala Ser Tyr Arg Val Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Lys Asn Asn Tyr Pro Tyr
                 85                  90                  95

Thr Phe Gly Gln Gly Thr Lys Leu Glu Ile Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: Synthetic

<400> SEQUENCE: 89

Asp Ile Gln Leu Thr Gln Ser Pro Ser Phe Leu Ser Thr Ser Val Gly
 1               5                  10                  15

Asp Arg Val Thr Ile Thr Cys Lys Ala Ser Gln Asn Val Gly Thr Asn
            20                  25                  30

Val Val Trp Tyr Gln Gln Lys Pro Gly Lys Ser Pro Lys Val Leu Ile
         35                  40                  45

Tyr Ser Ala Ser Tyr Arg Val Ser Gly Val Pro Ser Arg Phe Ser Gly
 50                  55                  60

Ser Gly Ser Gly Thr Glu Phe Thr Leu Ile Ile Ser Ser Leu Gln Pro
 65                  70                  75                  80

Glu Asp Phe Ala Thr Tyr Tyr Cys Gln Gln Lys Asn Asn Tyr Pro Tyr
                 85                  90                  95

Thr Phe Gly Gln Gly Thr Lys Leu Glu Ile Lys
            100                 105
```

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

Asp Ile Gln Leu Thr Gln Ser Pro Ser Phe Leu Ser Thr Ser Val Gly
1               5                   10                  15

Asp Arg Val Thr Ile Thr Cys Lys Ala Ser Gln Asn Val Gly Thr Asn
            20                  25                  30

Val Val Trp Tyr Gln Gln Lys Pro Gly Lys Ser Pro Lys Val Leu Ile
        35                  40                  45

Tyr Ser Ala Ser Tyr Arg Val Ser Gly Val Pro Ser Arg Phe Ser Gly
    50                  55                  60

Ser Gly Ser Gly Thr Glu Phe Thr Leu Ile Ile Ser Ser Val Gln Pro
65                  70                  75                  80

Glu Asp Phe Ala Thr Tyr Phe Cys Gln Gln Lys Asn Asn Tyr Pro Tyr
                85                  90                  95

Thr Phe Gly Gln Gly Thr Lys Leu Glu Ile Lys
            100                 105

<210> SEQ ID NO 91
<211> LENGTH: 107
<212> TYPE: PRT
<213> ORGANISM: Artificial Sequence
<220> FEATURE:
<223> OTHER INFORMATION: Synthetic

<400> SEQUENCE: 91

Asp Ile Gln Met Thr Gln Ser Pro Ser Phe Leu Ser Thr Ser Val Gly
1               5                   10                  15

Asp Arg Val Thr Val Thr Cys Lys Ala Ser Gln Asn Val Gly Thr Asn
            20                  25                  30

Val Val Trp Tyr Gln Gln Lys Pro Gly Lys Ser Pro Lys Val Leu Ile
        35                  40                  45

Tyr Ser Ala Ser Tyr Arg Val Ser Gly Val Pro Ser Arg Phe Ser Gly
    50                  55                  60

Ser Gly Ser Gly Thr Glu Phe Thr Leu Ile Ile Ser Ser Val Gln Pro
65                  70                  75                  80

Glu Asp Phe Ala Thr Tyr Phe Cys Gln Gln Lys Asn Asn Tyr Pro Tyr
                85                  90                  95

Thr Phe Gly Gln Gly Thr Lys Leu Glu Ile Lys
            100                 105

<210> SEQ ID NO 92
<211> LENGTH: 5
<212> TYPE: PRT
<213> ORGANISM: Artificial Sequence
<220> FEATURE:
<223> OTHER INFORMATION: Synthetic

<400> SEQUENCE: 92

Asp Tyr Tyr Ile His
1               5

<210> SEQ ID NO 93
<211> LENGTH: 17
<212> TYPE: PRT

<213> ORGANISM: Artificial Sequence
<220> FEATURE:
<223> OTHER INFORMATION: Synthetic

<400> SEQUENCE: 93

Arg Ile Asp Pro Glu Asp Gly Glu Thr Lys Tyr Ala Pro Lys Phe Gln
1               5                   10                  15
Gly

<210> SEQ ID NO 94
<211> LENGTH: 17
<212> TYPE: PRT
<213> ORGANISM: Artificial Sequence
<220> FEATURE:
<223> OTHER INFORMATION: Synthetic

<400> SEQUENCE: 94

Arg Ile Asp Pro Glu Asp Ala Glu Thr Lys Tyr Ala Pro Lys Phe Gln
1               5                   10                  15
Gly

<210> SEQ ID NO 95
<211> LENGTH: 9
<212> TYPE: PRT
<213> ORGANISM: Artificial Sequence
<220> FEATURE:
<223> OTHER INFORMATION: Synthetic

<400> SEQUENCE: 95

Tyr His Gly Tyr Trp Ala Leu Asp Tyr
1               5

<210> SEQ ID NO 96
<211> LENGTH: 11
<212> TYPE: PRT
<213> ORGANISM: Artificial Sequence
<220> FEATURE:
<223> OTHER INFORMATION: Synthetic

<400> SEQUENCE: 96

Lys Thr Ser Gln Asn Val Gly Thr Asn Val Ala
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Synthetic

<400> SEQUENCE: 97

Ser Thr Ser Tyr Arg Tyr Ser
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic

<400> SEQUENCE: 98

His Gln Tyr Phe Ser Tyr Pro Tyr Thr
1               5

<210> SEQ ID NO 99
<211> LENGTH: 118
<212> TYPE: PRT
<213> ORGANISM: Artificial Sequence
<220> FEATURE:
<223> OTHER INFORMATION: Synthetic

<400> SEQUENCE: 99

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Ile His Trp Val Arg Gln Ala Pro Gly Gln Gly Leu Glu Trp Met
        35                  40                  45

Gly Arg Ile Asp Pro Glu Asp Ala Glu Thr Lys Tyr Ala Pro Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Tyr His Gly Tyr Trp Ala Leu Asp Tyr Trp Gly Gln Gly Thr
            100                 105                 110

Leu Val Thr Val Ser Ser
        115
```

<210> SEQ ID NO 100
<211> LENGTH: 118
<212> TYPE: PRT
<213> ORGANISM: Artificial Sequence
<220> FEATURE:
<223> OTHER INFORMATION: Synthetic

<400> SEQUENCE: 100

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Ile His Trp Val Arg Gln Ala Pro Gly Gln Gly Leu Glu Trp Met
        35                  40                  45

Gly Arg Ile Asp Pro Glu Asp Ala Glu Thr Lys Tyr Ala Pro Lys Phe
    50                  55                  60

Gln Gly Arg Val Thr Met Thr Ala Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Tyr His Gly Tyr Trp Ala Leu Asp Tyr Trp Gly Gln Gly Thr
            100                 105                 110

Leu Val Thr Val Ser Ser
        115
```

<210> SEQ ID NO 101
<211> LENGTH: 118
<212> TYPE: PRT
<213> ORGANISM: Artificial Sequence
<220> FEATURE:
<223> OTHER INFORMATION: Synthetic

<400> SEQUENCE: 101

```
Gln Val Gln Leu Val Gln Ser Gly Ala Glu Val Lys Lys Pro Gly Ala
1               5                   10                  15
```

Ser Val Lys Leu Ser Cys Lys Ala Ser Gly Phe Asn Ile Lys Asp Tyr
            20                  25                  30

Tyr Ile His Trp Val Lys Gln Ala Pro Gly Gln Gly Leu Glu Trp Ile
            35                  40                  45

Gly Arg Ile Asp Pro Glu Asp Ala Glu Thr Lys Tyr Ala Pro Lys Phe
    50                  55                  60

Gln Gly Arg Val Thr Met Thr Ala Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Gly Arg Tyr His Gly Tyr Trp Ala Leu Asp Tyr Trp Gly Gln Gly Thr
            100                 105                 110

Leu Val Thr Val Ser Ser
            115

<210> SEQ ID NO 102
<211> LENGTH: 118
<212> TYPE: PRT
<213> ORGANISM: Artificial Sequence
<220> FEATURE:
<223> OTHER INFORMATION: Synthetic

<400> SEQUENCE: 102

Gln Val Gln Leu Val Gln Ser Gly Ala Glu Val Lys Lys Pro Gly Ala
1               5                   10                  15

Ser Val Lys Leu Ser Cys Lys Gly Ser Gly Phe Asn Ile Lys Asp Tyr
            20                  25                  30

Tyr Ile His Trp Val Lys Gln Ala Pro Gly Gln Gly Leu Glu Trp Ile
            35                  40                  45

Gly Arg Ile Asp Pro Glu Asp Ala Glu Thr Lys Tyr Ala Pro Lys Phe
    50                  55                  60

Gln Gly Arg Ala Thr Ile Thr Ala Asp Thr Ser Ile Ser Thr Ala Tyr
65                  70                  75                  80

Leu Glu Leu Ser Arg Leu Arg Ser Asp Asp Thr Val Val Tyr Tyr Cys
                85                  90                  95

Gly Arg Tyr His Gly Tyr Trp Ala Leu Asp Tyr Trp Gly Gln Gly Thr
            100                 105                 110

Leu Val Thr Val Ser Ser
            115

<210> SEQ ID NO 103
<211> LENGTH: 107
<212> TYPE: PRT
<213> ORGANISM: Artificial Sequence
<220> FEATURE:
<223> OTHER INFORMATION: Synthetic

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asn Val Gly Thr Asn
            20                  25                  30

Val Ala Trp Phe Gln Gln Lys Pro Gly Lys Ala Pro Lys Ser Leu Ile
            35                  40                  45

Tyr Ser Thr Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro 65                  70                  75                  80

Glu Asp Phe Ala Thr Tyr Tyr Cys His Gln Tyr Phe Ser Tyr Pro Tyr
                85                  90                  95

Thr Phe Gly Pro Gly Thr Lys Val Asp Ile Lys
            100                 105

<210> SEQ ID NO 104
<211> LENGTH: 107
<212> TYPE: PRT
<213> ORGANISM: Artificial Sequence
<220> FEATURE:
<223> OTHER INFORMATION: Synthetic

<400> SEQUENCE: 104

Asp Ile Gln Met Thr Gln Ser Pro Ser Ser Leu Ser Thr Ser Val Gly
1               5                   10                  15

Asp Arg Val Thr Ile Thr Cys Lys Thr Ser Gln Asn Val Gly Thr Asn
            20                  25                  30

Val Ala Trp Tyr Gln Gln Lys Pro Gly Lys Ala Pro Lys Pro Leu Ile
        35                  40                  45

Tyr Ser Thr Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Phe Ser Tyr Pro Tyr
                85                  90                  95

Thr Phe Gly Pro Gly Thr Lys Val Asp Ile Lys
            100                 105

<210> SEQ ID NO 105
<211> LENGTH: 107
<212> TYPE: PRT
<213> ORGANISM: Artificial Sequence
<220> FEATURE:
<223> OTHER INFORMATION: Synthetic

<400> SEQUENCE: 105

Asp Ile Gln Met Thr Gln Ser Pro Ser Ser Leu Ser Thr Ser Val Gly
1               5                   10                  15

Asp Arg Val Thr Ile Thr Cys Lys Thr Ser Gln Asn Val Gly Thr Asn
            20                  25                  30

Val Ala Trp Tyr Gln Gln Lys Pro Gly Lys Ala Pro Lys Pro Leu Ile
        35                  40                  45

Tyr Ser Thr Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys His Gln Tyr Phe Ser Tyr Pro Tyr
                85                  90                  95

Thr Phe Gly Pro Gly Thr Lys Leu Asp Ile Lys
            100                 105

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

```
Asp Ile Gln Met Thr Gln Ser Pro Ser Ser Leu Ser Thr Ser Val Gly
1               5                   10                  15

Asp Arg Val Thr Val Thr Cys Lys Thr Ser Gln Asn Val Gly Thr Asn
            20                  25                  30

Val Ala Trp Tyr Gln Gln Lys Pro Gly Lys Ala Pro Lys Pro Leu Ile
        35                  40                  45

Tyr Ser Thr Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Val Gln Pro
65              70                  75                  80

Glu Asp Phe Ala Thr Tyr Tyr Cys His Gln Tyr Phe Ser Tyr Pro Tyr
                85                  90                  95

Thr Phe Gly Pro Gly Thr Lys Leu Asp Ile Lys
                100                 105
```

<210> SEQ ID NO 107
<211> LENGTH: 17
<212> TYPE: PRT
<213> ORGANISM: Artificial Sequence
<220> FEATURE:
<223> OTHER INFORMATION: Synthetic

<400> SEQUENCE: 107

```
Arg Ile Asp Pro Asp Asp Gly Glu Thr Lys Tyr Ala Pro Lys Phe Gln
1               5                   10                  15

Gly
```

<210> SEQ ID NO 108
<211> LENGTH: 9
<212> TYPE: PRT
<213> ORGANISM: Artificial Sequence
<220> FEATURE:
<223> OTHER INFORMATION: Synthetic

<400> SEQUENCE: 108

```
Gly Gly Asn Tyr Tyr Val Met Asp Asn
1               5
```

<210> SEQ ID NO 109
<211> LENGTH: 11
<212> TYPE: PRT
<213> ORGANISM: Artificial Sequence
<220> FEATURE:
<223> OTHER INFORMATION: Synthetic

<400> SEQUENCE: 109

```
Lys Ala Ser Gln Asn Val Gly Thr Asn Val Ala
1               5                   10
```

<210> SEQ ID NO 110
<211> LENGTH: 7
<212> TYPE: PRT
<213> ORGANISM: Artificial Sequence
<220> FEATURE:
<223> OTHER INFORMATION: Synthetic

<400> SEQUENCE: 110

```
Thr Ala Ser Tyr Arg Tyr Ser
1               5
```

<210> SEQ ID NO 111
<211> LENGTH: 9

```
<212> TYPE: PRT
<213> ORGANISM: Artificial Sequence
<220> FEATURE:
<223> OTHER INFORMATION: Synthetic

<400> SEQUENCE: 111

Gln Gln Tyr Phe Ser Tyr Pro His Thr
1               5

<210> SEQ ID NO 112
<211> LENGTH: 5
<212> TYPE: PRT
<213> ORGANISM: Artificial Sequence
<220> FEATURE:
<223> OTHER INFORMATION: Synthetic

<400> SEQUENCE: 112

Asp Ser Tyr Met His
1               5

<210> SEQ ID NO 113
<211> LENGTH: 17
<212> TYPE: PRT
<213> ORGANISM: Artificial Sequence
<220> FEATURE:
<223> OTHER INFORMATION: Synthetic

<400> SEQUENCE: 113

Arg Ile Asp Pro Glu Asp Gly Glu Thr Asn Tyr Ala Pro Lys Phe Gln
1               5                   10                  15

Gly

<210> SEQ ID NO 114
<211> LENGTH: 10
<212> TYPE: PRT
<213> ORGANISM: Artificial Sequence
<220> FEATURE:
<223> OTHER INFORMATION: Synthetic

<400> SEQUENCE: 114

Arg Val Ser Ser Leu Tyr Ala Met Asp Tyr
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Synthetic

<400> SEQUENCE: 115

Leu Ala Ser Tyr Arg Tyr Ser
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic

<400> SEQUENCE: 116

Gln Gln Tyr Asn Asn Tyr Pro Trp Thr
1               5

<210> SEQ ID NO 117
```

```
<211> LENGTH: 7
<212> TYPE: PRT
<213> ORGANISM: Artificial Sequence
<220> FEATURE:
<223> OTHER INFORMATION: Synthetic

<400> SEQUENCE: 117

Ser Ala Ser Tyr Arg Tyr Ser
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic

<400> SEQUENCE: 118

Gln Gln Lys Asn Ser Tyr Pro Tyr Thr
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic

<400> SEQUENCE: 119

Gly Gly Asn Tyr Tyr Ala Met Asp Tyr
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic

<400> SEQUENCE: 120

Gln Gln His Asn Ser Tyr Thr Tyr Lys
1               5

<210> SEQ ID NO 121
<211> LENGTH: 17
<212> TYPE: PRT
<213> ORGANISM: Artificial Sequence
<220> FEATURE:
<223> OTHER INFORMATION: Synthetic

<400> SEQUENCE: 121

Arg Ile Asp Pro Glu Asp Gly Glu Thr Lys Tyr Ala Pro Lys Phe Gln
1               5                   10                  15

Asp

<210> SEQ ID NO 122
<211> LENGTH: 9
<212> TYPE: PRT
<213> ORGANISM: Artificial Sequence
<220> FEATURE:
<223> OTHER INFORMATION: Synthetic

<400> SEQUENCE: 122

Tyr Asp Gly Tyr Tyr Gly Phe Asp Tyr
1               5
```

```
<210> SEQ ID NO 123
<211> LENGTH: 9
<212> TYPE: PRT
<213> ORGANISM: Artificial Sequence
<220> FEATURE:
<223> OTHER INFORMATION: Synthetic

<400> SEQUENCE: 123

His Gln Tyr Asn Asn Tyr Pro Tyr Thr
1               5

<210> SEQ ID NO 124
<211> LENGTH: 5
<212> TYPE: PRT
<213> ORGANISM: Artificial Sequence
<220> FEATURE:
<223> OTHER INFORMATION: Synthetic

<400> SEQUENCE: 124

Asp Tyr Tyr Met Cys
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic

<400> SEQUENCE: 125

Ser Ala Thr Tyr Arg Tyr Ser
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic

<400> SEQUENCE: 126

Gln Gln His Asn Ser Tyr Ser Tyr Thr
1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic

<400> SEQUENCE: 127

Leu Gly Asn Trp Val Phe Asp Tyr
1               5

<210> SEQ ID NO 128
<211> LENGTH: 11
<212> TYPE: PRT
<213> ORGANISM: Artificial Sequence
<220> FEATURE:
<223> OTHER INFORMATION: Synthetic

<400> SEQUENCE: 128

Lys Ala Ser Gln Asn Val Gly Thr Asn Val Asp
1               5                   10

<210> SEQ ID NO 129
```

```
<211> LENGTH: 7
<212> TYPE: PRT
<213> ORGANISM: Artificial Sequence
<220> FEATURE:
<223> OTHER INFORMATION: Synthetic

<400> SEQUENCE: 129

Gln Gln Tyr Asn Thr Tyr Thr
1               5

<210> SEQ ID NO 130
<211> LENGTH: 17
<212> TYPE: PRT
<213> ORGANISM: Artificial Sequence
<220> FEATURE:
<223> OTHER INFORMATION: Synthetic

<400> SEQUENCE: 130

Arg Ile Asp Pro Glu Asp Gly Glu Thr Lys Tyr Ala Pro Lys Phe Gln
1               5                   10                  15

Val

<210> SEQ ID NO 131
<211> LENGTH: 9
<212> TYPE: PRT
<213> ORGANISM: Artificial Sequence
<220> FEATURE:
<223> OTHER INFORMATION: Synthetic

<400> SEQUENCE: 131

Gly Gly Asn Phe Tyr Tyr Phe Asp Tyr
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic

<400> SEQUENCE: 132

Gln Gln Cys Ile Asn Tyr Pro Tyr Thr
1               5

<210> SEQ ID NO 133
<211> LENGTH: 17
<212> TYPE: PRT
<213> ORGANISM: Artificial Sequence
<220> FEATURE:
<223> OTHER INFORMATION: Synthetic

<400> SEQUENCE: 133

Arg Ile Asp Pro Glu Asp Gly Glu Thr Lys Tyr Ala Pro Thr Phe Gln
1               5                   10                  15

Gly

<210> SEQ ID NO 134
<211> LENGTH: 9
<212> TYPE: PRT
<213> ORGANISM: Artificial Sequence
<220> FEATURE:
<223> OTHER INFORMATION: Synthetic

<400> SEQUENCE: 134

Tyr Asn Gly Tyr Ser Gly Phe Asp Tyr
1               5
```

<210> SEQ ID NO 135
<211> LENGTH: 9
<212> TYPE: PRT
<213> ORGANISM: Artificial Sequence
<220> FEATURE:
<223> OTHER INFORMATION: Synthetic

<400> SEQUENCE: 135

Gln Gln Tyr Asn Arg Tyr Pro Phe Thr
1               5

<210> SEQ ID NO 136
<211> LENGTH: 17
<212> TYPE: PRT
<213> ORGANISM: Artificial Sequence
<220> FEATURE:
<223> OTHER INFORMATION: Synthetic

<400> SEQUENCE: 136

Arg Ile Asp Pro Glu Asp Gly Glu Thr Lys Tyr Val Pro Lys Phe Gln
1               5                   10                  15

Gly

<210> SEQ ID NO 137
<211> LENGTH: 9
<212> TYPE: PRT
<213> ORGANISM: Artificial Sequence
<220> FEATURE:
<223> OTHER INFORMATION: Synthetic

<400> SEQUENCE: 137

Gly Gly Ser Tyr Tyr Val Met Asp Tyr
1               5

<210> SEQ ID NO 138
<211> LENGTH: 11
<212> TYPE: PRT
<213> ORGANISM: Artificial Sequence
<220> FEATURE:
<223> OTHER INFORMATION: Synthetic

<400> SEQUENCE: 138

Lys Ala Ser Gln Asn Val Gly Thr Ser Val Ala
1               5                   10

<210> SEQ ID NO 139
<211> LENGTH: 9
<212> TYPE: PRT
<213> ORGANISM: Artificial Sequence
<220> FEATURE:
<223> OTHER INFORMATION: Synthetic

<400> SEQUENCE: 139

Gln Gln Asp Asn Ser Tyr Pro His Thr
1               5

<210> SEQ ID NO 140
<211> LENGTH: 7
<212> TYPE: PRT
<213> ORGANISM: Artificial Sequence
<220> FEATURE:
<223> OTHER INFORMATION: Synthetic

<400> SEQUENCE: 140

Leu His Trp Ser Leu Asp Ser

```
1               5

<210> SEQ ID NO 141
<211> LENGTH: 11
<212> TYPE: PRT
<213> ORGANISM: Artificial Sequence
<220> FEATURE:
<223> OTHER INFORMATION: Synthetic

<400> SEQUENCE: 141

Lys Ala Ser Gln Asn Val Gly Thr Ala Val Ala
1               5                   10

<210> SEQ ID NO 142
<211> LENGTH: 7
<212> TYPE: PRT
<213> ORGANISM: Artificial Sequence
<220> FEATURE:
<223> OTHER INFORMATION: Synthetic

<400> SEQUENCE: 142

Ser Thr Ala Asn Arg Asp Thr
1               5

<210> SEQ ID NO 143
<211> LENGTH: 9
<212> TYPE: PRT
<213> ORGANISM: Artificial Sequence
<220> FEATURE:
<223> OTHER INFORMATION: Synthetic

<400> SEQUENCE: 143

Gln Gln Tyr Ser Ser Tyr Pro Tyr Thr
1               5

<210> SEQ ID NO 144
<211> LENGTH: 17
<212> TYPE: PRT
<213> ORGANISM: Artificial Sequence
<220> FEATURE:
<223> OTHER INFORMATION: Synthetic

<400> SEQUENCE: 144

Arg Val Asp Pro Glu Asp Gly Glu Thr Lys Tyr Val Pro Lys Phe Leu
1               5                   10                  15

Asp

<210> SEQ ID NO 145
<211> LENGTH: 9
<212> TYPE: PRT
<213> ORGANISM: Artificial Sequence
<220> FEATURE:
<223> OTHER INFORMATION: Synthetic

<400> SEQUENCE: 145

Gln Gln Cys Asn Asn Tyr Arg Leu Thr
1               5

<210> SEQ ID NO 146
<211> LENGTH: 5
<212> TYPE: PRT
<213> ORGANISM: Artificial Sequence
<220> FEATURE:
<223> OTHER INFORMATION: Synthetic

<400> SEQUENCE: 146
```

```
Asp Ser Tyr Ile His
1               5
```

<210> SEQ ID NO 147
<211> LENGTH: 10
<212> TYPE: PRT
<213> ORGANISM: Artificial Sequence
<220> FEATURE:
<223> OTHER INFORMATION: Synthetic

<400> SEQUENCE: 147

```
Trp Leu Ala Asp Tyr Ser Ala Met Asp Asn
1               5                   10
```

<210> SEQ ID NO 148
<211> LENGTH: 11
<212> TYPE: PRT
<213> ORGANISM: Artificial Sequence
<220> FEATURE:
<223> OTHER INFORMATION: Synthetic

<400> SEQUENCE: 148

```
Lys Ala Ser Glu Asp Ile Tyr Asn Arg Leu Ala
1               5                   10
```

<210> SEQ ID NO 149
<211> LENGTH: 7
<212> TYPE: PRT
<213> ORGANISM: Artificial Sequence
<220> FEATURE:
<223> OTHER INFORMATION: Synthetic

<400> SEQUENCE: 149

```
Gly Ala Thr Ser Leu Glu Thr
1               5
```

<210> SEQ ID NO 150
<211> LENGTH: 9
<212> TYPE: PRT
<213> ORGANISM: Artificial Sequence
<220> FEATURE:
<223> OTHER INFORMATION: Synthetic

<400> SEQUENCE: 150

```
Gln Gln Tyr Trp Asn Thr Leu Tyr Thr
1               5
```

<210> SEQ ID NO 151
<211> LENGTH: 10
<212> TYPE: PRT
<213> ORGANISM: Artificial Sequence
<220> FEATURE:
<223> OTHER INFORMATION: Synthetic

<400> SEQUENCE: 151

```
Arg Gly Ser Ser Leu Tyr Ala Val Asp Tyr
1               5                   10
```

<210> SEQ ID NO 152
<211> LENGTH: 7
<212> TYPE: PRT
<213> ORGANISM: Artificial Sequence
<220> FEATURE:
<223> OTHER INFORMATION: Synthetic

<400> SEQUENCE: 152

```
Leu Ala Ser Tyr Arg His Arg
```

```
1               5
```

<210> SEQ ID NO 153
<211> LENGTH: 9
<212> TYPE: PRT
<213> ORGANISM: Artificial Sequence
<220> FEATURE:
<223> OTHER INFORMATION: Synthetic

<400> SEQUENCE: 153

```
Gln Gln Phe Asn Ile Tyr Pro Trp Thr
1               5
```

<210> SEQ ID NO 154
<211> LENGTH: 5
<212> TYPE: PRT
<213> ORGANISM: Artificial Sequence
<220> FEATURE:
<223> OTHER INFORMATION: Synthetic

<400> SEQUENCE: 154

```
Asp Tyr Tyr Leu His
1               5
```

<210> SEQ ID NO 155
<211> LENGTH: 9
<212> TYPE: PRT
<213> ORGANISM: Artificial Sequence
<220> FEATURE:
<223> OTHER INFORMATION: Synthetic

<400> SEQUENCE: 155

```
Gly Gly Asn Tyr Asp Val Met Asp Tyr
1               5
```

<210> SEQ ID NO 156
<211> LENGTH: 11
<212> TYPE: PRT
<213> ORGANISM: Artificial Sequence
<220> FEATURE:
<223> OTHER INFORMATION: Synthetic

<400> SEQUENCE: 156

```
Lys Ala Ser Gln Asn Val Gly Thr Tyr Val Val
1               5                   10
```

<210> SEQ ID NO 157
<211> LENGTH: 9
<212> TYPE: PRT
<213> ORGANISM: Artificial Sequence
<220> FEATURE:
<223> OTHER INFORMATION: Synthetic

<400> SEQUENCE: 157

```
Gln Gln Lys Asn Thr Tyr Pro Phe Thr
1               5
```

<210> SEQ ID NO 158
<211> LENGTH: 9
<212> TYPE: PRT
<213> ORGANISM: Artificial Sequence
<220> FEATURE:
<223> OTHER INFORMATION: Synthetic

<400> SEQUENCE: 158

```
Gly Gly Asn Tyr Tyr Val Met Asp Tyr
1               5
```

<210> SEQ ID NO 159
<211> LENGTH: 11
<212> TYPE: PRT
<213> ORGANISM: Artificial Sequence
<220> FEATURE:
<223> OTHER INFORMATION: Synthetic

<400> SEQUENCE: 159

Lys Ala Ser Gln Asn Val Gly Thr Tyr Val Ala
1               5                   10

<210> SEQ ID NO 160
<211> LENGTH: 7
<212> TYPE: PRT
<213> ORGANISM: Artificial Sequence
<220> FEATURE:
<223> OTHER INFORMATION: Synthetic

<400> SEQUENCE: 160

Ser Ala Ser Tyr Arg Tyr Asn
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic

<400> SEQUENCE: 161

Gln Gln Tyr Asn Asn Tyr Pro Leu Thr
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic

<400> SEQUENCE: 162

Gly Gly Asn Phe Tyr Tyr Phe Asp Phe
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic

<400> SEQUENCE: 163

Gln Gln Cys Asn Ser Tyr Ser Tyr Thr
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic

<400> SEQUENCE: 164

Tyr Asp Gly Tyr Tyr Cys Phe Asp Tyr
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic

<400> SEQUENCE: 165

Gln Gln Tyr Asn Asn Tyr Pro Tyr Thr
1               5

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Asp Trp Gly His Ser Phe Asp Tyr
1               5

<210> SEQ ID NO 167
<211> LENGTH: 11
<212> TYPE: PRT
<213> ORGANISM: Artificial Sequence
<220> FEATURE:
<223> OTHER INFORMATION: Synthetic

<400> SEQUENCE: 167

Lys Ala Ser Gln Asn Val Gly Thr Thr Val Ala
1               5                   10

<210> SEQ ID NO 168
<211> LENGTH: 7
<212> TYPE: PRT
<213> ORGANISM: Artificial Sequence
<220> FEATURE:
<223> OTHER INFORMATION: Synthetic

<400> SEQUENCE: 168

Gln Gln Tyr Asn Ser Tyr Thr
1               5

<210> SEQ ID NO 169
<211> LENGTH: 10
<212> TYPE: PRT
<213> ORGANISM: Artificial Sequence
<220> FEATURE:
<223> OTHER INFORMATION: Synthetic

<400> SEQUENCE: 169

Glu Gly Ser Phe Thr Gly Trp Phe Pro Tyr
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Synthetic

<400> SEQUENCE: 170

Lys Ala Arg Gln Ser Val Gly Thr Tyr Val Ala
1               5                   10

-continued

```
<210> SEQ ID NO 171
<211> LENGTH: 7
<212> TYPE: PRT
<213> ORGANISM: Artificial Sequence
<220> FEATURE:
<223> OTHER INFORMATION: Synthetic

<400> SEQUENCE: 171

Ser Thr Ser Tyr Arg Tyr Asn
1               5

<210> SEQ ID NO 172
<211> LENGTH: 9
<212> TYPE: PRT
<213> ORGANISM: Artificial Sequence
<220> FEATURE:
<223> OTHER INFORMATION: Synthetic

<400> SEQUENCE: 172

Gln Gln Tyr His Ser Tyr Pro Tyr Thr
1               5

<210> SEQ ID NO 173
<211> LENGTH: 5
<212> TYPE: PRT
<213> ORGANISM: Artificial Sequence
<220> FEATURE:
<223> OTHER INFORMATION: Synthetic

<400> SEQUENCE: 173

Ser Asp Tyr Trp Asn
1               5

<210> SEQ ID NO 174
<211> LENGTH: 16
<212> TYPE: PRT
<213> ORGANISM: Artificial Sequence
<220> FEATURE:
<223> OTHER INFORMATION: Synthetic

<400> SEQUENCE: 174

Tyr Ile Ser Tyr Ser Gly Ser Ile Tyr Tyr Asn Pro Ser Leu Lys Ser
1               5                   10                  15

<210> SEQ ID NO 175
<211> LENGTH: 9
<212> TYPE: PRT
<213> ORGANISM: Artificial Sequence
<220> FEATURE:
<223> OTHER INFORMATION: Synthetic

<400> SEQUENCE: 175

Ser Gly Gly Met Tyr Tyr Phe Asp Tyr
1               5

<210> SEQ ID NO 176
<211> LENGTH: 11
<212> TYPE: PRT
<213> ORGANISM: Artificial Sequence
<220> FEATURE:
<223> OTHER INFORMATION: Synthetic

<400> SEQUENCE: 176

Arg Ala Ser Gly Asn Ile His Asn Tyr Leu Ala
1               5                   10

<210> SEQ ID NO 177
```

```
<211> LENGTH: 7
<212> TYPE: PRT
<213> ORGANISM: Artificial Sequence
<220> FEATURE:
<223> OTHER INFORMATION: Synthetic

<400> SEQUENCE: 177

Asn Ala Lys Thr Leu Glu Asp
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic

<400> SEQUENCE: 178

Gln His Phe Trp Ser Ile Pro Pro Thr
1               5

<210> SEQ ID NO 179
<211> LENGTH: 16
<212> TYPE: PRT
<213> ORGANISM: Artificial Sequence
<220> FEATURE:
<223> OTHER INFORMATION: Synthetic

<400> SEQUENCE: 179

Tyr Ile Ser Tyr Ser Gly Thr Ile Tyr Tyr Asn Pro Ser Leu Lys Ser
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: Synthetic

<400> SEQUENCE: 180

Tyr Ile Ser Tyr Ser Gly Asn Thr Asp Tyr Asn Pro Ser Leu Lys Ser
1               5                   10                  15

<210> SEQ ID NO 181
<211> LENGTH: 9
<212> TYPE: PRT
<213> ORGANISM: Artificial Sequence
<220> FEATURE:
<223> OTHER INFORMATION: Synthetic

<400> SEQUENCE: 181

Ser Glu Gly Met Tyr Phe Phe Asp Tyr
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic

<400> SEQUENCE: 182

Asn Ala Lys Thr Leu Ala Asp
1               5

<210> SEQ ID NO 183
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 183

Gln His Phe Trp Ser Thr Pro Pro Thr
1               5

<210> SEQ ID NO 184
<211> LENGTH: 9
<212> TYPE: PRT
<213> ORGANISM: Artificial Sequence
<220> FEATURE:
<223> OTHER INFORMATION: Synthetic

<400> SEQUENCE: 184

Phe Gly Gly Leu Thr Ala Met Asp Tyr
1               5

<210> SEQ ID NO 185
<211> LENGTH: 7
<212> TYPE: PRT
<213> ORGANISM: Artificial Sequence
<220> FEATURE:
<223> OTHER INFORMATION: Synthetic

<400> SEQUENCE: 185

Ala Thr Ser Tyr Arg Tyr Ser
1               5

<210> SEQ ID NO 186
<211> LENGTH: 5
<212> TYPE: PRT
<213> ORGANISM: Artificial Sequence
<220> FEATURE:
<223> OTHER INFORMATION: Synthetic

<400> SEQUENCE: 186

Asp Tyr Tyr Val His
1               5

<210> SEQ ID NO 187
<211> LENGTH: 9
<212> TYPE: PRT
<213> ORGANISM: Artificial Sequence
<220> FEATURE:
<223> OTHER INFORMATION: Synthetic

<400> SEQUENCE: 187

Phe Gly Gly Leu Asp Ala Met Asp Tyr
1               5

<210> SEQ ID NO 188
<211> LENGTH: 9
<212> TYPE: PRT
<213> ORGANISM: Artificial Sequence
<220> FEATURE:
<223> OTHER INFORMATION: Synthetic

<400> SEQUENCE: 188

Gln Gln Phe Asn Arg Tyr Pro Tyr Thr
1               5

<210> SEQ ID NO 189
<211> LENGTH: 5
<212> TYPE: PRT
```

```
<213> ORGANISM: Artificial Sequence
<220> FEATURE:
<223> OTHER INFORMATION: Synthetic

<400> SEQUENCE: 189

Ser His Phe Ile His
1               5

<210> SEQ ID NO 190
<211> LENGTH: 17
<212> TYPE: PRT
<213> ORGANISM: Artificial Sequence
<220> FEATURE:
<223> OTHER INFORMATION: Synthetic

<400> SEQUENCE: 190

Trp Ile Tyr Pro Gly Asp Asp Asp Thr Glu Tyr Asn His Lys Phe Asn
1               5                   10                  15
Gly

<210> SEQ ID NO 191
<211> LENGTH: 11
<212> TYPE: PRT
<213> ORGANISM: Artificial Sequence
<220> FEATURE:
<223> OTHER INFORMATION: Synthetic

<400> SEQUENCE: 191

Arg Val Glu Tyr Tyr Asn Gly Gly Phe Ala Tyr
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Synthetic

<400> SEQUENCE: 192

Lys Ala Ser Lys Asn Ile Arg Asn Asn Leu Gly
1               5                   10

<210> SEQ ID NO 193
<211> LENGTH: 7
<212> TYPE: PRT
<213> ORGANISM: Artificial Sequence
<220> FEATURE:
<223> OTHER INFORMATION: Synthetic

<400> SEQUENCE: 193

Ser Gly Ser Thr Leu Gln Ser
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic

<400> SEQUENCE: 194

Gln Gln Tyr Asp Gln Tyr Pro Leu Thr
1               5

<210> SEQ ID NO 195
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 195

Thr Tyr Gly Met Gly Val Gly
1               5

<210> SEQ ID NO 196
<211> LENGTH: 16
<212> TYPE: PRT
<213> ORGANISM: Artificial Sequence
<220> FEATURE:
<223> OTHER INFORMATION: Synthetic

<400> SEQUENCE: 196

Asn Ile Trp Trp Asp Asp Asp Lys Tyr Tyr Asn Pro Ser Leu Lys Asn
1               5                   10                  15

<210> SEQ ID NO 197
<211> LENGTH: 14
<212> TYPE: PRT
<213> ORGANISM: Artificial Sequence
<220> FEATURE:
<223> OTHER INFORMATION: Synthetic

<400> SEQUENCE: 197

His Pro Leu Pro Gly Tyr Lys Asp Asn Tyr Val Val Asp Ala
1               5                   10

<210> SEQ ID NO 198
<211> LENGTH: 16
<212> TYPE: PRT
<213> ORGANISM: Artificial Sequence
<220> FEATURE:
<223> OTHER INFORMATION: Synthetic

<400> SEQUENCE: 198

Arg Ser Ser Gln Ser Leu Glu Tyr Ser Asp Gln Tyr Thr Tyr Leu Glu
1               5                   10                  15

<210> SEQ ID NO 199
<211> LENGTH: 7
<212> TYPE: PRT
<213> ORGANISM: Artificial Sequence
<220> FEATURE:
<223> OTHER INFORMATION: Synthetic

<400> SEQUENCE: 199

Gly Val Ser Asn Arg Phe Ser
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic

<400> SEQUENCE: 200

Phe Gln Ala Thr His Asp Pro Tyr Thr
1               5

<210> SEQ ID NO 201
<211> LENGTH: 5
<212> TYPE: PRT
```

```
<213> ORGANISM: Artificial Sequence
<220> FEATURE:
<223> OTHER INFORMATION: Synthetic

<400> SEQUENCE: 201

Asp Cys Tyr Ile His
1               5

<210> SEQ ID NO 202
<211> LENGTH: 17
<212> TYPE: PRT
<213> ORGANISM: Artificial Sequence
<220> FEATURE:
<223> OTHER INFORMATION: Synthetic

<400> SEQUENCE: 202

Arg Ile Asp Pro Glu Asp Gly Glu Thr Lys Tyr Ala Pro Lys Phe Gln
1               5                   10                  15

Ala

<210> SEQ ID NO 203
<211> LENGTH: 9
<212> TYPE: PRT
<213> ORGANISM: Artificial Sequence
<220> FEATURE:
<223> OTHER INFORMATION: Synthetic

<400> SEQUENCE: 203

His Cys Asn Phe Leu Tyr Phe Asp Tyr
1               5

<210> SEQ ID NO 204
<211> LENGTH: 11
<212> TYPE: PRT
<213> ORGANISM: Artificial Sequence
<220> FEATURE:
<223> OTHER INFORMATION: Synthetic

<400> SEQUENCE: 204

Lys Ala Ser Gln Asn Val Gly Thr Ile Val Ala
1               5                   10

<210> SEQ ID NO 205
<211> LENGTH: 7
<212> TYPE: PRT
<213> ORGANISM: Artificial Sequence
<220> FEATURE:
<223> OTHER INFORMATION: Synthetic

<400> SEQUENCE: 205

Ser Ala Ser Tyr Arg Ser Ser
1               5

<210> SEQ ID NO 206
<211> LENGTH: 9
<212> TYPE: PRT
<213> ORGANISM: Artificial Sequence
<220> FEATURE:
<223> OTHER INFORMATION: Synthetic

<400> SEQUENCE: 206

Gln Gln Tyr Asn Asn Tyr Pro Val Ile
1               5
```

ANTI-IFNAR1 ANTIBODIES FOR TREATING AUTOIMMUNE DISEASES

The present invention claims the priority of the PCT/CN2018/106157, filed on Sep. 18, 2018, the contents of which are incorporated herein by its entirety.

This application is a U.S. National Stage Application under 35 U.S.C. 371 of International Application No. PCT/CN2019/106412, filed Sep. 18, 2019, which claims priority to International Application PCT/CN2018/106157, filed Sep. 18, 2018. The contents of each of the aforementioned are hereby incorporated by reference in their entirety into the present disclosure.

SEQUENCE LISTING

The instant application contains a Sequence Listing which has been filed electronically in ASCII format and is hereby incorporated by reference in its entirety. Said ASCII copy, created on Jun. 19, 2020, is named 271415US_SL.txt and is 102,221 bytes in size.

BACKGROUND

Systemic lupus erythematosus (SLE), also known simply as lupus, is an autoimmune disease in which the body's immune system mistakenly attacks healthy tissue in many parts of the body. Common symptoms include painful and swollen joints, fever, chest pain, hair loss, mouth ulcers, swollen lymph nodes, feeling tired, and a red rash which is most commonly on the face. Often there are periods of illness, called flares, and periods of remission during which there are few symptoms.

The cause of SLE is not clear. The mechanism involves an immune response by autoantibodies against a person's own tissues. These are most commonly anti-nuclear antibodies and they result in inflammation. There is no cure for SLE. Treatments may include NSAIDs, corticosteroids, immunosuppressants, hydroxychloroquine, and methotrexate. SLE significantly increases the risk of cardiovascular disease with this being the most common cause of death.

Type I IFNs, particularly the IFN-αs and IFN-β, have received attention for their roles in the pathogenesis of SLE and other autoimmune and inflammatory syndromes. By signaling through a common receptor (IFNAR), these pleiotropic cytokines affect almost every aspect of innate and adaptive immune responses, including upregulation of MHC and costimulatory molecules, and production of B cell survival factors (BAFF, April) by antigen-presenting cells, culminating in the engagement and expansion of autoreactive T and B cells. Of particular relevance to lupus pathogenesis is the induction of type I IFNs under sterile conditions through the engagement of endosomal Toll-like receptors (TLRs) by self-nucleic acids. There has been extensive interest in creating treatments based on blocking reagents against either the multiple IFN-αs and the single IFN-β, or their common receptor.

SUMMARY

The present disclosure provides antibodies or fragments thereof having binding specificity to the human interferon alpha and beta receptor subunit 1 (IFNAR1) protein, as well as bispecific antibodies having specificity to IFNAR1 and another antigen such as BAFF. These antibodies and fragments are useful in the treatment of autoimmune diseases such as systemic lupus erythematosus.

One embodiment of the present disclosure provides an antibody or fragment thereof having specificity to a human interferon alpha and beta receptor subunit 1 (IFNAR1) protein, wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein the HCDR1, HCDR2, HCDR3, LCDR1, LCDR2, and LCDR3 are selected from the group consisting of: (a) HCDR1: DYYMH (SEQ ID NO: 77), HCDR2: RIDPEDGETKYAPKFQG (SEQ ID NO: 78) or RIDPEDAETKYAPKFQG (SEQ ID NO:79), HCDR3: GGNFYVMDY (SEQ ID NO: 80), LCDR1: KASQNVGTNVV (SEQ ID NO: 81), LCDR2: SASYRVS (SEQ ID NO: 82), and LCDR3: QQKNNYPYT (SEQ ID NO: 83); and (b) HCDR1: DYYIH (SEQ ID NO: 92), HCDR2: RIDPEDGETKYAPKFQG (SEQ ID NO: 93) or RIDPEDAETKYAPKFQG (SEQ ID NO:94), HCDR3: YHGYWALDY (SEQ ID NO: 95), LCDR1: KTSQNVGTNVA (SEQ ID NO: 96), LCDR2: STSYRYS (SEQ ID NO: 97), and LCDR3: HQYFSYPYT (SEQ ID NO: 98).

In some embodiments, the HCDR1, HCDR2, HCDR3, LCDR1, LCDR2, and LCDR3 are HCDR1: DYYMH (SEQ ID NO: 77), HCDR2: RIDPEDAETKYAPKFQG (SEQ ID NO:79), HCDR3: GGNFYVMDY (SEQ ID NO: 80), LCDR1: KASQNVGTNVV (SEQ ID NO: 81), LCDR2: SASYRVS (SEQ ID NO: 82), and LCDR3: QQKNNYPYT (SEQ ID NO: 83).

In some embodiments, the antibody or fragment thereof comprises a heavy chain variable region comprising an amino acid sequence selected from the group consisting of SEQ ID NO: 7, and 84-87 (e.g., SEQ ID NO:85), or a peptide having at least 90% sequence identity to an amino acid sequence selected from the group consisting of SEQ ID NO: 7, and 84-87 (e.g., SEQ ID NO:85). In some embodiments, the antibody or fragment thereof comprises a light chain variable region comprising an amino acid sequence selected from the group consisting of SEQ ID NO: 8, and 88-91 (e.g., SEQ ID NO:88), or a peptide having at least 90% sequence identity to an amino acid sequence selected from the group consisting of SEQ ID NO: 8, and 88-91 (e.g., SEQ ID NO:88). The heavy chain variable region and the light chain variable, as recited here, include the CDR regions as recited above.

In some embodiments, the antibody or fragment thereof comprises a heavy chain variable region comprising the amino acid sequence of SEQ ID NO: 85, and a light chain variable region comprising the amino acid sequence of SEQ ID NO: 88.

In some embodiments, the HCDR1, HCDR2, HCDR3, LCDR1, LCDR2, and LCDR3 are HCDR1: DYYIH (SEQ ID NO: 92), HCDR2: RIDPEDAETKYAPKFQG (SEQ ID NO:94), HCDR3: YHGYWALDY (SEQ ID NO: 95), LCDR1: KTSQNVGTNVA (SEQ ID NO: 96), LCDR2: STSYRYS (SEQ ID NO: 97), and LCDR3: HQYFSYPYT (SEQ ID NO: 98).

In some embodiments, the antibody or fragment thereof comprises a heavy chain variable region comprising an amino acid sequence selected from the group consisting of SEQ ID NO: 73, and 99-102 (e.g., SEQ ID NO:100), or a peptide having at least 90% sequence identity to an amino acid sequence selected from the group consisting of SEQ ID NO: 73, and 99-102 (e.g., SEQ ID NO:100).

In some embodiments, the antibody or fragment thereof comprises a light chain variable region comprising an amino acid sequence selected from the group consisting of SEQ ID NO: 74, and 103-106 (e.g., SEQ ID NO:105), or a peptide having at least 90% sequence identity to an amino acid sequence selected from the group consisting of SEQ ID NO: 74, and 103-106 (e.g., SEQ ID NO:105).

In some embodiments, the antibody or fragment thereof comprises a heavy chain variable region comprising the amino acid sequence of SEQ ID NO: 100, and a light chain variable region comprising the amino acid sequence of SEQ ID NO: 105.

In another embodiments, provided is an antibody or fragment thereof having specificity to a human interferon alpha and beta receptor subunit 1 (IFNAR1) protein, wherein the antibody or fragment thereof can bind to one or more amino acid residues selected from the group consisting of H273, L274, Y275, K276, and K278 of the IFNAR1 protein.

In some embodiments, the antibody or fragment thereof of claim can bind to at least two of the amino acid residues selected from the group, such as K276, and K278. In some embodiments, the antibody or fragment thereof of claim can bind to at least three of the amino acid residues selected from the group, such as H273, K276, and K278; L274, K276, and K278; Y275, K276, and K278; or Y275, K276, and K278. In some embodiments, the antibody or fragment thereof of claim can bind to at least four, five or all of the amino acid residues selected from the group.

Also provided, in one embodiment, is a bifunctional molecule, comprising a first antigen-binding portion having specificity to a human interferon alpha and beta receptor subunit 1 (IFNAR1) protein and a second portion having specificity to a second protein, wherein the first antigen-binding portion comprises an antibody fragment of the present disclosure.

In some embodiments, the second portion comprises peptide edratide (hCDR1) or TACI-Ig. In some embodiments, the second portion is an antigen-binding fragment having specificity to a protein selected from the group consisting of BAFF, CD20, CD22, CTLA4, IL6, CXCL13 and C5. In some embodiments, the second portion is an antigen-binding fragment having specificity to a human B-cell-activating factor (BAFF) protein.

In some embodiments, the bifunctional molecule has a format comprising a full antibody fused to two single chain fragments (scFv) or to two Fab fragments (as illustrated as Format 1 herein). In some embodiments, the second portion comprises an antigen-binding fragment of Belimumab.

Uses and methods of the presently disclosed antibodies and fragments are also provided. For instance, the presently disclosed antibodies and fragments can be used for suppressing an immune response or treating an autoimmune disease or disorder in a patient in need thereof.

In some embodiments, the autoimmune disease or disorder is selected from the group consisting of type 1 diabetes, rheumatoid arthritis (RA), psoriasis/psoriatic arthritis, multiple sclerosis, systemic lupus erythematosus (lupus), inflammatory bowel disease, Addison's disease, Graves' disease, Sjögren's syndrome, Hashimoto's thyroiditis, myasthenia gravis, vasculitis, pernicious anemia, and celiac disease. In some embodiments, the autoimmune disease or disorder is systemic lupus erythematosus.

BRIEF DESCRIPTION OF THE DRAWINGS

FIG. 3 shows that 8G11H and 485G10H dose-dependently inhibited recombinant IFNα2b-induced secretion of IP-10 by normal PBMC culture.

DETAILED DESCRIPTION

Definitions

Figure 1A:
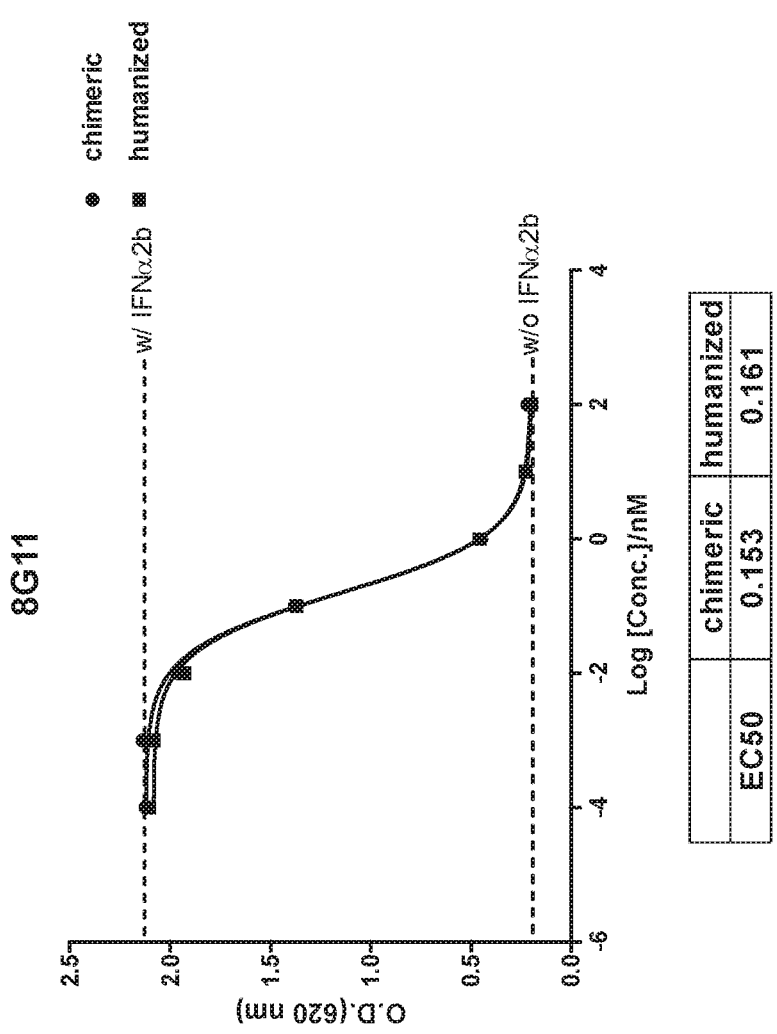
FIGS. 1A-B show that the 8G11H and 485G10H antibodies efficiently blocked IFNα2b-induced reporter gene expression, with potency comparable to that of the corresponding chimeric antibodies.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG$_1$, IgG$_2$, IgG$_3$, IgG$_4$, IgG$_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.*, 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-IFNAR1 Antibodies

The present disclosure provides antibodies, including bispecific antibodies and fragments, that have binding specificity to the human interferon alpha and beta receptor subunit 1 (IFNAR1) protein. As demonstrated in the experimental examples, numerous murine anti-human IFNAR1 antibodies were obtained, having high binding affinity to the human IFNAR1 protein. Two of the murine antibody clones, 8G11 and 485G10, were selected for further humanization and characterization. The humanized antibodies dose-dependently reversed IFNα2b-mediated inhibition of Daudi cell proliferation, IFNα2b-induced anti-viral function as well as efficiently inhibited the cell signal elicited by multiple type I IFNs at pM levels. The IFNs included IFNα 1, IFNα 2a, IFNα 4, IFNα 5, IFNα 6, IFNα 7, IFNα 8, IFNα 10, IFNα 14, IFNα 16, IFNα 17, and IFNα 21.

Additional functional studies showed that these antibodies efficiently inhibited IFNα2b-induced secretion of IP-10 by human PBMCs and inhibited IFNα-dependent or SLE plasma-mediated dendritic cell development as demonstrated by reduced cell surface markers CD38 and CD86 expression, and decreased production of IFN-γ by CD4+ T cells in MLR system.

Various formats of anti-IFNAR1/anti-BAFF bispecific antibodies were also prepared and tested for their binding capabilities and biological functions. These bispecific antibodies exhibited comparable binding activity to monospecific 8G11 in blocking IFNα2b signaling, and even better activity in blockade of BAFF-induced B cell proliferation.

In accordance with one embodiment of the present disclosure, provided are antibodies and fragments thereof that include the heavy chain and light chain variable domains with the CDR regions of the antibodies prepared in the experimental examples. The CDRs are summarized in Table A below.

TABLE A

CDR Sequences

| Antibody chain | CDR Sequences (CDR1, CDR2, CDR3 in order, for VH or VL) | SEQ ID NO: |
|---|---|---|
| 4A6-VH | DYYMH | 77 |
| | RIDPDDGETKYAPKFQG | 107 |
| | GGNYYVMDN | 108 |
| 4A6-VL | KASQNVGTNVA | 109 |
| | TASYRYS | 110 |
| | QQYFSYPHT | 111 |
| 4B12-VH | DSYMH | 112 |
| | RIDPEDGETNYAPKFQG | 113 |
| | RVSSLYAMDY | 114 |
| 4B12-VL | KASQNVGTNVA | 109 |
| | LASYRYS | 115 |
| | QQYNNYPWT | 116 |
| 4D8-VH | DYYMH | 77 |
| | RIDPEDAETKYAPKFQG | 79 |
| | GGNFYVMDY | 80 |
| 4D8-VL | KASQNVGTNVV | 81 |
| | SASYRYS | 117 |
| | QQKNSYPYT | 118 |
| 8G11-VH | DYYMH | 77 |
| | RIDPEDGETKYAPKFQG | 78 |
| | GGNFYVMDY | 80 |
| 8G11-VL | KASQNVGTNVV | 81 |
| | SASYRVS | 82 |
| | QQKNNYPYT | 83 |
| 12G11-VH | DYYMH | 77 |
| | RIDPEDGETKYAPKFQG | 78 |
| | GGNYYAMDY | 119 |
| 12G11-VL | KASQNVGTNVA | 109 |
| | SASYRYS | 117 |
| | QQHNSYTYK | 120 |
| 17F9-VH | DYYIH | 92 |
| | RIDPEDGETKYAPKFQD | 121 |
| | YDGYYGFDY | 122 |
| 17F9-VL | KASQNVGTNVA | 109 |
| | STSYRYS | 97 |
| | HQYNNYPYT | 123 |
| 18B6-VH | DYYMC | 124 |
| | RIDPEDGETKYAPKFQG | 78 |
| | GGNYYAMDY | 119 |
| 18B6-VL | KASQNVGTNVA | 109 |
| | SATYRYS | 125 |
| | QQHNSYSYT | 126 |
| 18C1-VH | DYYMH | 77 |
| | RIDPEDGETKYAPKFQG | 78 |
| | LGNWVFDY | 127 |
| 18C1-VL | KASQNVGTNVD | 128 |
| | SASYRYS | 117 |
| | QQYNTYT | 129 |
| 19B6-VH | DYYMH | 77 |
| | RIDPEDGETKYAPKFQV | 130 |
| | GGNFYYFDY | 131 |
| 19B6-VL | KASQNVGTNVA | 109 |
| | SASYRYS | 117 |
| | QQCINYPYT | 132 |
| 20B3-VH | DYYIH | 92 |
| | RIDPEDGETKYAPTFQG | 133 |
| | YNGYSGFDY | 134 |

TABLE A-continued

CDR Sequences

| Antibody chain | CDR Sequences (CDR1, CDR2, CDR3 in order, for VH or VL) | SEQ ID NO: |
| --- | --- | --- |
| 20B3-VL | KASQNVGTNVV<br>SASYRYS<br>QQYNRYPFT | 81<br>117<br>135 |
| 20E10-VH | DYYIH<br>RIDPEDGETKYAPKFQD<br>YDGYYGFDY | 92<br>121<br>122 |
| 20E10-VL | KASQNVGTNVA<br>STSYRYS<br>HQYNNYPYT | 109<br>97<br>123 |
| 20E12-VH | DYYMH<br>RIDPEDGETKYVPKFQG<br>GGSYYVMDY | 77<br>136<br>137 |
| 20E12-VL | KASQNVGTSVA<br>SASYRYS<br>QQDNSYPHT | 138<br>117<br>139 |
| 21D6-VH | DYYMH<br>RIDPEDGETKYAPKFQG<br>LHWSLDS | 77<br>78<br>140 |
| 21D6-VL | KASQNVGTAVA<br>STANRDT<br>QQYSSYPYT | 141<br>142<br>143 |
| 24F6-VH | DYYIH<br>RVDPEDGETKYVPKFLD<br>GGNYYAMDY | 92<br>144<br>119 |
| 24F6-VL | KASQNVGTNVA<br>LASYRYS<br>QQCNNYRLT | 109<br>115<br>145 |
| 29E12-VH | DYYIH<br>RIDPEDGETKYAPKFQD<br>YDGYYGFDY | 92<br>121<br>122 |
| 29E12-VL | KASQNVGTNVA<br>STSYRYS<br>HQYNNYPYT | 109<br>97<br>123 |
| 30B5-VH | DSYIH<br>RIDPEDGETKYAPKFQG<br>WLADYSAMDN | 146<br>78<br>147 |
| 30B5-VL | KASEDIYNRLA<br>GATSLET<br>QQYWNTLYT | 148<br>149<br>150 |
| 30C8-VH | DSYMH<br>RIDPEDGETKYAPKFQG<br>RGSSLYAVDY | 112<br>78<br>151 |
| 30C8-VL | KASQNVGTSVA<br>LASYRHR<br>QQFNIYPWT | 138<br>152<br>153 |
| 34H8-VH | DYYLH<br>RIDPEDGETKYAPKFQG<br>GGNYDVMDY | 154<br>78<br>155 |
| 34H8-VL | KASQNVGTYVV<br>SASYRYS<br>QQKNTYPFT | 156<br>117<br>157 |
| 36E3-VH | DSYMH<br>RIDPEDGETKYAPKFQG<br>RGSSLYAVDY | 112<br>78<br>151 |
| 36E3-VL | KASQNVGTSVA<br>LASYRHR<br>QQFNIYPWT | 138<br>152<br>153 |
| 39F5-VH | DYYIH<br>RIDPEDGETKYAPKFQV<br>GGNFYYFDY | 92<br>130<br>131 |
| 39F5-VL | KASQNVGTNVA<br>SASYRYS<br>QQCINYPYT | 109<br>117<br>132 |
| 41F1-VH | DYYMH<br>RIDPEDGETKYVPKFQG<br>GGNYYVMDY | 77<br>136<br>158 |
| 41F1-VL | KASQNVGTYVA<br>SASYRYN<br>QQYNNYPLT | 159<br>160<br>161 |
| 46A10-VH | DYYMH<br>RIDPEDGETKYAPKFQV<br>GGNFYYFDF | 77<br>130<br>162 |
| 46A10-VL | KASQNVGTNVA<br>SASYRYS<br>QQCINYPYT | 109<br>117<br>132 |
| 47C6-VH | DYYIH<br>RIDPEDGETKYAPKFQG<br>GGNFYYFDY | 92<br>78<br>131 |
| 47C6-VL | KASQNVGTNVA<br>SASYRYS<br>QQCNSYSYT | 109<br>117<br>163 |
| 47F5-VH | DYYMH<br>RIDPEDGETKYVPKFQG<br>GGSYYVMDY | 77<br>136<br>137 |
| 47F5-VL | KASQNVGTSVA<br>SASYRYS<br>QQDNSYPHT | 138<br>117<br>139 |
| 104A3-VH | DYYIH<br>RIDPEDGETKYAPKFQG<br>YDGYYCFDY | 92<br>78<br>164 |
| 104A3-VL | KASQNVGTNVA<br>STSYRYS<br>QQYNNYPYT | 109<br>97<br>165 |
| 106A7-VH | DYYMH<br>RIDPEDGETKYAPKFQG<br>DWGHSFDY | 77<br>78<br>166 |
| 106A7-VL | KASQNVGTTVA<br>SASYRYS<br>QQYNSYT | 167<br>117<br>168 |
| 107E12-VH | DYYIH<br>RIDPEDGETKYAPKFQD<br>EGSFTGWFPY | 92<br>121<br>169 |
| 107E12-VL | KARQSVGTYVA<br>STSYRYN<br>QQHSYPYT | 170<br>171<br>172 |
| 124D12-VH | DYYIH<br>RIDPEDGETKYAPKFQG<br>YDGYYCFDY | 92<br>78<br>164 |

TABLE A-continued

CDR Sequences

| Antibody chain | CDR Sequences (CDR1, CDR2, CDR3 in order, for VH or VL) | SEQ ID NO: |
|---|---|---|
| 124D12-VL | KASQNVGTNVA | 109 |
| | STSYRYS | 97 |
| | QQYNNYPYT | 165 |
| 260H8-VH | SDYWN | 173 |
| | YISYSGSIYYNPSLKS | 174 |
| | SGGMYYFDY | 175 |
| 260H8-VL | RASGNIHNYLA | 176 |
| | NAKTLED | 177 |
| | QHFWSIPPT | 178 |
| 268E9-VH | SDYWN | 173 |
| | YISYSGSIYYNPSLKS | 174 |
| | SGGMYYFDY | 175 |
| 268E9-VL | RASGNIHNYLA | 176 |
| | NAKTLED | 177 |
| | QHFWSIPPT | 178 |
| 269A7-VH | SDYWN | 173 |
| | YISYSGTIYYNPSLKS | 179 |
| | SGGMYYFDY | 175 |
| 269A7-VL | RASGNIHNYLA | 176 |
| | NAKTLED | 177 |
| | QHFWSIPPT | 178 |
| 293H10-VH | SDYWN | 173 |
| | YISYSGNTDYNPSLKS | 180 |
| | SEGMYFFDY | 181 |
| 293H10-VL | RASGNIHNYLA | 176 |
| | NAKTLAD | 182 |
| | QHFWSTPPT | 183 |
| 370E5-VH | DYYIH | 92 |
| | RIDPEDGETKYAPKFQG | 78 |
| | FGGLTAMDY | 184 |
| 370E5-VL | KASQNVGTNVA | 109 |
| | ATSYRYS | 185 |
| | QQYNNYPYT | 165 |
| 392D6-VH | DYYVH | 186 |
| | RIDPEDGETKYAPKFQG | 78 |
| | FGGLDAMDY | 187 |
| 392D6-VL | KASQNVGTNVA | 109 |
| | STSYRYN | 171 |
| | QQFNRYPYT | 188 |
| 402G3-VH | SHFIH | 189 |
| | WIYPGDDDTEYNHKFNG | 190 |
| | RVEYYNGGFAY | 191 |
| 402G3-VL | KASKNIRNNLG | 192 |
| | SGSTLQS | 193 |
| | QQYDQYPLT | 194 |
| 430H6-VH | TYGMGVG | 195 |
| | NIWWDDDKYYNPSLKN | 196 |
| | HPLPGYKDNYVVDA | 197 |
| 430H6-VL | RSSQSLEYSDQYTYLE | 198 |
| | GVSNRFS | 199 |
| | FQATHDPYT | 200 |
| 485G10-VH | DYYIH | 92 |
| | RIDPEDGETKYAPKFQG | 78 |
| | YHGYWALDY | 95 |

TABLE A-continued

CDR Sequences

| Antibody chain | CDR Sequences (CDR1, CDR2, CDR3 in order, for VH or VL) | SEQ ID NO: |
|---|---|---|
| 485G10-VL | KTSQNVGTNVA | 96 |
| | STSYRYS | 97 |
| | HQYFSYPYT | 98 |
| 487E3-VH | DCYIH | 201 |
| | RIDPEDGETKYAPKFQA | 202 |
| | HCNFLYFDY | 203 |
| 487E3-VL | KASQNVGTIVA | 204 |
| | SASYRSS | 205 |
| | QQYNNYPVI | 206 |

In some embodiments, the VH CDR1, CDR2, and CDR3 are selected from any set of VH CDR1, CDR2, and CDR3 shown in Table A, and the VL CDR1, CDR2, and CDR3 are selected from any set of VL CDR1, CDR2, and CDR3 shown in Table A. In some embodiments, the VH CDR1, CDR2, and CDR3 and the VL CDR1, CDR2, and CDR3 are selected from those derived from the same antibody in the examples.

In some embodiments, at least one, or two, or three, or four, or five, or six of the VH CDR1, CDR2, and CDR3 and the VL CDR1, CDR2, and CDR3 of the above are modified by one, two or three amino acid additions, deletions, substitutions, or the combinations thereof.

In one embodiment, the anti-IFNAR1 antibody or fragment thereof includes the following CDRs: HCDR1: DYYMH (SEQ ID NO: 77), HCDR2: RIDPEDGETKYAPKFQG (SEQ ID NO: 78), HCDR3: GGNFYVMDY (SEQ ID NO: 80), LCDR1: KASQNVGTNVV (SEQ ID NO: 81), LCDR2: SASYRVS (SEQ ID NO: 82), and LCDR3: QQKNNYPYT (SEQ ID NO: 83).

In one embodiment, one or more of the amino acid residues in the CDRs are substituted with a different amino acid to avoid post-translational modification. An example anti-IFNAR1 antibody or fragment thereof includes the following CDRs: HCDR1: DYYMH (SEQ ID NO: 77), HCDR2: RIDPEDAETKYAPKFQG (SEQ ID NO: 79), HCDR3: GGNFYVMDY (SEQ ID NO: 80), LCDR1: KASQNVGTNVV (SEQ ID NO: 81), LCDR2: SASYRVS (SEQ ID NO: 82), and LCDR3: QQKNNYPYT (SEQ ID NO: 83).

In some embodiments, the antibody is humanized but with one or more of the following back mutations on the heavy chain: 12V, 20L, 24G, 38K, 48I, 68A, 70I, 72A, 79A and 81L, according to Kabat numbering, and combinations thereof. In some embodiments, the antibody is humanized but with one or more of the following back mutations on the light chain: 4M, 13T, 21V, 43S, 46V, 74I, 78V and 87F according to Kabat numbering, and combinations thereof.

Non-limiting examples of heavy chain variable regions include SEQ ID NO: 7, and 84-87. Non-limiting example of light chain variable regions include SEQ ID NO: 8, and 88-91.

In some embodiments, the heavy chain variable region includes SEQ ID NO:85. In some embodiments, the light chain variable region includes SEQ ID NO:88.

In one embodiment, the anti-IFNAR1 antibody or fragment thereof includes the following CDRs: HCDR1: DYYIH (SEQ ID NO: 92), HCDR2: RIDPEDGETKYAPKFQG (SEQ ID NO: 93), HCDR3: YHGYWALDY (SEQ ID NO: 95), LCDR1: KTSQNVGTNVA (SEQ ID NO:

96), LCDR2: STSYRYS (SEQ ID NO: 97), and LCDR3: HQYFSYPYT (SEQ ID NO: C6).

In one embodiment, the anti-IFNAR1 antibody or fragment thereof includes the following CDRs: HCDR1: DYYIH (SEQ ID NO: 92), HCDR2: RIDPEDAETKYAPKFQG (SEQ ID NO:94), HCDR3: YHGYWALDY (SEQ ID NO: 95), LCDR1: KTSQNVGTNVA (SEQ ID NO: 96), LCDR2: STSYRYS (SEQ ID NO: 97), and LCDR3: HQYFSYPYT (SEQ ID NO: C6).

In some embodiments, the antibody is humanized but with one or more of the following back mutations on the heavy chain: 20L, 24G, 38K, 48I, 68A, 70I, 72A, 81L, and 97G, according to Kabat numbering, and combinations thereof. In some embodiments, the antibody is humanized but with one or more of the following back mutations on the light chain: 13T, 21V, 36Y, 46P, 78V, and 104L according to Kabat numbering, and combinations thereof.

Non-limiting examples of heavy chain variable regions include SEQ ID NO: 73, and 99-102.

Non-limiting example of light chain variable regions include SEQ ID NO: 74, and 103-106.

In some embodiments, the heavy chain variable region includes SEQ ID NO:100. In some embodiments, the light chain variable region includes SEQ ID NO:105.

It was an interesting discovery that the presently prepared antibodies target an epitope that is different from known anti-IFNAR1 antibody Anifrolumab. Accordingly, in one embodiment, provided is an antibody or fragment thereof having specificity to a human interferon alpha and beta receptor subunit 1 (IFNAR1) protein, wherein the antibody or fragment thereof can bind to one or more amino acid residues selected from the group consisting of H273, L274, Y275, K276, and K278 of the IFNAR1 protein.

In some embodiments, the antibody or fragment can bind to at least two of these epitope residues, such as H273 and L274, H273 and Y275, H273 and K276, H273 and K278, L274 and Y275, L274 and K276, L274 and K278, Y275 and K276, Y275 and K278, or K276 and K278.

In some embodiments, the antibody or fragment can bind to at least two of these epitope residues, such as H273, L274, and Y275; H273, L274, and K276; H273, L274, and K278; H273, Y275, and K276; H273, Y275, and K278; H273, K276, and K278; L274, Y275, and K276; L274, Y275, and K278; L274, K276, and K278; and Y275, K276, and K278.

In some embodiments, the antibody or fragment can bind to at least four of these epitope residues, such as L274, Y275, K276, and K278; H273, Y275, K276, and K278; H273, L274, K276, and K278; H273, L274, Y275, and K278; and H273, L274, Y275, and K276.

In some embodiments, the antibody or fragment can bind to all of these epitope residues.

The CDRs, heavy chain variable regions and light chain variable regions of the present disclosure can be further modified. In some embodiments, the modified heavy chain variable region or light chain variable region retains at least about 70%, 75%, 80%, 85%, 90%, 95%, 98% or 99% sequence identity and is still capable of binding to IFNAR1.

In some embodiments, the modification is substitution at no more than one hot spot position from each of the CDRs. In some embodiments, the modification is substitution at one, two or three such hot spot positions. In one embodiment, the modification is substitution at one of the hot spot positions. Such substitutions, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

Bi-Functional Molecules

It is contemplated that binding of both the IFNAR1 and another protein involved in the immune system would be advantageous or even synergistic. Accordingly, in some embodiments, bi-functional molecules are provided, such as a bispecific antibody with an anti-IFNAR1 fragment as disclosed herein and another antigen-binding fragment/portion.

The second portion of the bi-functional molecule may be any one of the following, (1) targeting B cells, including targeting B cell growth and survival factor such as anti-BAFF fragment, TACI-Ig; targeting surface molecules of B cells, such as anti-CD20 and anti-CD22 antibody fragments; (2) targeting co-stimulatory molecules, such as CTLA4-Ig and anti-CTLA4 antibody fragment; (3) targeting T cells, such as Edratide (hCDR1); and (4) targeting cytokines and complements, such anti-IL6, anti-CXCL13 and anti-05 antibody fragments.

In particular it is contemplated that the IFNAR1 and the BAFF (B-cell-activating factor) pathways can have synergistic effect in treating autoimmune diseases and disorders, such as lupus. Various formats of anti-IFNAR1/anti-BAFF bispecific antibodies (illustrated in FIG. 7) were tested for their binding capabilities and biological functions. Surprisingly, these bispecific antibodies exhibited comparable binding activity to monospecific 8G11 in blocking IFNα2b signaling, and even better activity in blockade of BAFF-induced B cell proliferation.

In one embodiment, therefore, provided is a bi-functional molecule having a first antigen-binding portion having specificity to a human interferon alpha and beta receptor subunit 1 (IFNAR1) protein and a second antigen-binding portion having specificity to a human B-cell-activating factor (BAFF) protein. The anti-IFNAR1 portion can a fragment of any embodiment of the present disclosure. The anti-BAFF portion can be a fragment from Belimumab (see, e.g., Dubey A K, et al., *Journal of Pharmacology & Pharmacotherapeutics*. 2011; 2(4):317-319).

Figure 7:
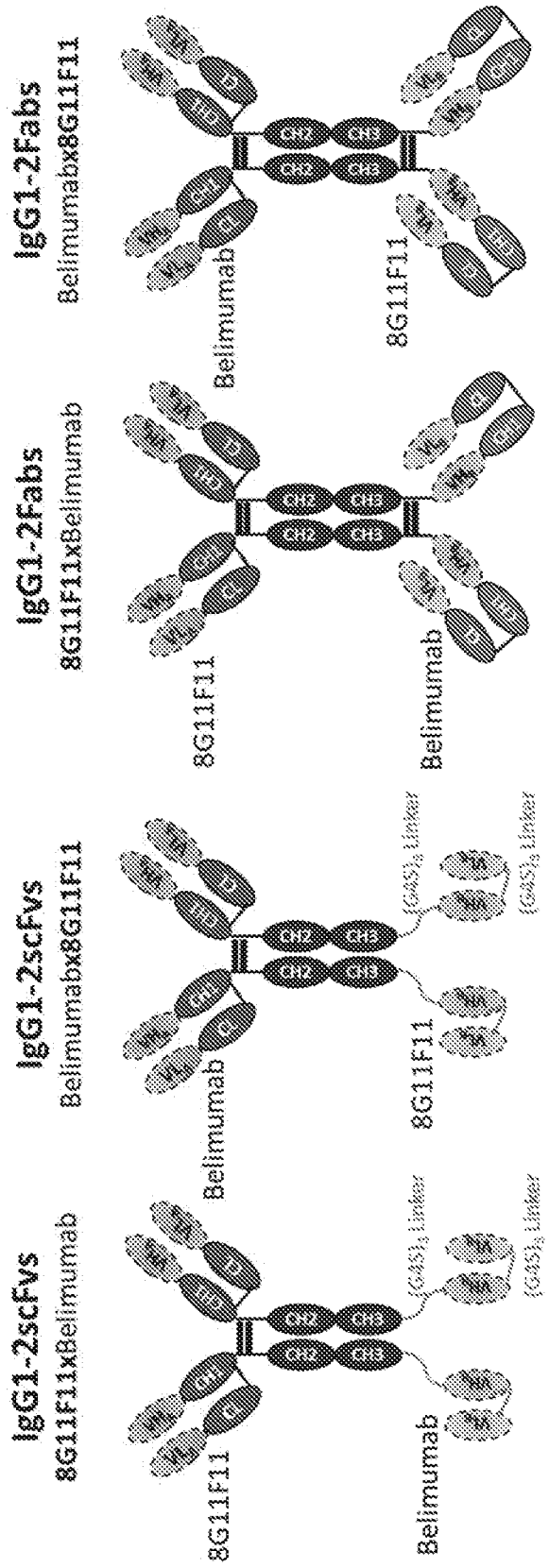
FIG. 7 depicts a schematic of designed four formats for the anti-IFNAR/BAFF bispecific antibody (Bi-BFINR).

The bi-functional molecule can take a format as illustrated in FIG. 7, e.g., having a full antibody fused to two single chain fragments (scFv) or to two Fab fragments. Other formats of bi-functional or bispecific molecules are also provided. In some embodiments, each of the anti-IFNAR1 and anti-BAFF fragments is independently selected from a Fab fragment, a single-chain variable fragment (scFv), or a single-domain antibody. In some embodiments, the bispecific antibody further includes a Fc fragment.

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Treatment and Diagnostic Methods

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

One embodiment provides a method of suppressing an immune response in a patient in need thereof. The method entails administering to the patient an antibody, fragment, or bi-functional molecule of the present disclosure. In some embodiments, the patient is a tissue or organ transplant recipient.

In some embodiments, a method of treating an autoimmune disease or disorder is provided. Non-limiting examples of autoimmune disease or disorder include type 1 diabetes, rheumatoid arthritis (RA), psoriasis/psoriatic arthritis, multiple sclerosis, systemic lupus erythematosus (lupus), inflammatory bowel disease, Addison's disease, Graves' disease, Sjögren's syndrome, Hashimoto's thyroiditis, myasthenia gravis, vasculitis, pernicious anemia, and celiac disease.

In a particular embodiments, the method is useful for treating systemic lupus erythematosus (lupus).

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

Methods of detecting expression of a human interferon alpha and beta receptor subunit 1 (IFNAR1) protein in a sample are also provided, in some embodiments, comprising contacting the sample with the antibody or fragment thereof, and detecting the binding which indicates expression of IFNAR1 in the sample.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1. Generation of Mouse Monoclonal Antibodies Against Human IFNAR-1

This example shows generation of anti-human-IFNAR-1 mouse monoclonal antibodies using the hybridoma technology.

Immunization

Recombinant human IFNAR-1 proteins containing the entire extracellular region of human IFNAR-1 were used as the immunogen to raise anti-human IFNAR-1 antibodies. C57BL/6, Balb/c, SJL mice or SD rats were first immunized subcutaneously (s.c.). with 50 μg immunogen and then immunized intraperitoneally (i.p.). or s.c. biweekly with 25 μg immunogen. Immune response was monitored by retroorbital bleeds. Plasma was screened by ELISA binding assay. In short, His-tagged IFNAR-1 was coated at 0.5 μg/ml overnight and then blocked by 5% BSA in PBS. Serial diluted sera were incubated with the coated antigen for 1 h at room temperature. The resulting plates were washed with PBS/T and incubated with goat anti-mouse IgG-HRP for 1 h at room temperature. The plates were developed with TMB substrate and analyzed by spectrophotometer at OD 450-630 nm. The mice with high titers of anti-IFNAR1 immunoglobulin were selected for fusion and further screening. Three days prior to sacrifice and removal of the spleens, the mice were final boosted i.p. with 25 antigen. The spleens were used for fusion.

Fusion and Hybridoma Screening

The mouse splenocytes, isolated from the mice, were fused with a mouse myeloma cell line based upon standard protocols. Single cell suspensions of splenic lymphocytes from immunized mice were fused to one-third the number of SP2/0 non secreting mouse myeloma cells with electrofusion machine. Cells were plated at approximately 1*10E5/well in flat bottom microtiter plate, followed by about 10 days incubation in selective medium containing 1*HAT, 10% fetal bovine serum, in DMEM. After 10 days, cells were cultured in medium in which the HAT was replaced with HT. Individual wells were then screened by ELISA for mouse anti-IFNAR-1 monoclonal IgG antibodies. The antibody secreting hybridomas were changed medium and screened again after 2 days. If still positive for mouse anti-IFNAR-1 antibodies, hybridoma were sub cloned twice by limiting dilution. The stable sub clones were then cultured in vitro to generate small amount of antibody in tissue culture medium for further characterization with various functional assays.

Clones showing strong blocking ability in IFN-responsive reporter assay were selected for sub cloning. Supernatants of 2-round sub clone were used to confirm ELISA-based human and rhesus IFNAR-1 binding and IFN alpha blocking ability, followed by sequencing and further analysis. After these screenings, 38 clones (4A6, 4B12, 4D8, 8G11, 12G11, 17F9, 18B6, 18C1, 19B6, 20B3, 20E10, 20E12, 21D6, 24F6, 29E12, 30B5, 30C8, 34H8, 36E3, 39F5, 41F1, 46A10, 47C6, 47F5, 104A3, 106A7, 107E12, 124D12, 260H8, 268E9, 269A7, 293H10, 370E5, 392D6, 402G3, 430H6, 485G10 and 487E3) were selected. Sequences of these clones are list in Table 1. Chimeric antibodies fused to human IgG1 Fc of these hybridoma were generated for further characterization.

TABLE 1

Antibody sequences selected from screening

| Antibody chain | Sequences* (CDR underlined and bold) | SEQ ID NO: |
|---|---|---|
| 4A6-VH | EVQLQQSGAELVKPGASVKLSCTASGFNIKDYYMHWVKQRTEQGLEWIGRIDPDDGETKYAPKFQGKATMTADTSSNTAYLQLGSLTSEDAAVYYCARGGNYYVMDNWGQGTSVTVSS | 1 |
| 4A6-VL | DIVMTQSQKFMSTSVGDRVSVTCKASQNVGTNVAWYQQKSGQSPKALIYTASYRYSGVPDRFTGSGSGTDFTLTISNLQSEDLADYLCQQYFSYPHTFGGGTKLEIK | 2 |
| 4B12-VH | EVQLQQSGAELVKPGASVKLSCTASGFNIKDSYMHWVKERTEQGLEWIGRIDPEDGETNYAPKFQGKATLTADTSSNTAYLQLSGLTSEDTAVYYCARRVSSLYAMDYWGQGTSVTVSS | 3 |
| 4B12-VL | DIVMTQSQKSMSTSVGDRVSVTCKASQNVGTNVAWYQQKPGQSPKPLIYLASYRYSGVPDRFTGSGSGTDFTLTISNVQSEDLAEYFCQQYNNYPWTFGGGTKLEIK | 4 |
| 4D8-VH | EVRLQQSGAELVQPGASVKLSCTGFGFNIKDYYMHWVKQRTEQGLEWIGRIDPEDAETKYAPKFQGQATITADTSSNTAYVQVSSLSSEDTAVYYCARGGNFYVMDYWGQGTSVTVSS | 5 |
| 4D8-VL | DIVMTQSQKFMSTSVGDRVSVTCKASQNVGTNVVWYQQKPGQSPKVLIYSASYRYSGVPDRFTGSGSGTDFTLIISNVQSEDLAEYFCQQKNSYPYTFGGGTKLEIK | 6 |
| 8G11-VH | EVQLQQSGAELVKPGASVKLSCTGFGFNIKDYYMHWVKQRAEQGLEWIGRIDPEDGETKYAPKFQGKATITADTSSNTAYLQVSSLTSEDTAVYYCARGGNFYVMDYWGQGTSVTVSS | 7 |
| 8G11-VL | DIVMTQSQKFMSTSVGDRVSVTCKASQNVGTNVVWYQQKPGQSPKVLIYSASYRVSGVPDRFTGSGSGTDFTLIISNVQSEDLAEYFCQQKNNYPYTFGGGTKLEIK | 8 |
| 12G11-VH | AVQLQQSGAELVKPGASVKLSCTASGFNIKDYYMHWVKQRTEQGLEWIGRIDPEDGETKYAPKFQGKATITADTSSNTAYLQLSSLTSEDTAVYYCARGGNYYAMDYWGQGTSVTVSS | 9 |
| 12G11-VL | DIVMTQSQKFMSTSVGDRVSVTCKASQNVGTNVAWYQQKPGQSPKALIYSASYRYSGVPDRFTGSGSGTDFTLTISNVQSEDLAEYFCQQHNSYTYKFGGGTKVEIK | 10 |
| 17F9-VH | EVQLLQSWADLVKPGASVKLSCTASGFNIKDYYIHWVKQRTEQGLEWIGRIDPEDGETKYAPKFQDKAAITADTSSNTAYLQLSSLTSEGTAVYYCARYDGYYGFDYWGQGTTLTVSS | 11 |
| 17F9-VL | DIVMTQSQKFMSTSVGDRVSVTCKASQNVGTNVAWYQQKPGQSPKPLIYSTSYRYSGVPDRFTGSGSGTDFTLTITNVQSEDLAEYFCHQYNNYPYTFGGGTKLEIK | 12 |
| 18B6-VH | EVQLQQSGAKLVKPGASVKLSCTASGFNIKDYYMCWVKQRTEQGLEWIGRIDPEDGETKYAPKFQGKATITADTSSNTASLQLSSL | 13 |

TABLE 1-continued

Antibody sequences selected from screening

| Antibody chain | Sequences* (CDR underlined and bold) | SEQ ID NO: |
|---|---|---|
| | TSEDTAVYYCARGG NYYAMDYWGQGTSVTVSS | |
| 18B6-VL | DTVMTQSQKFMSTSVGDRVSVTCKASQNVGTNVA WYQQKPGQSPKALIYS ATYRYSGVPDRFTGSGSGTDFTLTISNVQSEDLAEYF CQQHNSYSYTFGG GTKLEIK | 14 |
| 18C1-VH | EVQLQQSGAELVKPGASVKLSCTASGFNIKDYYMH WVKQRTEQGLEWIGR IDPEDGETKYAPKFQGKATITADTSSNTAYLQLSSL TSEDTAVYYCARLG NWVFDYWGQGTTLTVSS | 15 |
| 18C1-VL | DTVMTQSQKFMSTSVGDRVSVTCKASQNVGTNVD WYQQKSGQSPKALIYS ASYRYSGVPDRFTGSGSGTDFTLTISNVQSEDLAEYF CQQYNTYTFGGGT KLEIK | 16 |
| 19B6-VH | EVQLQQFGAELVKPGASVKLSCTASGFNIKDYYMH WVKQRTEQGLEWIGR IDPEDGETKYAPKFQVKATITADTSSNTAYLHFSSL TSEDTAVYYCVRGG NFYYFDYWGQGTTLTVSS | 17 |
| 19B6-VL | DIVMTQSQKFMSTSVGDRVSVTCKASQNVGTNVA WYQQKPGQSPKALIYS ASYRYSGVPDRFTGSGSGTDFTLTISNVQSEDLAEYF CQQCINYPYTFGG GTKLEIK | 18 |
| 20B3-VH | EVHLQQSGAELVKPGTSLKLSCTASGFNIKDYYIHW VKQRTEQGLEWIGR IDPEDGETKYAPTFQGKATITADTSSNTAYLQLSSL TSEDTAVYYCARYN GYSGFDYWGQGTTLTVSS | 19 |
| 20B3-VL | DIVMTQSQKFMSTSEGDRVSVTCKASQNVGTNVV WYQQKPGQSPKALIYS ASYRYSGVPDRFTGSGSGTDFTLTISNVQSEDLAEYF CQQYNRYPFTFGA GTKLELK | 20 |
| 20E10-VH | EVQLLQSWADLVKPGASVKLSCTASGFNIKDYYIH WVKQRTEQGLEWIGR IDPEDGETKYAPKFQDKAAITADTSSNTAYLQLSSL TSEGTAVYYCARYD GYYGFDYWGQGTTLTVSS | 21 |
| 20E10-VL | DIVMTQSQKFMSTSVGDRVSVTCKASQNVGTNVA WYQQKPGQSPKPLIYS TSYRYSGVPDRFTGSGSGTDFTLTITNVQSEDLAEYF CHQYNNYPYTFGG GTKLEIK | 22 |
| 20E12-VH | EVQLQQSGAEVVKPGASVKLSCTASGFNIKDYYMH WVKQRTEQGLECIGR IDPEDGETKYVPKFQGKATITAETSSNTAYLQLSSL TAEDTAVYYCSRGG SYYVMDYWGQGTSVTVSS | 23 |
| 20E12-VL | DVVMTQSRKFMSTSVGDRVSVTCKASQNVGTSVA WYQQKLGQSPKALIYS ASYRYSGVPDRFTGSGSGTDFTLTISNVQSEDLAEYF CQQDNSYPHTFGG GTKLEIK | 24 |
| 21D6-VH | EVQLQQSGAELVKPGASVKLSCTASGFNIKDYYMH WVKQRTEQGLEWIGR IDPEDGETKYAPKFQGKATITADTSSNTAYLQLSSL TSEDTAVYYCTSLH WSLDSWGQGTTLTVSS | 25 |

TABLE 1-continued

Antibody sequences selected from screening

| Antibody chain | Sequences* (CDR underlined and bold) | SEQ ID NO: |
| --- | --- | --- |
| 21D6-VL | DIVMTQSQKFMSTTVGDRVSITCKASQNVGTAVAW YQQQPGQSPKPLIYS TANRDTGVPDRFTGSGSGTDFTLTISNMQSEDLAHY FCQQYSSYPYTFGG GTKLEIK | 26 |
| 24F6-VH | DVQLQQSGAELVKPGASVNLSCTGSGFNIKDYYIH WVKQRTEQGLEWIGR VDPEDGETKYVPKFLDKATITADTSSNTAYLQLSSL TSEDTAVYYCTRGG NYYAMDYWGQGTSVTVSS | 27 |
| 24F6-VL | DIVMTQSQKFMSTSVGDRVSVTCKASQNVGTNVA WYQQKSGQSPKALIFL ASYRYSGVPDRFTGSGSGTDFTLTISNVQSEDLAEYF CQQCNNYRLTFGS GTKLEIK | 28 |
| 29E12-VH | EVQLLQSWADLVKPGASVKLSCTASGFNIKDYYIH WVKQRTEQGLEWIGR IDPEDGETKYAPKFQDKAAITADTSSNTAYLQLSSL TSEGTAVYYCARYD GYYGFDYWGQGTTLTVSS | 29 |
| 29E12-VL | DIVMTQSQKFMSTSVGDRVSVTCKASQNVGTNVA WYQQKPGQSPKPLIYS TSYRYSGVPDRFTGSGSGTDFTLTITNVQSEDLAEYF CHQYNNYPYTFGG GTKLEIK | 30 |
| 30B5-VH | EAQLQQSGAELVKPGASVKLSCTASGFNIRDSYIHW VNQRTEQGLEWIGR IDPEDGETKYAPKFQGKATMTADTSSNTAYLQLSS LTSEDTAVYYCASWL ADYSAMDNWGQGTSVTVSS | 31 |
| 30B5-VL | DIQMTQSSSSFSVSLGDRVTITCKASEDIYNRLAWY QQKPGNAPRLLISG ATSLETGVPSRFSGSGSGKDYTLSITSLQTEDVATYY CQQYWNTLYTFGG GTKLEMK | 32 |
| 30C8-VH | EVQLQQSGAELVKPGASVKLSCTSSGFNIKDSYMH WVKQRTEQGLEWIGR IDPEDGETKYAPKFQGKATITADTSSNTAYLQLNSL TSEDTAVYYCARRG SSLYAVDYWGQGTSVTVSS | 33 |
| 30C8-VL | DIVMTQSQKFMSTSVGDRVSVTCKASQNVGTSVA WYQQKPGQSPKAVIYL ASYRHRGVPARFTGSGSGTDFTLTISNVQSEDLAEY FCQQFNIYPWTFGG GTKLEIK | 34 |
| 34H8-VH | EVQLLQSGAELVKPGASVRLSCTASGFNIKDYYLH WVKQRTEQGLEWIGR IDPEDGETKYAPKFQGKATITTDTSSNTAYLQLSSL TSEDTAVYYCTRGG NYDVMDYWGQGTSVTVSS | 35 |
| 34H8-VL | DIVMTQSQKFMSTSVGDRVSVTCKASQNVGTYVV WYQQKPGQSPKALIYS ASYRYSGVPDRFTGSGSGTDFTLTIGNVQSEDLAEYF CQQKNTYPFTFGG GTKLEIE | 36 |
| 36E3-VH | EVQLQQSGAELVKPGASVKLSCTSSGFNIKDSYMH WVKQRTEQGLEWIGR IDPEDGETKYAPKFQGKATITADTSSNTAYLQLNSL TSEDTAVYYCARRG SSLYAVDYWGQGTSVTVSS | 37 |
| 36E3-VL | DIVMTQSQKFMSTSVGDRVSVTCKASQNVGTSVA WYQQKPGQSPKAVIYL ASYRHRGVPARFTGSGSGTDFTLTISNVQSEDLAEY | 38 |

TABLE 1-continued

Antibody sequences selected from screening

| Antibody chain | Sequences* (CDR underlined and bold) | SEQ ID NO: |
|---|---|---|
| | FCQQFNIYPWTFGG<br>GTKLEIK | |
| 39F5-VH | EVQLQQSGADLVRPGASVKLSCTASGFNIKDYYIHW<br>VKQRTEQGLEWIGR<br>IDPEDGETKYAPKFQVKTTITADTSSNTAYLQFSSL<br>TSEDTAVYYCVRGG<br>NFYYFDYWGQGSTLTVSS | 39 |
| 39F5-VL | DIVMTQSQKFMSTSVGDRVSVTCKASQNVGTNVA<br>WYQQKPGQSPKALIYS<br>ASYRYSGVPDRFTGSGSGTDFTLTISNVQSEDLAEYF<br>CQQCINYPYTFGG<br>GTKLEIK | 40 |
| 41F1-VH | EVQLQQSGAELVKSGASVRLSCTASGFNIKDYYMH<br>WVKQRTEKGLEWIGR<br>IDPEDGETKYVPKFQGKATITADTSSNTVYLQLNSL<br>TSEDTAVYYCVRGG<br>NYYVMDYWGQGTSVTVSS | 41 |
| 41F1-VL | DIVMTQSQKFMSTSVGDRVSVTCKASQNVGTYVA<br>WYQQKPGQSPKVVIYS<br>ASYRYNGVPDRFTGSGSGTDFTLTISNVQPEDLAEYF<br>CQQYNNYPLTFGS<br>GTKLEIK | 42 |
| 46A10-VH | EVQLQQSGAELVKPGASVKLSCTASGFNIKDYYMH<br>WVKQRTEQGLELIGR<br>IDPEDGETKYAPKFQVKATITADASSNTAYLQFSSL<br>TSEDAAVYYCVRGG<br>NFYYFDFWGQGTTLTVSS | 43 |
| 46A10-VL | DIVMTQSQKFMSTSVGDRVSVTCKASQNVGTNVA<br>WYQQKPGQSPKALVYS<br>ASYRYSGVPDRFTGSGSGTDFTLTISDVQSEDLAEYF<br>CQQCINYPYTFGG<br>GTKLEIK | 44 |
| 47C6-VH | EVQLQQSGAELVKPGASVKLSCTASGFNIKDYYIHW<br>VKQRTEQGLEWIGR<br>IDPEDGETKYAPKFQGKATITADTSSNTAYLHLSSL<br>TSEDTAVYYCSRGG<br>NFYYFDYWGQGTSLTVSS | 45 |
| 47C6-VL | DIVMTQSQKFMSTLVGDRVSVTCKASQNVGTNVA<br>WYQQKPGQSPKALIYS<br>ASYRYSGVPDRFTGSGSGTDFTLTISNVQSEDLAEYF<br>CQQCNSYSYTFGG<br>GTKLEIK | 46 |
| 47F5-VH | EVQLQQSGAEVVKPGASVKLSCTASGFNIKDYYMH<br>WVKQRTEQGLECIGR<br>IDPEDGETKYVPKFQGKATITAETSSNTAYLQLSSL<br>TAEDTAVYYCSRGG<br>SYYVMDYWGQGTSVTVSS | 47 |
| 47F5-VL | DVVMTQSRKFMSTSVGDRVSVTCKASQNVGTSVA<br>WYQQKLGQSPKALIYS<br>ASYRYSGVPDRFTGSGSGTDFTLTISNVQSEDLAEYF<br>CQQDNSYPHTFGG<br>GTKLEIK | 48 |
| 104A3-VH | EVQLQQSGAELVKPGASVKVSCTGSGFNIKDYYIH<br>WVKQRTEQGLEWIGR<br>IDPEDGETKYAPKFQGKATITSDTSSNTAYLQLSSL<br>TSGDTAVYFCARYD<br>GYYCFDYWGQGTTLTVSS | 49 |
| 104A3-VL | DIVMTQSQKFMSTSVGDRVSVTCKASQNVGTNVA<br>WYQQKPGQSPKPLIYS<br>TSYRYSGVPDRFTGSGSGTDFTLTISNVQSADLAAYF<br>CQQYNNYPYTFGG<br>GTRLEIK | 50 |

TABLE 1-continued

Antibody sequences selected from screening

| Antibody chain | Sequences* (CDR underlined and bold) | SEQ ID NO: |
|---|---|---|
| 106A7-VH | EVQLQQSGADLVKPGASVKLSCTTSGFNIKDYYMHWVNQRTEQGLEWIGR IDPEDGETKYAPKFQGKATITADTSSNTAYLQLSSLTSEDTAVYYCARDW GHSFDYWGQGTTLTVSS | 51 |
| 106A7-VL | DIVMTQSQKFMSTSVGDRVSVTCKASQNVGTTVAWYQQKPGQSPKTLIYS ASYRSGVPDRFTGSGSGTDFTLTISNVQSEDLAEYFCQQYNSYTFGGGT KLEMK | 52 |
| 107E12-VH | EVQLQQSGAEFVKPGASVKLSCTASGFNIKDYYIHWVTQKTEQGLEWIGR IDPEDGETKYAPKFQDKATITADSSSNTAYLQLSSLTSVDTAVYFCSREG SFTGWFPYWGQGTLVSVSA | 53 |
| 370E5-VL | DIVMTQSQKFMSTSVGDRVSVTCKARQSVGTYVAWYQQKPGQSPKALIYS TSYRNGVPDRFTGSGSGTDFTLTISNVQSEDLADYFCQQYHSYPYTFGG GTKLEIK | 54 |
| 124D12-VH | EVQLQQSGAELVKPGASVKVSCTGSGFNIKDYYIHWVKQRTEQGLEWIGR IDPEDGETKYAPKFQGRATITSDTSSNTAYLQLSSLTSGDTAVYYCARYD GYYCFDYWGQGTTLTVSS | 55 |
| 124D12-VL | DIVMTQSQKFMSTSVGDRVSVTCKASQNVGTNVAWYQQKPGQSPKPLIYS TSYRSGVPDRFTGSGSGTDFTLTISNVQSADLAAYFCQQYNNYPYTFGG GTRLEIK | 56 |
| 260H8-VH | EVQLQESGPGLAKPSQTLSLTCSVTGYSITSDYWNWIRKFPGNKLEYMGY ISYSGSIYYNPSLKSRISITRDTSKNQYYLQLNSVTNEDTATYYCARSGG MYYFDYWGQGTTLTVSS | 57 |
| 260H8-VL | DIQMTQSPASLSASVGETVTITCRASGNIHNYLAWYQQKQGKSPQLLVYN AKTLEDGVPSRFSGSGSGTQYSLKINSLQPEDFGSYYCQHFWSIPPTFGS GTKLEIK | 58 |
| 268E9-VH | EVQLQESGPGLAKPSQTLSLTCSVTGYSITSDYWNWIRKFPGNKLEYMGY ISYSGSIYYNPSLKSRISITRATSKNQYYLQLNSVTNEDTATYYCARSGG MYYFDYWGQGTTLTVSS | 59 |
| 268E9-VL | DIQMTQSPASLSASVGETVTITCRASGNIHNYLAWYQQKQGKSPQLLVYN AKTLEDGVPSRFSGSGSGTQYSLKINSLQPEDFGSYYCQHFWSIPPTFGS GTKLEIK | 60 |
| 269A7-VH | EVQLQESGPGLAKPSQTLSLTCSVTGYSITSDYWNWIRKFPGNKLEYMGY ISYSGTIYYNPSLKSRISITRDTSKNQYYLQLNSVTNEDTATYYCARSGG MYYFDYWGQGTTLTVSS | 61 |
| 269A7-VL | DIQMTQSPASLSASVGETVTITCRASGNIHNYLAWYQQKQGKSPQLLVYN AKTLEDGVPSRFSGSGSGTQYSLKINSLQPEDFGSYYCQHFWSIPPTFGS GTKLEIK | 62 |
| 293H10-VH | EVQLQESGPGLAKPSQTLSLTCSVTGYSITSDYWNWIRKFPGNKLEYMGY ISYSGNTDYNPSLKSRFSITRDTSKNQFYLQLNSVTT | 63 |

TABLE 1-continued

Antibody sequences selected from screening

| Antibody chain | Sequences* (CDR underlined and bold) | SEQ ID NO: |
|---|---|---|
| | EDTATYYCARSEG MYFFDYWGQGTTLTVSS | |
| 293H10-VL | DIQMTQSPASLSASVGETVSITCRASGNIHNYLAWYHQKQGKSPQLLVYN AKTLADGVPSRFSGSGSGTQYSLKINSLQPEDFGSYYCQHFWSTPPTFGSGTKLEIK | 64 |
| 370E5-VH | EVQLQQSGAELVKPGASVKLSCTASGFNIKDYYIHWVKQRTEQGLEWIGR IDPEDGETKYAPKFQGKATITADTSSNTAYLQLSSLTSEDTAVYYCARFG GLTAMDYWGQGTSVTVSS | 65 |
| 370E5-VL | DIVMTQSQKFMSTSVGDRVSVTCKASQNVGTNVAWYQQKPGQSPKALIYA TSYRYSGVPDRFTGSGSGTDFTLTISNVQSEDLAEYFCQQYNNYPYTFGGGTKLEIK | 66 |
| 392D6-VH | AVQLQQSGTELVKPGASVKLSCSASGFNIKDYYVHWVKQKTEQGLEWIGR IDPEDGETKYAPKFQGKATVTADTSSNTAYMQLSSLTSEDTAVYYCTRFG GLDAMDYWGQGTSVTVSS | 67 |
| 392D6-VL | DIVMTQSQKFMSTSVGDRVSVTCKASQNVGTNVAWYQQKPGQSPKPLIYS TSYRYNGVPDRFTGSGSGTEFTLTISNVQSEDLAEYFCQQFNRYPYTFGGGTKLEIK | 68 |
| 402G3-VH | QVQLQQSGAELVKPGSSVKISCKASGFTFTSHFIHWIKQQPGNGLKWIGW IYPGDDDTEYNHKFNGKATLTADKSSSTAYMHLSSLTSEDSAVYFCARRV EYYNGGFAYWGQGTLVTVSS | 69 |
| 402G3-VL | DVQMTQSPSYLAAPPGESVSISCKASKNIRNNLGWYQERPGKTPNLLIHS GSTLQSGAPSRFSGGGSGTDFTLTIRSLESEDSAVYYCQQYDQYPLTFGSGTKLEIK | 70 |
| 430H6-VH | QVTLKESGPGILQPSQTLSLTCTFSGFSLNTYGMGV GWIRQPSGKGLEWLA NIWWDDDKYYNPSLKNRLTISKDTSNNQAFLKITNVDTADTATYFCARH PLPGYKDNYVVDAWGQGASVTVSS | 71 |
| 430H6-VL | DVVLTQTPGSLSVTLGDQASISCRSSQSLEYSDQYT YLEWYLQKSGQSPQLLIYGVSNRFSGVPDRFIGSGSGTDFTLKISRVEPEDLGVYYCFQATHDP YTFGAGTKLELK | 72 |
| 485G10-VH | EVQLQQSGAELVKPGASVKLSCTGSGFNIKDYYIHWVKQRTEQGLEWIGR IDPEDGETKYAPKFQGKATITADTSSNTAYLQLSSLTSEDTVVYYCGRYH GYWALDYWGQGTSVTVSS | 73 |
| 485G10-VL | DIVMTQSQKFMSTSVGDRVSVTCKTSQNVGTNVAWYQQKPGQSPKPLIYS TSYRYSGVPDRFTGSGSGTDFTLIISNVQSEDLAEYFCHQYFSYPYTFGGGTLLEIK | 74 |
| 487E3-VH | EVQLQQSGAELVKPGASVKLSCSASGFNIKDCYIHWVKQRTEQGLEWIGR IDPEDGETKYAPKFQAKATITADTSSNTAYLQLNSLTSEDTAVYYCARHC NFLYFDYWGQGSTLTVS | 75 |

TABLE 1-continued

Antibody sequences selected from screening

| Antibody chain | Sequences* (CDR underlined and bold) | SEQ ID NO: |
|---|---|---|
| 487E3-VL | DIVMTQSQKSMSTSLGDRVTVTCKASQNVGTIVAWYQLKPGQSPKTLIYSASYRSSGVPDRFTGSGSGTDFTLTISNVQSEDLAEYFCQQYNNYPVIFGSGTKLEIR | 76 |

Example 2. Binding Properties of Anti-IFNAR-1 Mouse Monoclonal Antibodies

This example tested the binding properties of the anti-IFNAR-1 mouse antibodies to the human IFNAR-1 proteins by ELISA assay. In short, His-tagged IFNAR-1 was coated at 0.5 µg/ml overnight and then blocked by 5% BSA in PBS. Serial diluted anti-IFNAR-1 antibodies were incubated with the coated antigen for 1 h at room temperature. The resulting plates were washed with PBS/T and incubated with goat anti-mouse IgG-HRP for 1 h at room temperature. The plates were developed with TMB substrate and analyzed by spectrophotometer at OD 450-630 nm. The results of the ELISA assays are summarized in Table 2, which shows $EC_{50}$ of binding to human IFNAR-1 protein.

TABLE 2

Binding $EC_{50}$(nM) on hIFNAR-1 protein.

| Antibody | $EC_{50}$ (nM) |
|---|---|
| 4D8 | 0.067 |
| 8G11 | 0.069 |
| 34H8 | 0.064 |
| 104A3 | 0.056 |
| 106A7 | 0.099 |
| 107 E12 | 0.075 |
| 124D12 | 0.062 |
| 260H8 | 0.055 |
| 268 E9 | 0.088 |
| 269A7 | 0.476 |
| 293H10 | 0.097 |
| 370 E5 | 0.052 |
| 392D6 | 0.054 |
| 402G3 | 0.137 |
| 430H6 | 0.733 |
| 485G10 | 0.015 |
| 487 E3 | 0.028 |

Anti-IFNAR-1 Antibody BIACORE Analysis

The binding of the antibodies to recombinant His-tagged human IFNAR-1-ECD protein was examined by Biacore T200 using a capture method. The anti-IFNAR-1 antibodies were captured using anti-human Fc antibody or Protein A which were coated on chip. The serial concentrations of his-tagged human IFNAR-1-ECD protein (0-8 nM) were injected over capture antibodies at the flow rate of 30 µl/min. The dissociation phases were 600 s or 1200 s. The results are shown in Table 3 below. The Biacore results for the anti-IFNAR-1 antibodies demonstrate that these anti-IFNAR-1 antibodies are high affinity binders to human IFNAR-1.

TABLE 3

Binding of antibodies to recombinant IFNAR-1 protein

| Antibody | ka (1/Ms) | kd (1/s) | KD (M) |
|---|---|---|---|
| 4D8 | 2.31E+06 | 9.03E−05 | 3.90E−11 |
| 8G11 | 2.36E+06 | 6.40E−05 | 2.71E−11 |
| 34H8 | 2.37E+06 | 4.41E−05 | 1.86E−11 |

Example 3. IFN-Responsive Reporter Assay for Screening Anti-IFNAR-1 Mouse Monoclonal Antibodies HEK-Blue™ IFNα/β cells (InvivoGen) are specifically designed to monitor the activation of the JAK-STAT pathway induced by type I IFNs. Upon IFN-α or IFN-β stimulation, these cells activate the JAK-STAT pathway and subsequently the expression of the reporter gene named secreted embryonic alkaline phosphatase (SEAP). SEAP which is secreted in the supernatant is easily detectable by using a SEAP detection reagent QUANTI-Blue™ (InvivoGen). A neutralizing antibody, which blocks interferon binding to its receptor, will inhibit IFN-induced reporter gene expression. This reporter assay was utilized for screening anti-IFNAR-1 mouse monoclonal antibodies.

HEK-Blue™ IFNα/β cells were incubated with 400 U/ml IFNα2b in the presence of serial dilutions of anti-IFNAR-1 mouse monoclonal antibodies overnight. The expression of reporter gene SEAP was determined by using a spectrophotometer at 650 nm. $EC_{50}$ of the tested antibodies are listed in Table 4. Among these antibodies, 4D8, 8G11, 34H8, 485G10 and 487E3 antibodies showed superior effects in blocking IFNα2b signal. Given the analysis on sequence homology, the clones of 8G11 and 485G10 were selected for further humanization and characterization.

TABLE 4

Reporter assay for the antibodies

| Clone ID | $EC_{50}$ (nM) |
|---|---|
| 4D8 | 0.460 |
| 8G11 | 0.465 |
| 34H8 | 0.560 |
| 104A3 | 1.310 |
| 106A7 | 3.516 |
| 107E12 | 1.207 |
| 124D12 | 0.981 |
| 260H8 | 5.074 |
| 269A7 | 6.713 |
| 286E9 | 3.871 |
| 293H10 | 1.285 |
| 370E5 | 2.170 |
| 392D6 | 0.824 |
| 402G3 | 1.267 |
| 430H6 | 1.297 |

TABLE 4-continued

Reporter assay for the antibodies

| Clone ID | EC$_{50}$ (nM) |
|---|---|
| 485G10 | 0.286 |
| 487E3 | 0.161 |

Example 4. Anti-IFNAR-1 mAb Humanization

A. 8G11

The mouse antibody 8G11 variable region genes were employed to create a humanized MAb. In the first step of this process, the amino acid sequences of the VH and VK of 8G11 were compared against the available database of human Ig gene sequences to identify the overall best-matching human germline Ig gene sequences. For the heavy chain, the closest human match was the IGHV1-46*01 gene. For the light chain, the best human match was the IGKV1-9*01 gene.

Humanized variable domain sequences were then designed where the CDR1 (SEQ ID NO:77), 2 (SEQ ID NO:78), and 3 (SEQ ID NO:80) sequences of the 8G11 VH were grafted onto framework sequences of the IGHV1-46*01 gene and the CDR1 (SEQ ID NO:81), 2 (SEQ ID NO:82) and 3 (SEQ ID NO:83) of the 8G11 light chain were grafted onto framework sequences of the IGKV1-9*01 gene. A 3D model was then generated to determine if there were any framework positions where replacing the mouse amino acid to the human amino acid could affect binding and/or CDR conformation. In the case of the heavy chain, K12, V20, A24, R38, M48, V68, M70, R72, V79 and M81 (Kabat numbering) in human framework was identified and subjected to back-mutations to their moue counterpart amino acid i.e.: K12V, V20L, A24G, R38K, M48I, V68A, M70I, R72A, V79A and M81L. In the case of the light chain, L4, A13, I21, A43, L46, T74, L78 and Y87 (Kabat numbering) in human framework was identified and subjected to back-mutation to their moue counterpart amino acid i.e.: L4M, A13T, I21V, A43S, L46V, T74I, L78V and Y87F. At the meantime, G56 A mutation was employed to remove the PTM.

TABLE 5

8G11 sequences and CDRs

| Antibody chain or domain | Sequences (CDR underlined and bold) | SEQ ID NO: |
|---|---|---|
| 8G11-VH | EVQLQQSGAELVKPGASVKLSCTGEGFNIKDYYMHWVKQRAEQGLEWIGR IDPEDGETKYAPKFQGKATITADTSSNTAYLQVSSLTSEDTAVYYCARGG NFYVMDYWGQGTSVTVSS | 7 |
| 8G11-VL | DIVMTQSQKFMSTSVGDRVSVTCKASQNVGTNVVWYQQKPGQSPKVLIYS ASYRVSGVPDRFTGSGSGTDFTLIISNVQSEDLAEYFCQQKNNYPYTFGG GTKLEIK | 8 |
| CDRH1 | DYYMH | 77 |
| CDRH2 | RIDPEDGETKYAPKFQG | 78 |
| CDRH2 (modified) | RIDPEDAETKYAPKFQG | 79 |
| CDRH3 | GGNFYVMDY | 80 |
| CDRL1 | KASQNVGTNVV | 81 |
| CDRL2 | SASYRVS | 82 |
| CDRL3 | QQKNNYPYT | 83 |

The humanized sequences are listed in Table 6: 8G11-VH1, 8G11-VH2, 8G11-VH3, 8G11-VH4, 8G11-VL1, 8G11-VL2, 8G11-VL3, and 8G11-VL4.

TABLE 6

Humanized sequences

| Antibody chain | Sequences (CDR italic; back mutations bold and underlined) | SEQ ID NO: |
|---|---|---|
| 8G11-VH1 | QVQLVQSGAEVKKPGASVKVSCKASGFNIK*DYYMH*WVRQAPGQGLEWMG*R* *IDPEDAETK*YAPKFQGRVTMTRDTSTSTVYMELSSLRSEDTAVYYCAR*GG* *NFYVMDY*WGQGTLVTVSS | 84 |
| 8G11-VH2 | QVQLVQSGAEVVKPGASVKVSCKGSGFNK*DYYMH*WVRQAPGQGLEWIG*R* *IDPEDAETKYAPKFQG*RVTMTADTSTSTVYMELSSLRSEDTAVYYCAR*GG* *NFYVMDY*WGQGTLVTVSS | 85 |

TABLE 6-continued

Humanized sequences

| Antibody chain | Sequences (CDR italic; back mutations bold and underlined) | SEQ ID NO: |
|---|---|---|
| 8G11-VH3 | QVQLVQSGAEVVKPGASVKVSCKGSGFNK*DYYMH*WVKQAPGQGLEWIGR*IDPEDA*ETKYAPKFQG*RVTITADTSTSTVYLELSSLRSEDTAVYYCAR*GGNFYVMDY*WGQGTLVTVSS | 86 |
| 8G11-VH4 | QVQLVQSGAEVVKPGASVKLSCKGSGFNK*DYYMH*WVKQAPGQGLEWIGR*IDPEDA*ETKYAPKFQG*RATITADTSTSTAYLELSSLRSEDTAVYYCAR*GGNFYVMDY*WGQGTLVTVSS | 87 |
| 8G11-VL1 | DIQLTQSPSFLSASVGDRVTITC*KASQNVGTNVVW*YQQKPGKAPKLLIY*SASYRVS*GVPSRFSGSGSGTEFTLTISSLQPEDFATYYCQQKNNYPYTFGQGTKLEIK | 88 |
| 8G11-VL2 | DIQLTQSPSFLSTSVGDRVTITC*KASQNVGTNVVW*YQQKPGKSPKVLIY*SASYRVS*GVPSRFSGSGSGTEFTLIISSLQPEDFATYYC*QQKNNYPYT*FGQGTKLEIK | 89 |
| 8G11-VL3 | DIQLTQSPSFLSTSVGDRVTITC*KASQNVGTNVVW*YQQKPGKSPKVLIY*SASYRVS*GVPSRFSGSGSGTEFTLIISSVQPEDFATYFC*QQKNNYPYT*FGQGTKLEIK | 90 |
| 8G11-VL4 | DIQMTQSPSFLSTSVGDRVTVTC*KASQNVGTNVVW*YQQKPGKSPKVLIY*SASYRVS*GVPSRFSGSGSGTEFTLIISSVQPEDFATYFC*QQKNNYPYT*FGQGTKLEIK | 91 |

All the 16 IgGs were expressed in the HEK293 cell line. Express antibodies were performed for affinity ranking. Detailed data of affinity ranking were summarized in Table 7.

TABLE 7

Affinity ranking of humanized antibodies.

| Antibody | $k_a$ (1/Ms) | $k_d$ (1/s) | $K_D$ (M) |
|---|---|---|---|
| VH4 + VL3 | 3.01E+05 | 8.52E−05 | 2.84E−10 |
| VH2 + VL2 | 2.87E+05 | 9.42E−05 | 3.28E−10 |
| VH4 + VL2 | 2.92E+05 | 9.69E−05 | 3.32E−10 |
| VH3 + VL3 | 3.01E+05 | 1.10E−04 | 3.64E−10 |
| VH2 + VL3 | 2.65E+05 | 9.65E−05 | 3.64E−10 |
| VH4 + VL4 | 2.83E+05 | 1.05E−04 | 3.72E−10 |
| VH2 + VL4 | 2.62E+05 | 1.02E−04 | 3.88E−10 |
| VH3 + VL2 | 2.84E+05 | 1.11E−04 | 3.89E−10 |
| VH3 + VL4 | 2.81E+05 | 1.13E−04 | 4.01E−10 |
| VH3 + VL1 | 2.56E+05 | 1.06E−04 | 4.13E−10 |
| VH2 + VL1 | 2.02E+05 | 8.84E−05 | 4.39E−10 |
| VH4 + VL1 | 2.03E+05 | 9.94E−05 | 4.89E−10 |
| VH1 + VL1 | 1.48E+05 | 9.83E−05 | 6.62E−10 |
| VH1 + VL2 | 1.67E+05 | 1.27E−04 | 7.65E−10 |
| VH1 + VL4 | 1.69E+05 | 1.41E−04 | 8.36E−10 |
| VH1 + VL3 | 2.31E+05 | 2.00E−04 | 8.65E−10 |

Based on the affinity ranking results, 4 IgGs (VH4+VL3, VH2+VL2, VH2+VL1, VH1+VL1) were expressed and purified. The purified antibodies were further selected for affinity measurement under different concentrations. Detailed data were summarized in Table 8.

TABLE 8

Affinity of selected humanized antibodies.

| Antibody | ka (1/Ms) | kd (1/s) | KD (M) |
|---|---|---|---|
| 8G11-H4L3 | 3.40E+05 | 7.47E−05 | 2.20E−10 |
| 8G11-H2L2 | 2.98E+05 | 1.25E−04 | 4.19E−10 |
| 8G11-H2L1 | 2.29E+05 | 9.24E−05 | 4.03E−10 |
| 8G11-H1L1 | 1.61E+05 | 2.19E−04 | 1.36E−09 |

B. 485G10

The mouse antibody 485G10 variable region genes were employed to create a humanized MAb. In the first step of this process, the amino acid sequences of the VH and VK of 485G10 were compared against the available database of human Ig gene sequences to identify the overall best-matching human germline Ig gene sequences. For the heavy chain, the closest human match was the IGHV1-2*05 gene. For the light chain, the best human match was the IGKV1-16*01 gene.

Humanized variable domain sequences were then designed where the CDR1 (SEQ ID NO:92), 2 (SEQ ID NO:93), and 3 (SEQ ID NO:95) sequences of the 485G10 heavy chain were grafted onto framework sequences of the IGHV1-2*05 gene and the CDR1 (SEQ ID NO:96), 2 (SEQ ID NO:C5) and 3 (SEQ ID NO:98) of the 485G10 light chain were grafted onto framework sequences of the IGKV1-16*01 gene. A 3D model was then generated to determine if there were any framework positions where replacing the mouse amino acid to the human amino acid could affect binding and/or CDR conformation. In the case of the heavy chain, V20, A24, R38, M48, V68, M70, R72, M81, A97 (Kabat numbering) in human framework was identified and subjected to back-mutations to their moue counterpart amino acid i.e.: V20L, A24G, R38K, M48I, V68A, M70I, R72A, M81L, A97G. In the case of the light chain, A13, I21, F36, S46, L78, V104 (Kabat numbering) in human framework was identified and subjected to back-mutation to their moue counterpart amino acid i.e.: A13T, I21V, F36Y, S46P, L78V, V104L. At the meantime, G56 A mutation was employed to remove the PTM.

TABLE 9

485G10 sequences and CDRs

| Antibody chain or domain | Sequences (CDR underlined and bold) | SEQ ID NO: |
|---|---|---|
| 485G10-VH | EVQLQQSGAELVKPGASVKLSCTGSGFNIKDYYIHWVKQRTEQGLEWIGR IDPEDGETKYAPKFQGKATITADTSSNTAYLQLSSLTSEDTVVYYCGRYH GYWALDYWGQGTSVTVSS | 73 |
| 485G10-VL | DIVMTQSQKFMSTSVGDRVSVTCKTSQNVGTNVAWYQQKPGQSPKPLIYS TSYRYSGVPDRFTGSGSGTDFTLIISNVQSEDLAEYFCHQYFSYPYTFGG GTLLEIK | 74 |
| CDRH1 | DYYIH | 92 |
| CDRH2 | RIDPEDGETKYAPKFQG | 93 |
| CDRH2 (modified) | RIDPEDAETKYAPKFQG | 94 |
| CDRH3 | YHGYWALDY | 95 |
| CDRL1 | KTSQNVGTNVA | 96 |
| CDRL2 | STSYRYS | 97 |
| CDRL3 | HQYFSYPYT | 98 |

The humanized sequences are listed in Table 10: 485G10-VH0, 485G10-VH1, 485G10-VH2, 485G10-VH3, 485G10-VL1, 485G10-VL2, 485G10-VL3, and 485G10-VL4.

TABLE 10

Humanized sequences

| Antibody chain | Sequences (CDR italic and underlined; back mutations bold) | SEQ ID NO: |
|---|---|---|
| 485G10-VH0 | QVQLVQSGAEVKKPGASVKVSCKASGFNIK*DYYIH*WVRQAPGQGLEWMG*R IDPEDAETKYAPKFQG*RVTMTRDTSISTAYMELSRLRSDDTVVYYCARYH GYWALDYWGQGTLVTVSS | 99 |
| 485G10-VH1 | QVQLVQSGAEVKKPGASVKVSCKASGFNIK*DYYIH*WVRQAPGQGLEWMG*R IDPEDAETKYAPKFQG*RVTMTADTSISTAYMELSRLRSDDTVVYYCARYH GYWALDYWGQGTLVTVSS | 100 |
| 485G10-VH2 | QVQLVQSGAEVKKPGASVKLSCKASGFNIK*DYYIH*WVKQAPGQGLEWIG*R IDPEDAETKYAPKFQG*RVTMTADTSISTAYMELSRLRSDDTVVYYCGRYH GYWALDYWGQGTLVTVSS | 101 |
| 485G10-VH3 | QVQLVQSGAEVKKPGASVKLSCKGSGFNIK*DYYIH*WVKQAPGQGLEWIG*R IDPEDAETKYAPKFQG*RATITADTSISTAYLELSRLRSDDTVVYYCGRYH GYWALDYWGQGTLVTVSS | 102 |
| 485G10-VL1 | DIQMTQSPSSLSASVGDRVTITC*KTSQNVGTNVA*WFQQKPGKAPKSLIY*S TSYRYS*GVPSRFSGSGSGTDFTLTISSLQPEDFATYYC*HQYFSYPYT*FGP GTKVDIK | 103 |
| 485G10-VL2 | DIQMTQSPSSLSTSVGDRVTITC*KTSQNVGTNVA*WYQQKPGKAPKPLIY*S TSYRYS*GVPSRFSGSGSGTDFTLTISSLQPEDFATYYC*HQYFSYPYT*FGP GTKVDIK | 104 |
| 485G10-VL3 | DIQMTQSPSSLSTSVGDRVTITC*KTSQNVGTNVA*WYQQKPGKAPKPLIY*S TSYRYS*GVPSRFSGSGSGTDFTLTISSVQPEDFATYYC*HQYFSYPYT*FGP GTKLDIK | 105 |
| 485G10-VL4 | DIQMTQSPSSLSTSVGDRVTVTC*KTSQNVGTNVA*WYQQKPGKAPKPLIY*S TSYRYS*GVPSRFSGSGSGTDFTLTISSVQPEDFATYYC*HQYFSYPYT*FGP GTKLDIK | 106 |

All the 16 IgGs could be expressed in the HEK293 cell line. Express antibodies were performed for affinity ranking. Detailed data of affinity ranking were summarized in table 11.

TABLE 11

Affinity ranking of humanized antibodies.

| Antibody | $k_a$ (1/Ms) | $k_d$ (1/s) | $K_D$ (M) |
| --- | --- | --- | --- |
| VH1 + VL3 | 3.11E+05 | 1.01E−04 | 3.25E−10 |
| VH1 + VL2 | 3.08E+05 | 2.01E−04 | 6.52E−10 |
| VH1 + VL4 | 3.27E+05 | 2.16E−04 | 6.60E−10 |
| VH2 + VL3 | 2.81E+05 | 2.38E−04 | 8.48E−10 |
| VH3 + VL2 | 3.06E+05 | 2.64E−04 | 8.64E−10 |
| VH3 + VL4 | 3.54E+05 | 2.71E−04 | 7.66E−10 |
| VH3 + VL3 | 3.32E+05 | 2.79E−04 | 8.41E−10 |
| VH2 + VL2 | 3.29E+05 | 2.98E−04 | 9.06E−10 |
| VH2 + VL4 | 3.03E+05 | 3.00E−04 | 9.90E−10 |
| VH0 + VL3 | 2.94E+05 | 3.16E−04 | 1.07E−09 |
| VH0 + VL4 | 2.55E+05 | 3.18E−04 | 1.25E−09 |
| VH0 + VL2 | 2.79E+05 | 4.39E−04 | 1.57E−09 |
| VH1 + VL1 | 3.28E+05 | 1.03E−03 | 3.14E−09 |
| VH0 + VL1 | 5.09E+05 | 4.75E−03 | 9.33E−09 |
| VH2 + VL1 | 3.23E+05 | 6.63E−03 | 2.05E−08 |
| VH3 + VL1 | 9.71E+05 | 1.85E−02 | 1.91E−08 |

Based on the affinity ranking results, 4 IgGs (VH1+VL2, VH1+VL4, VH1+VL3, VH2+VL3) were expressed and purified. The purified antibodies were further selected for affinity measurement under different concentrations. Detailed data were summarized in Table 12.

TABLE 12

Affinity of selected humanized antibodies.

| Antibody | ka (1/Ms) | kd (1/s) | KD (M) |
| --- | --- | --- | --- |
| 485G10-H1L2 | 2.07E+05 | 3.21E−04 | 1.55E−09 |
| 485G10-H1L4 | 1.96E+05 | 2.59E−04 | 1.32E−09 |
| 485G10-H1L3 | 1.87E+05 | 2.32E−04 | 1.24E−09 |
| 485G10-H2L3 | 1.86E+05 | 3.66E−04 | 1.96E−09 |

Figure 1B:
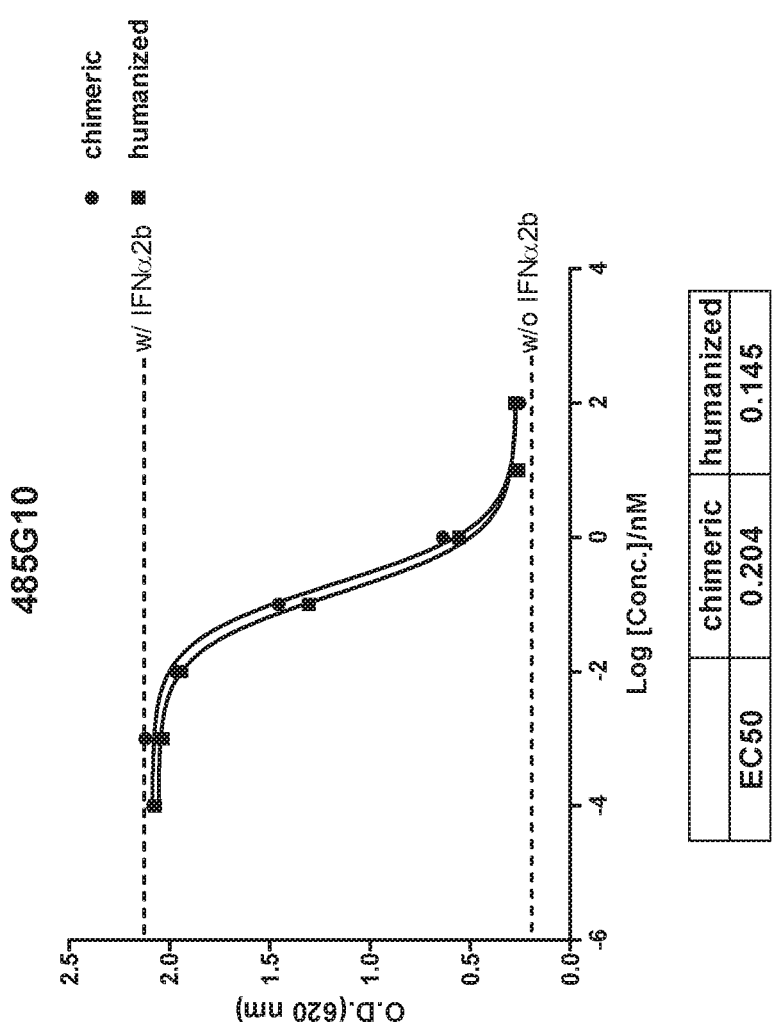

Example 5. Anit-IFNAR-1 Humanized Monoclonal Antibodies Inhibit the Biological Activity of Interferon Cab in IFN-Responsive Reporter Assay To evaluate the IFNAR-1-blocking function of humanized antibodies, in vitro IFN-responsive reporter assay described in Example 3 was used. HEK-Blue™ IFNα/β cells were incubated with 400 U/ml IFNα2b in the presence of serial diluted anti-IFNAR-1 humanized monoclonal antibodies overnight prior to determination by using a spectrophotometer at 650 nM. As shown in FIG. 1, the 8G11H, and 485G10H antibodies efficiently blocked IFNα2b-induced reporter gene expression. Their potency is comparable to that of the corresponding chimeric antibodies.

Figure 2A:
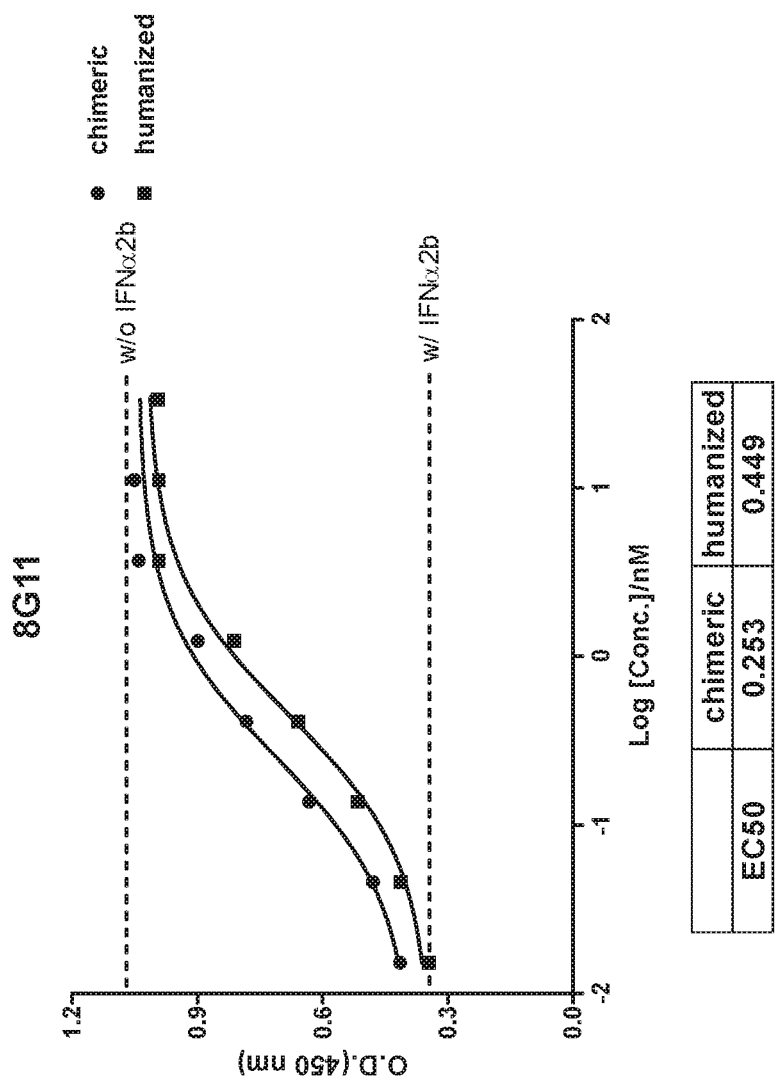
FIGS. 2A-B show that 8G11H and 485G10H antibodies dose-dependently reversed IFNα2b-mediated inhibition of Daudi cell proliferation.
Figure 2B:
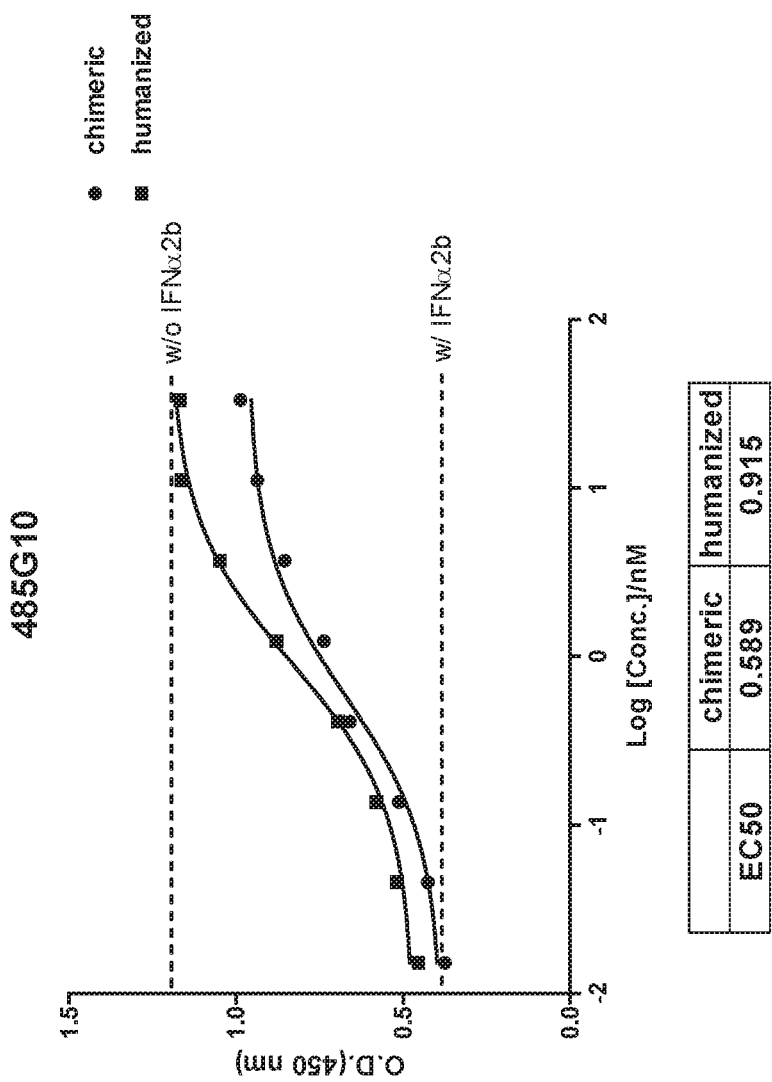

Example 6. Anit-IFNAR-1 Humanized Monoclonal Antibodies Inhibit the Biological Activity of Interferon α2b in Daudi Cell Proliferation The cell line Daudi, derived from a human B-lymphoblast Burkitt's lymphoma, expresses high levels of IFNAR, and the growth of these cells is inhibited by type I interferons. To measure the functional blocking ability of humanized anti-IFNAR-1 antibodies, Daudi cells were cultured with interferon α2b in the presence or absence of a serial diluted anti-IFNAR-1 humanized antibodies. The cell proliferation was measured by Cell Counting Kit-8 (CCK8, DOJINDO Laboratories). As described in FIG. 2, the 8G11H and 485G10H antibodies dose-dependently reverse IFNα2b-mediated inhibition of Daudi cell proliferation. Their potency is comparable to that of the corresponding chimeric antibodies.

Example 7. Anti-IFNAR-1 Human Monoclonal Antibodies Inhibit the Biological Activity of Multiple Type I IFNs To assess the ability of humanized anti-IFNAR-1 antibodies to inhibit the biological activity of multiple type I IFNs, distinct IFN alpha subtypes were tested in the IFN-responsive reporter assay. HEK-Blue™ IFN-α/β cells were incubated with one of the following IFN alpha subtypes: 1, 2a, 4, 5, 6, 7, 8, 10, 14, 16, 17 and 21 in the presence of serial dilutions of the tested antibodies or an isotype control. The reporter signal was determined as described in Example 3. As shown in Table 13, the 8G11H and 485G10H antibodies can efficiently inhibit the cell signal elicited by multiple type I IFNs. Their $EC_{50}$ is in the pM level.

TABLE 13

Reporter assay of multiple Type I IFNs

| | $EC_{50}$ (nM) | |
| --- | --- | --- |
| Clone ID | 8G11H | 485G10H |
| IFNα 1 | 0.057 | 0.051 |
| IFNα 2a | 0.052 | 0.048 |
| IFNα 4 | 0.055 | 0.054 |
| IFNα 5 | 0.087 | 0.098 |
| IFNα 6 | 0.090 | 0.072 |
| IFNα 7 | 0.039 | 0.047 |
| IFNα 8 | 0.604 | 0.490 |
| IFNα 10 | 0.402 | 0.550 |
| IFNα 14 | 0.215 | 0.153 |
| IFNα 16 | 0.061 | 0.079 |
| IFNα 17 | 0.035 | 0.035 |
| IFNα 21 | 0.079 | 0.065 |

Example 8. Anti-IFNAR-1 Human Monoclonal Antibodies Inhibit Type I IFN Mediated Anti-Viral Function Type I IFNs were firstly identified by their unique anti-viral function. To evaluate the blocking effects of the anti-IFNAR-1 antibodies on type I IFN-mediated anti-viral function, an IFNα2b-based anti-viral assay was established. Briefly, cell line Huh7 was engineered to contain the full-length HCV genotype 1b replicon (Con1b) which was linked to a firefly luciferase reporter gene. The abundance of reporter gene closely correlated with replication levels of HCV replicon. The activity of anti-IFNAR-1 antibodies in blocking IFNα2b induced anti-viral function can be determined by the restoration of reporter gene levels in IFNα2b-treated Huh?-Con1b cells.

Huh7-Con1b cells were cultured with 400 U/ml IFNα2b in the presence or absence of serial diluted anti-IFNAR-1 humanized monoclonal antibodies for 48 hours. The expression of firefly luciferase reporter gene was measured by addition of Britelite plus reagent and further determined by using a spectrophotometer. As shown in Table 14, anti-IFNAR-1 humanized monoclonal antibodies 8G11H and 485G10H efficiently inhibit IFNα2b-induced anti-viral function, their EC50 is comparable to that of the corresponding chimeric antibodies.

TABLE 14

IFNα2b-mediated anti-viral assay

| Clone ID | EC$_{50}$ (nM) |
| --- | --- |
| 8G11-chimeric | 7.733 |
| 8G11H | 8.067 |
| 485G10-chimeric | 16.267 |
| 485G10H | 13.867 |

Example 9. Inhibition of Type I IFN-Induced IP-10 Secretion by Anti-IFNAR-1 Humanized Monoclonal Antibodies Upon type I IFNs stimulation, normal peripheral blood mononuclear cells (PBMCs) express a serial of IFN-response genes including IP-10. The activity of anti-IFNAR-1 antibodies was tested for inhibition of IFNα2b-induced secretion of IP-10 by normal PBMCs.

PBMCs were incubated with 400 U/ml IFNα2b in the presence or absence of anti-IFNAR-1 humanized monoclonal antibodies for 48 hours. Supernatants were collected and analyzed for IP-10 concentration by using a quantitative LANCE kit (Cisbio) according to manufacturer recommendations. As shown in FIG. 3, anti-IFNAR-1 humanized monoclonal antibodies 8G11H and 485G10H dose-dependently inhibit recombinant IFNα2b-induced secretion of IP-10 by normal PBMC culture.

Example 10. Inhibition of Type I IFN-Induced Dendritic Cell Development by Anti-IFNAR-1 Humanized Monoclonal Antibodies It is well known that type I IFNs induce the development and maturation of dendritic cells, as defined by the expression of specific cell surface markers such as CD38, CD80 and CD86 et al, and the capability to stimulate naïve allogeneic CD4$^+$ T cell proliferation (mixed lymphocyte reaction, MLR). To evaluate the function of anti-IFNAR-1 antibodies in blocking type I IFN signaling on dendritic cells differentiation, IFNα2b-mediated dendritic cells differentiation assay was established. Monocytes isolated from human PBMCs were cultured with 20 ng/ml GMCSF and 400 U/ml IFNα2b in the presence or absence of anti-IFNAR-1 humanized monoclonal antibodies for 72 hours. Monocyte-derived dendritic cells were collected and further cultured with human naïve allogeneic CD4$^+$ T cells at a ratio of 1:5 for 5 days. The cytokine IFN-γ, reflecting the proliferation status of CD4$^+$ T cells, in the culture supernatants were analyzed by ELISA assay.

Figure 4:
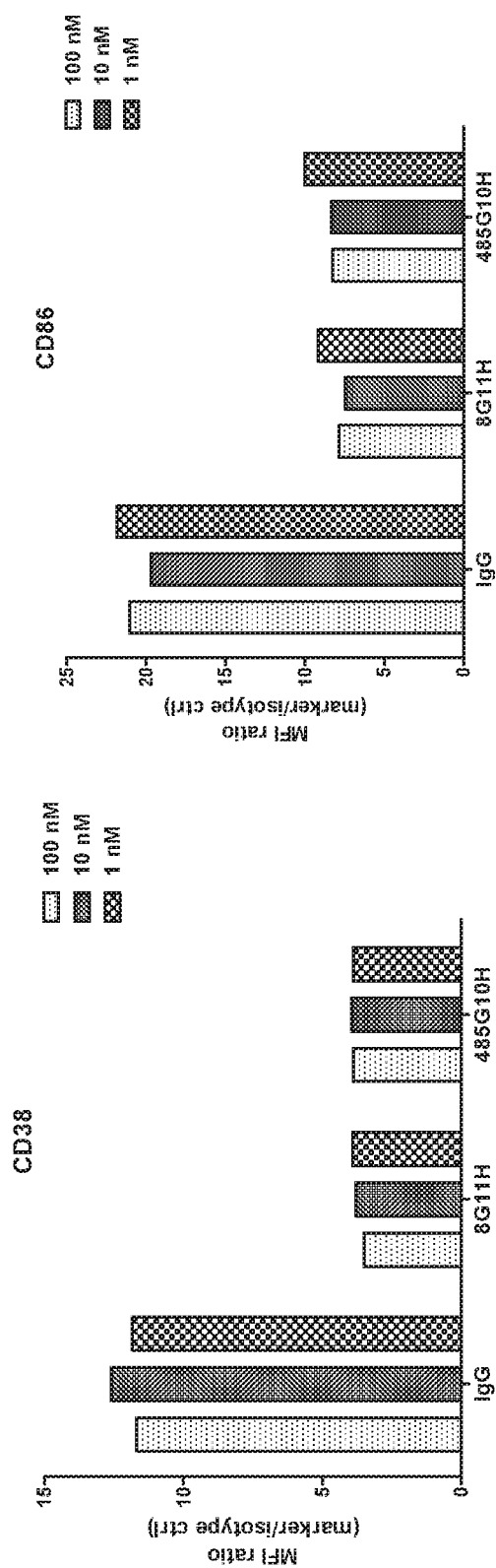
FIG. 4 shows that the 8G11H and 485G10H antibodies efficiently inhibited the in vitro differentiation of dendritic cells as demonstrated by significant reduction of differentiated cell surface markers CD38 and CD86 expression.
Figure 5:
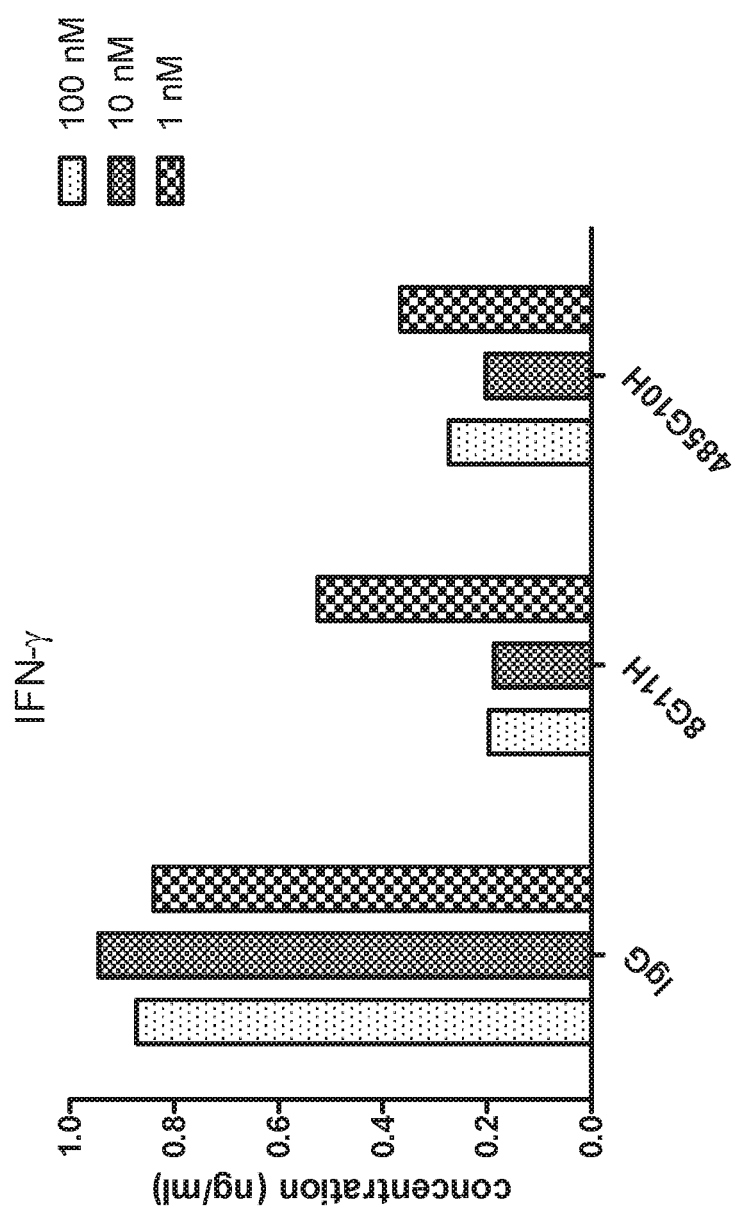
FIG. 5 shows that the 8G11H and 485G10H antibodies efficiently inhibited the in vitro differentiation of dendritic cells, which resulted in impaired responses in differentiated cell-mediated MLR as demonstrated by decreased production of IFN-γ by CD4$^+$ T cells.

As shown in FIG. 4, the addition of anti-IFNAR-1 humanized monoclonal antibodies, 8G11H or 485G10H, into the differentiation systems results in significant reduction of cell surface markers CD38 and CD86 expression, as well as obvious impaired responses in MLR as demonstrated by decreased production of IFN-γ by CD4+ T cells (FIG. 5). The results demonstrated that anti-IFNAR-1 humanized monoclonal antibodies, 8G11H and 485G10H, can efficiently block IFNα2b signaling on dendritic cells development.

Example 11. Inhibition of SLE Plasma Mediated Dendritic Cell Development by Anti-IFNAR-1 Humanized Monoclonal Antibodies The capacity of SLE patients' plasma to induce dendritic cell development correlates with disease activity and depends on the actions of IFNα. In this example, the purified human anti-IFNAR-1 antibodies, 8G11H and 485G10H, were tested for inhibition of SLE plasma-induced dendritic cell development, as assessed by the impaired capability of antibody-treated dendritic cells to stimulate naïve allogeneic CD4$^+$ T cell proliferation (MLR).

Figure 6:
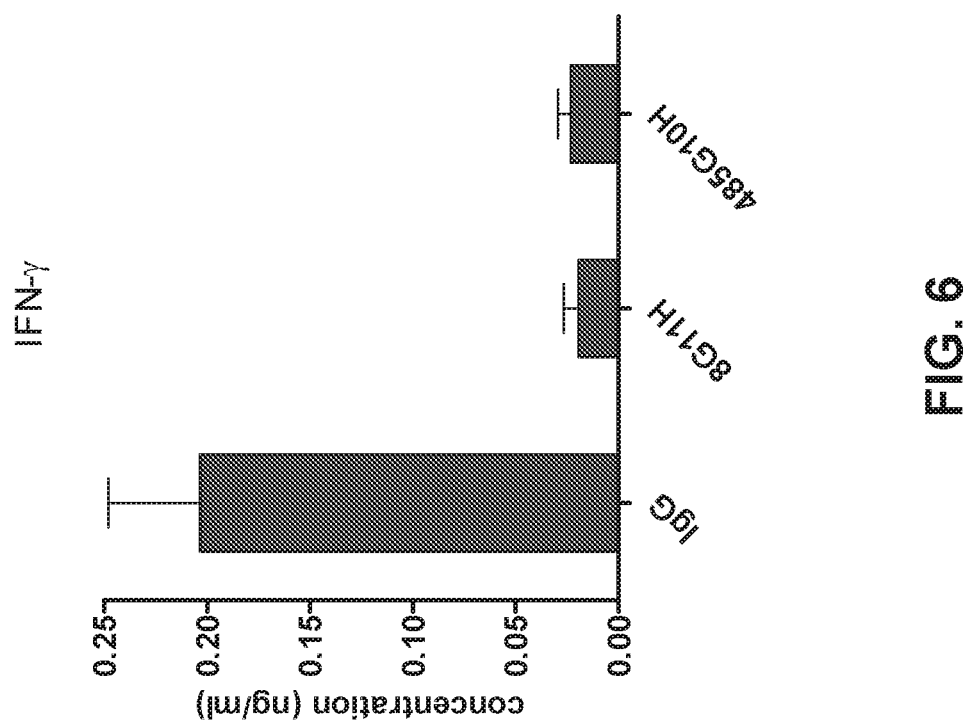
FIG. 6 shows that humanized monoclonal antibodies 8G11H and 485G10H significantly inhibited the SLE plasma mediated dendritic cell development in in vitro system.

Monocytes isolated from human PBMCs were cultured in media containing 25% SLE patient plasma in the presence or absence of anti-IFNAR-1 antibodies (15 μg/ml) for three to five days. The differentiated cells were then collected and co-cultured with human naïve allogeneic CD4$^+$ T cells at a ratio of 1:5 for five days. The cytokine IFN-γ, reflecting the proliferation status of CD4$^+$ T cells, in the culture supernatants were analyzed by ELISA assay. As shown in FIG. 6, anti-IFNAR-1 humanized monoclonal antibodies 8G11H and 485G10H significantly inhibit the IFNα-dependent dendritic cell development, as demonstrated by impaired capability of differentiated cells to stimulate MLR with marked reduction of the cytokine IFN-γ production by CD4$^+$ T cells.

Example 12. Bispecific Antibody to Target BAFF and IFNAR-1

This example tested whether certain formats of anti-BAFF/anti-IFNAR1 bispecific antibodies can retain the binding affinities, and inhibitive activities, to both antigens.

Figure 8:
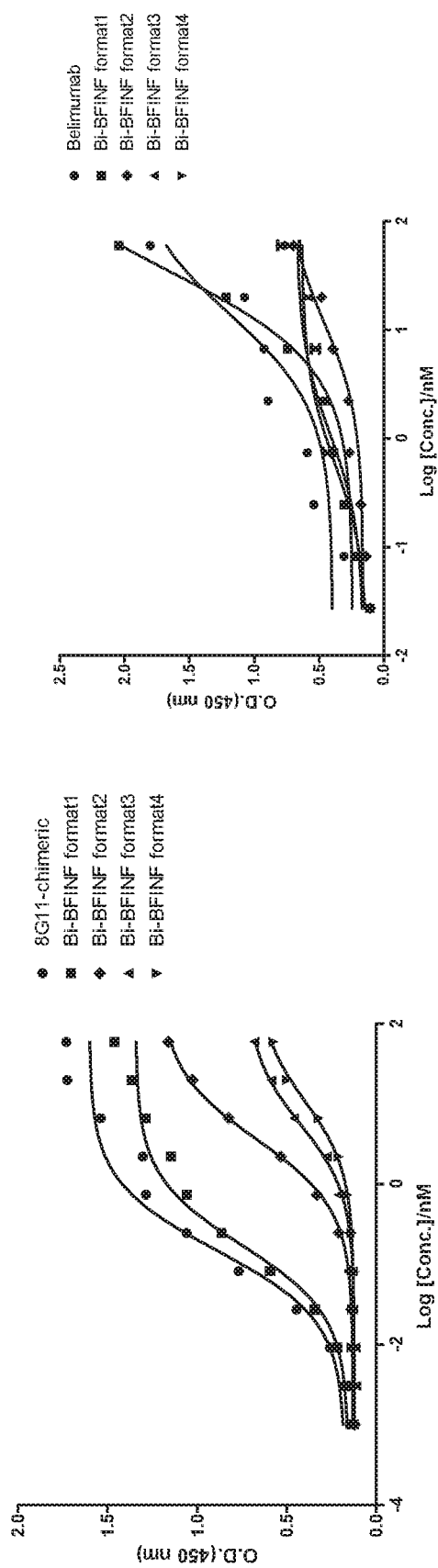
FIG. 8 shows that the bispecific antibody exhibited similar activity with 8G11 antibody in binding to IFNAR-1 and comparable activity to Belimumab in binding to BAFF.
Figure 9A:
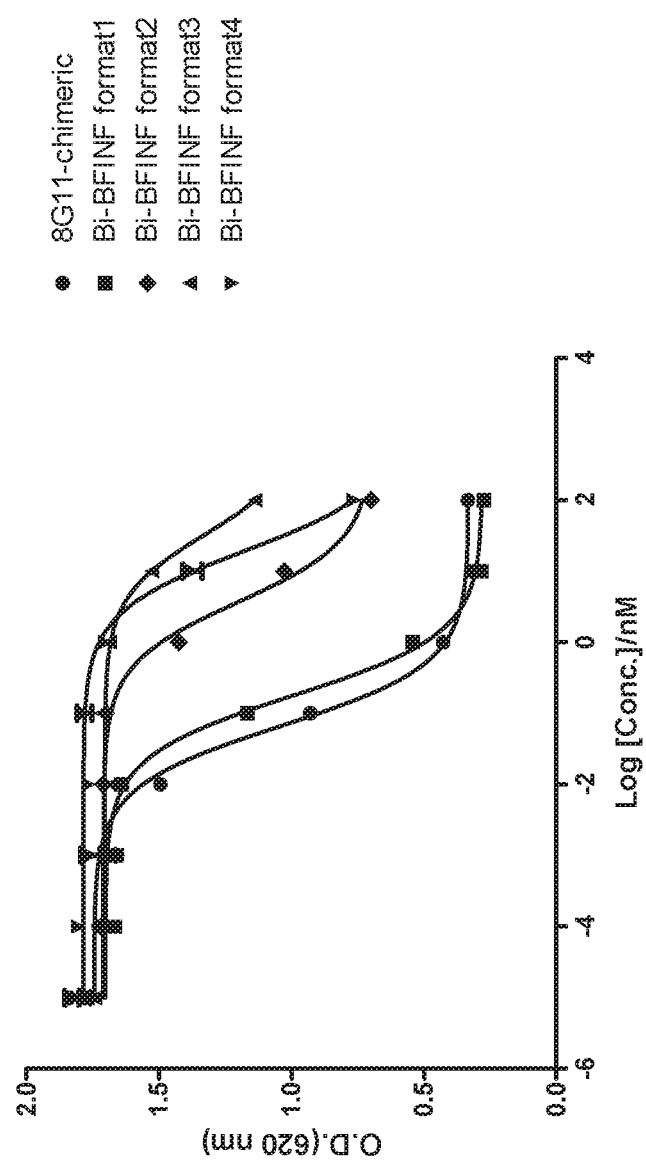
FIGS. 9A-B show that Bi-BFINF antibody had comparable activity to chimeric 8G11 in blocking IFNα2b signaling (A); Bi-BFINF antibody exhibited better activity in blockade of BAFF-induced B cell proliferation (B).
Figure 9B:
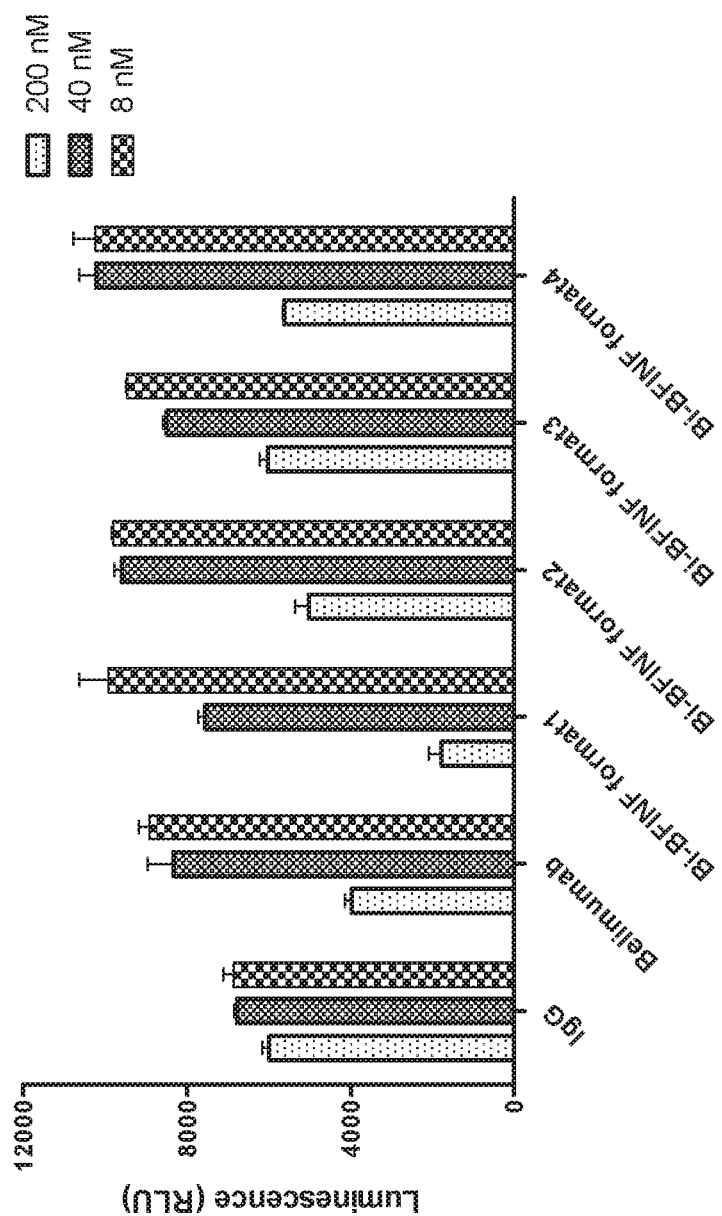

The bispecific monoclonal antibody was generated with Belimumab (anti-BAFF) and 8G11 chimeric antibody. FIG. 7 depicts a schematic of designed four formats for the anti-IFNAR/BAFF bispecific antibody (Bi-BFINR). The binding properties of Bi-BFINR to human IFNAR-1 protein and human BAFF protein were detected respectively by ELISA assay. As shown in FIG. 8, the format 1 of Bi-BFINF exhibited similar activity as 8G11 antibody in binding to IFNAR-1 and comparable activity to Belimumab in binding to BAFF. Furthermore, cell-based assay was performed to characterize the biological function of Bi-BFINF. For anti-IFNAR-1 arm, IFNα2b-based reporter assay was applied. As shown in FIG. 9A, Bi-BFINF antibody with format 1 has the comparable activity to chimeric 8G11 in blocking IFNα2b signaling. For anti-BAFF arm, BAFF-induced B cell proliferation assay was performed. B cells isolated from Tonsil were cultured with 2 μg/ml recombinant BAFF in the presence or absence of Bi-BFINF for 72 hours. Cell-title glo was added to the cultures to determine B cell numbers. As shown in FIG. 9B, Bi-BFINF antibody with format 1 exhibits better activity in blockade of BAFF-induced B cell proliferation.

Example 13. Identification of Critical Amino Acids of hIFNAR-1 for 8G11 Binding

For epitope-mapping for the 8G11 antibody, a mutation library (alanine scan) of hIFNAR-1(1aa-409aa) was created. Binding of 8G11 Fab to each mutant clone in the alanine scanning library was determined, in duplicate, by high-throughput flow cytometry. For each point, background fluorescence was subtracted from the raw data, which were then normalized to Fab reactivity with WT target protein. For each mutant clone, the mean binding value was plotted as a function of expression (represented by control reactivity). 85288 Mab (R&D) and Anifrolumab were used as control antibody. To identify preliminary primary critical clones a threshold of >70% WT binding to control MAb or 8G11 Fab and <30% WT binding to test 8G11 Fab was applied.

Screening Results of the mutations are listed in Table 15. The clone H273A that did not meet the set thresholds but whose decreased binding activity and proximity to critical residues suggested that the mutated residue may be part of the antibody epitope. Critical residues whose mutation gave the lowest reactivities with specific antibodies are highlighted in bold and underlined. Validated critical residues represent amino acids whose side chains make the highest energetic contributions to the antibody-epitope interaction. Therefore, the highlighted (bold and underlined) residues K276, K278 are likely the major energetic contributors to binding. Results were showed in Table 16.

TABLE 15

Identification of critical residues for 8G11 Fab binding.
Binding Reactivity (% WT)

| Mutation | 8G11 Fab | 85288 Mab | Anifrolumab Mab |
|---|---|---|---|
| H273A | 31.2 | 95.5 | 88.1 |
| L274A | 22.7 | 115.1 | 105.6 |
| Y275A | 19.1 | 86.8 | 145.5 |
| K276A | 1.5 | 104.4 | 99.4 |
| K278A | 3.9 | 101.2 | 105.1 |

TABLE 16

Important residues for binding of Fab to the hIFNAR-1 protein.

| Antibody Name | Residues |
|---|---|
| 8G11 | H273, L274, Y275, K276, K278 |

Competition assays were used to test whether the antibodies 4D8, 8G11, 4B12, 30C8, 30B5, 34H8 and Anifrolumab competed with one another. The results showed that 4D8, 8G11, 4B12, 30C8, 30B5, and 34H8 competed with one another but none competed with Anifrolumab for binding to IFNAR-1. These data show that the newly identified antibodies target the same epitope on IFNAR-1 which is different from that for Anifrolumab.

Example 14. Pharmacokinetics of Humanized Anti-IFNAR1 Antibodies in Cynomolgus Monkeys A preliminary pharmacokinetics (PK) study was conducted in cynomolgus monkeys at a dose of 10 mg/kg of 8G11-H2L1 and 485G10-H1L3. Serum samples were collected relative to antibody injection at −0 (predose), 5 Min, 30 Min, 1 h, 2 h, 4 h, 8 h, 24 hr (1 day), 48h (2 days), 72 hr (3 days), 96 hr (4 days), 120 hr (5 days), 168 hr (7 days), 240 hr (10 days), 36 hr (14 days), 504 hr (21 days), 672 hr (28 days) and 840 hr (35 days). The levels of anti-IFNAR1 mAbs were measured by a generic ELISA method using recombinant IFNAR1 protein ECD as the capture antigen. PK parameters were calculated based on statistical moment theory by WinNonlin 6.3 software. Results are shown in Table 17.

Figure 10A:
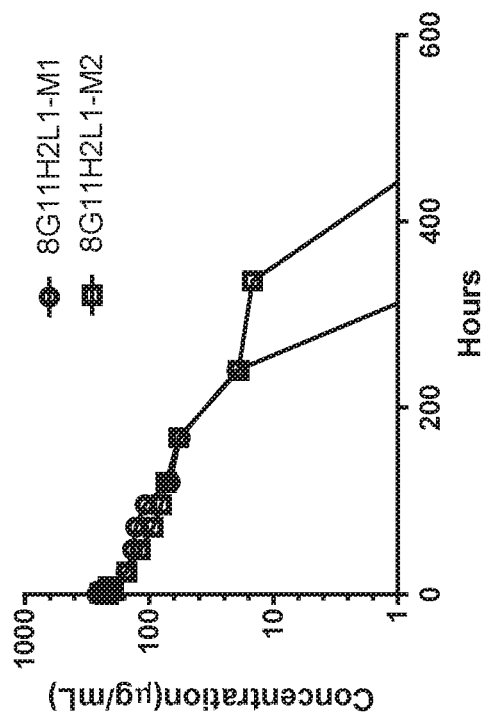
FIG. 10A shows time-concentration profiles of 485G10H1L3 in 2 cynomolgus monkeys.
Figure 10B:
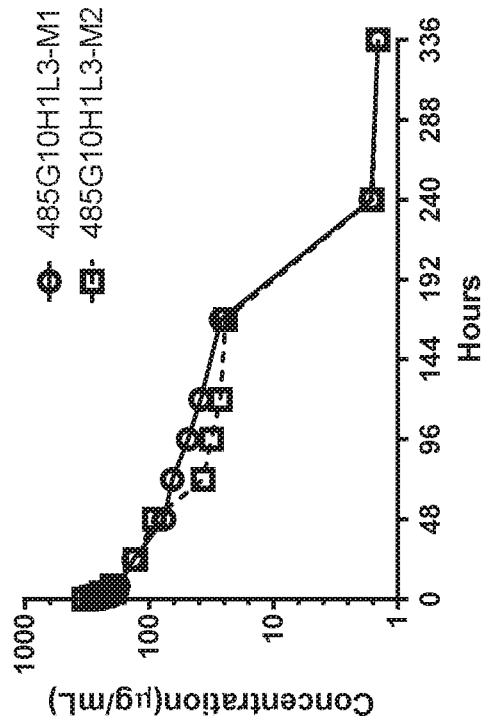
FIG. 10B shows time-concentration profiles of 8G11H2L1 in 2 cynomolgus monkeys.

Time-concentration profiles indicated that the PK of 8G11-H2L1 and 485G10-H1L3 were more in line with what one would expect for a typical IgG (FIGS. 10A and 10B),

TABLE 17

8G11-H2L1 and 485G10-H1L3 PK parameters in cynomolgus monkeys

| i.v. 10 mg/kg | | 485G10-H1L3 | 8G11-H2L1 |
|---|---|---|---|
| $HL\_Lambda\_z$ | h | 41.9 | 71.37 |
| $T_{max}$ | h | 0.08 | 0.08 |
| $C_{max}$ | μg/mL | 299.05 | 241.32 |
| $AUC_{last}$ | h * μg/mL | 12942.47 | 15450.93 |
| $Vz\_F\_obs$ | mL/kg | 46.4 | 65.6 |
| $Cl\_F\_obs$ | mL/h/kg | 0.77 | 0.64 |
| $MRT_{last}$ | h | 62.43 | 99.49 |

Figure 11A:
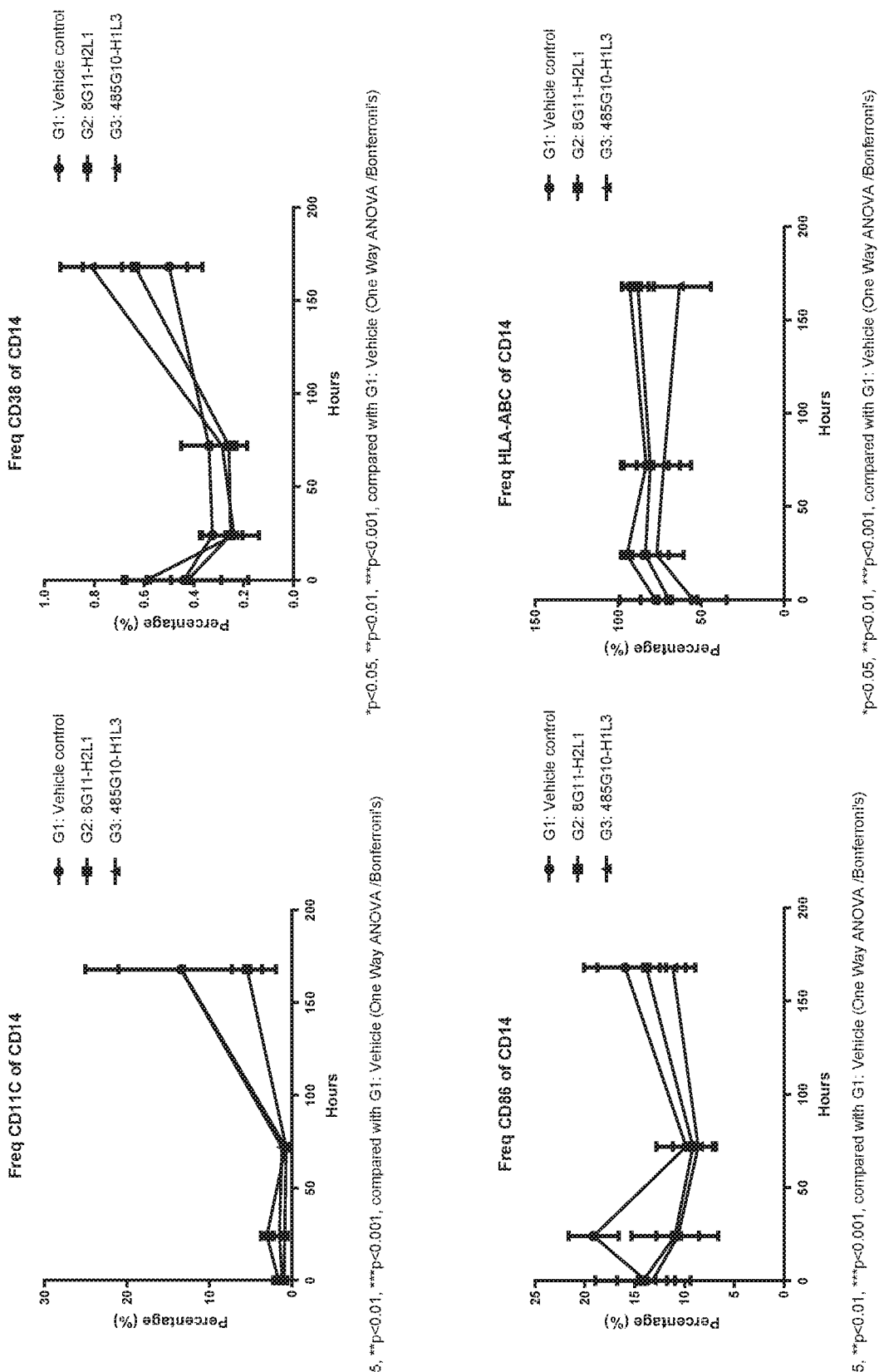
FIG. 11A shows CD11C, CD38, CD86, MHC Class I, MHC Class II and IFN-alpha R1 expression by FACs after dosing at 24 h, 48 h and 72 h.
Figure 11A:
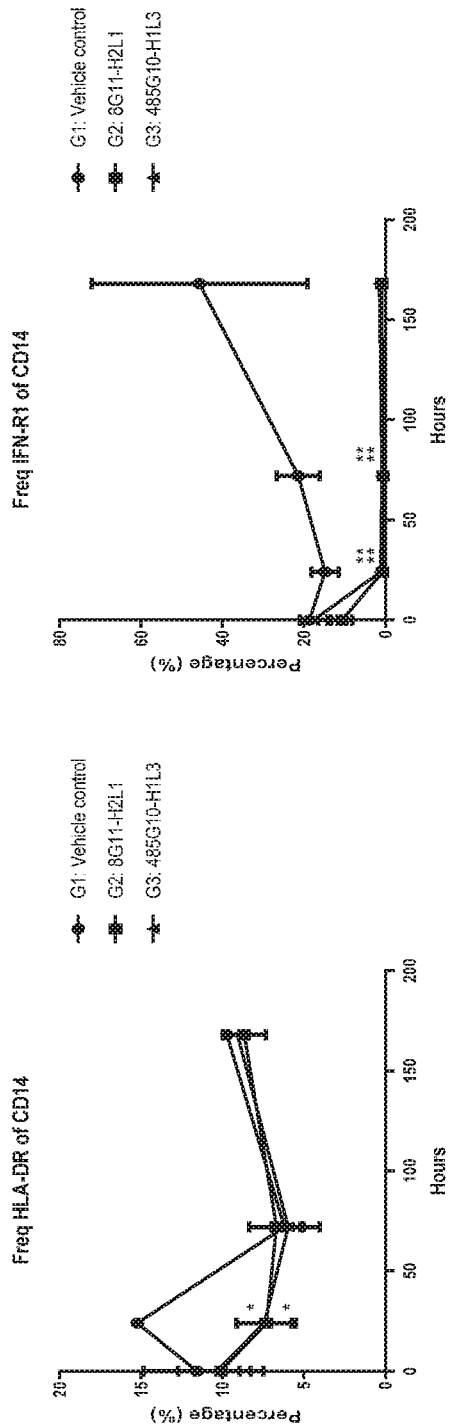

Example 15. Pharmacodynamics of Humanized Anti-IFNAR1 Antibodies in Cynomolgus Monkeys A pharmacodynamic (PD) model was to used study the ability of the anti-IFNAR1 antibodies to inhibit interferon activity in vivo. Cynomolgus monkeys were treated with i.v. infusion of 10 mg/kg 8G11-H2L1 and 485G10-H1L3 or vehicle control followed by i.m. dose of human IFN-α2b (3*10E6U/Kg). After treatment and IFN-α2b injection, blood was collected at predose, 24, 72 and 168 h after treatment for PD marker measurement. The expression of CD11C, CD38, CD86, MHC Class I, MHC Class II and IFN-alpha R1 was detected by FACS in total PBMC. As shown in FIG. 11A, 8G11-H2L1 and 485G10-H1L3 could significantly decrease the HLA-DR expression of CD14+ cell at 24 h after treatment. Meanwhile, 8G11-H2L1 and 485G10-H1L3 were also able to suppress the IFN-alpha R1 expression of CD14+ cell both at 24 h and 72 h after treatment.

Figure 11B:
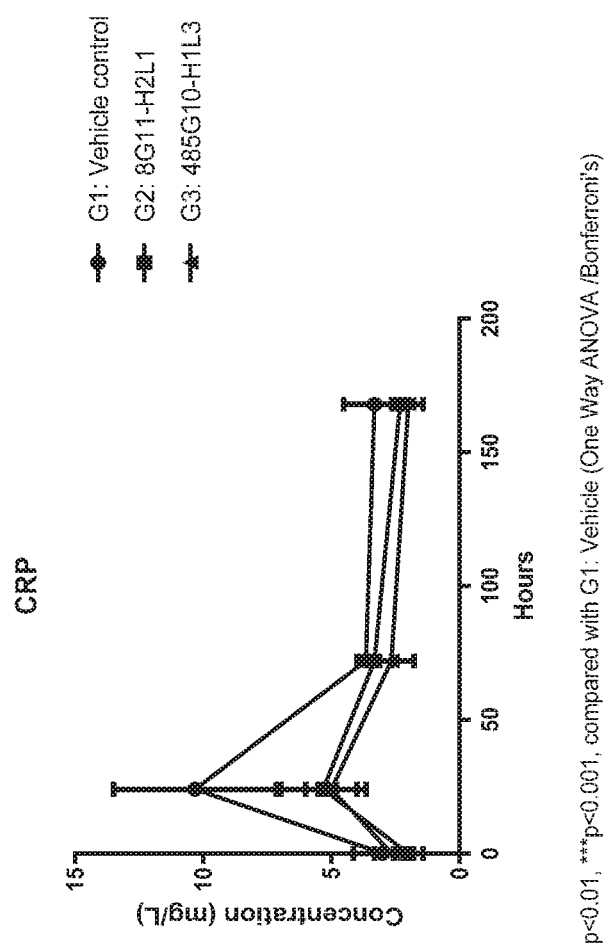
FIG. 11B shows the serum level of monkey neopterin, beta-2-microglobulin and CRP at 24 h, 48 h and 72 h after dosing.

The serum levels of monkey neopterin and beta-2-microglobulin were detected by ELISA performed according to the manufacturer's instruction. The level of CRP in peripheral blood was measured by blood biochemistry. As shown in FIG. 11B, Neopterin, Beta-2 Microglobulin and CRP in vehicle group were increased rapidly within 24 h. Compared with vehicle control, 8G11-H2L1 and 485G10-H1L3 could suppress the neopterin and beta-2 Microglobulin significantly at 24 h and 72 h after dosing. Also, 8G11-H2L1 and 485G10-H1L3 were able to decrease the CRP significantly at 24 h after dosing.

Figure 11C:
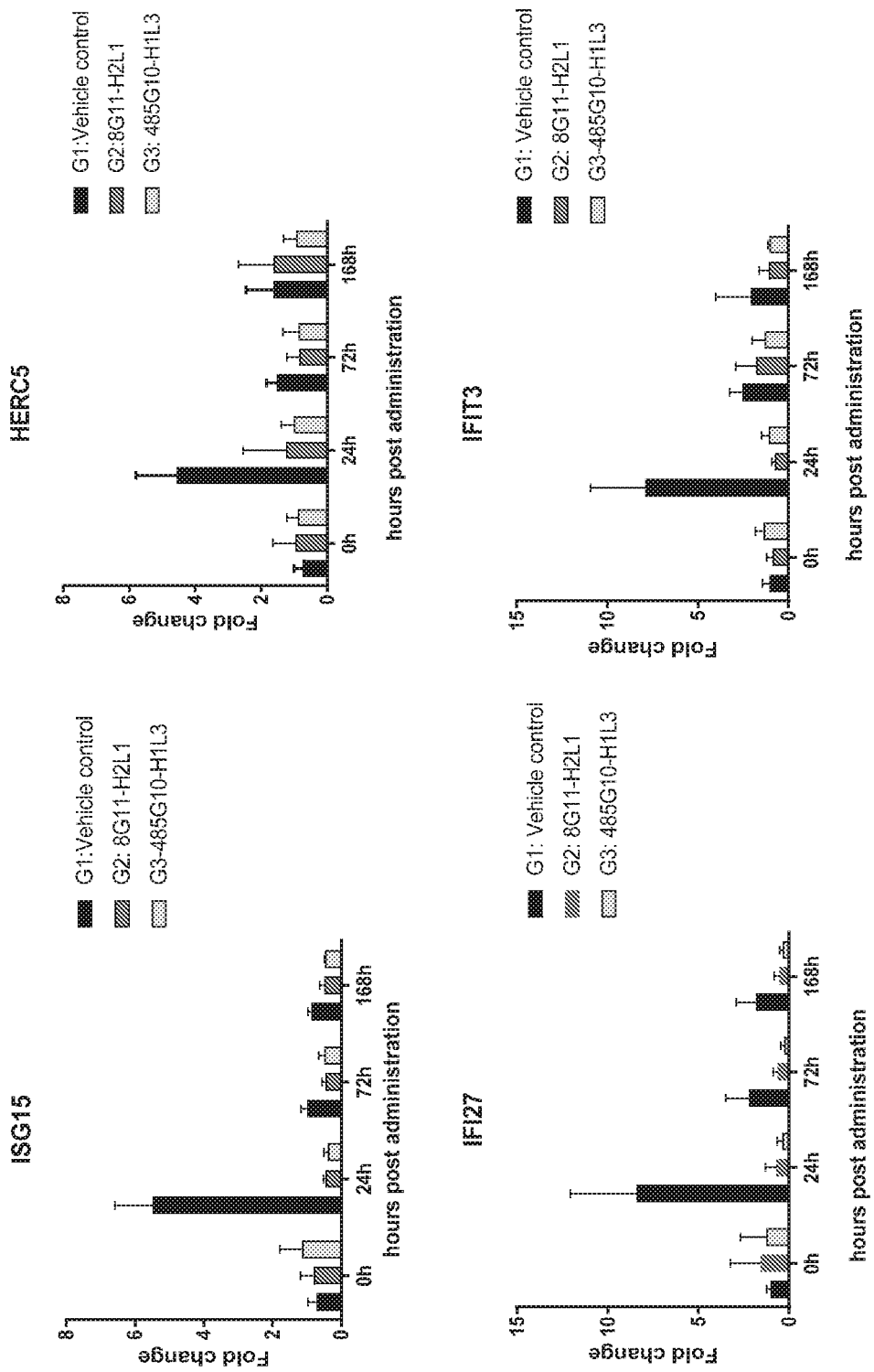
FIG. 11C shows the expression levels of type I IFN-induced gene signatures in monkey PBMCs at 24 h, 48 h and 72 h after dosing.

The expression levels of type I IFN-induced gene signatures in peripheral blood mononuclear cells were detected by real-time PCR. As shown in FIG. 11C, the mRNA levels of ISG15, HERC5, IFI27 and IFIT3 were increased rapidly within 24 h in vehicle group. Compared with vehicle control, 8G11-H2L1 and 485G10-H1L3 significantly blocked the induction effects of type I IFN on these genes.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. An antibody or fragment thereof having specificity to a human interferon alpha and beta receptor subunit 1 (IFNAR1) protein, wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein the HCDR1, HCDR2, HCDR3, LCDR1, LCDR2, and LCDR3 are
HCDR1: DYYMH (SEQ ID NO: 77), HCDR2: RIDPEDGETKYAPKFQG (SEQ ID NO: 78) or RIDPEDAETKYAPKFQG (SEQ ID NO:79), HCDR3: GGNFYVMDY (SEQ ID NO: 80), LCDR1: KASQNVGTNVV (SEQ ID NO: 81), LCDR2: SASYRVS (SEQ ID NO: 82), and LCDR3: QQKNNYPYT (SEQ ID NO: 83).

2. The antibody or fragment thereof of claim 1, wherein the antibody is a chimeric antibody or a humanized antibody.

3. The antibody or fragment thereof of claim 1, which is humanized and wherein the heavy chain variable region comprises one or more back mutations selected from the group consisting of 12V, 20L, 24G, 38K, 48I, 68A, 70I, 72A, 79A and 81L, according to Kabat numbering, and combinations thereof.

4. The antibody or fragment thereof of claim 1, which is humanized and wherein the light chain variable region comprises one or more back mutations selected from the group consisting of 4M, 13T, 21V, 43S, 46V, 74I, 78V and 87F according to Kabat numbering, and combinations thereof.

5. The antibody or fragment thereof of claim 1, comprising a heavy chain variable region comprising an amino acid sequence selected from the group consisting of SEQ ID NO: 7, and 84-87.

6. The antibody or fragment thereof of claim 1, comprising a light chain variable region comprising an amino acid sequence selected from the group consisting of SEQ ID NO: 8, and 88-91.

7. The antibody or fragment thereof of claim 1, comprising a heavy chain variable region comprising the amino acid sequence of SEQ ID NO: 85, and a light chain variable region comprising the amino acid sequence of SEQ ID NO: 88.

8. A bifunctional molecule, comprising a first antigen-binding portion having specificity to a human interferon alpha and beta receptor subunit 1 (IFNAR1) protein and a second portion having specificity to a second protein, wherein the first antigen-binding portion comprises an antibody fragment of claim 1.

9. The bifunctional molecule of claim 8, wherein the second portion comprises peptide edratide (hCDR1) or TACI-Ig.

10. The bifunctional molecule of claim 8, wherein the second portion is an antigen-binding fragment having specificity to a protein selected from the group consisting of BAFF, CD20, CD22, CTLA4, IL6, CXCL13 and C5.

11. One or more polynucleotide encoding the antibody or fragment thereof of claim 1.

12. A method of suppressing an immune response or treating an autoimmune disease or disorder in a patient in need thereof, comprising administering to the patient the antibody or fragment thereof of claim 1.

13. The method of claim 12, for treating an autoimmune disease or disorder.

14. The method of claim 13, wherein the autoimmune disease or disorder is systemic lupus erythematosus (lupus).

15. A method of detecting expression of a human interferon alpha and beta receptor subunit 1 (IFNAR1) protein in a sample, comprising contacting the sample with the antibody or fragment thereof of claim 1, and detecting the binding which indicates expression of IFNAR1 in the sample.

* * * * *